(12) United States Patent
Gunel

(10) Patent No.: US 10,648,034 B2
(45) Date of Patent: May 12, 2020

(54) COMPOSITIONS AND METHODS FOR DIAGNOSING AND TREATING MENINGIOMA

(71) Applicant: YALE UNIVERSITY, New Haven, CT (US)

(72) Inventor: Murat Gunel, Branford, CT (US)

(73) Assignee: YALE UNIVERSITY, New Haven, CT (US)

(*) Notice: Subject to any disclaimer, the term of this patent is extended or adjusted under 35 U.S.C. 154(b) by 414 days.

(21) Appl. No.: 14/389,484

(22) PCT Filed: Mar. 15, 2013

(86) PCT No.: PCT/US2013/032311
§ 371 (c)(1),
(2) Date: Sep. 30, 2014

(87) PCT Pub. No.: WO2013/154767
PCT Pub. Date: Oct. 17, 2013

(65) Prior Publication Data
US 2015/0133309 A1   May 14, 2015

Related U.S. Application Data

(60) Provisional application No. 61/621,758, filed on Apr. 9, 2012, provisional application No. 61/755,796, filed on Jan. 23, 2013.

(51) Int. Cl.
*C12Q 1/6886* (2018.01)

(52) U.S. Cl.
CPC ...... *C12Q 1/6886* (2013.01); *C12Q 2600/112* (2013.01); *C12Q 2600/156* (2013.01)

(58) Field of Classification Search
CPC .......................... C12Q 1/6883; C12Q 1/6886
See application file for complete search history.

(56) References Cited

U.S. PATENT DOCUMENTS

2006/0084056 A1   4/2006   Harbeck et al.
2009/0123928 A1   5/2009   Wood et al.

FOREIGN PATENT DOCUMENTS

WO   WO 2000/042436   7/2000

OTHER PUBLICATIONS

Pham, M.H. et al. Neurosurg. Focus 30(5):E7 (pp. 1-9)(May 2011).*
Goutagny, S. et al. Clinical Cancer Research 16(16):4155 (Aug. 2010).*
Sayagues, J.M. et al. J. Neuropathol Exp Neurol 65(5):445 (May 2006).*
Cho, Y.G. et al. APMIS 115:802 (2007).*
Leone et al., 1999, NF2 gene mutations and allelic status of 1p, 14q and 22q in sporadic meningiomas, Oncogene, 18(13), 2231-2239.

(Continued)

*Primary Examiner* — Diana B Johannsen
(74) *Attorney, Agent, or Firm* — Riverside Law LLP

(57) ABSTRACT

The present invention relates to mutations associated with neoplasia, such as meningioma. Thus, the invention relates to compositions and methods useful for the assessment, characterization, classification and treatment of neoplasia, including meningioma, based upon the presence or absence of mutations that are associated with neoplasia, including meningioma.

3 Claims, 24 Drawing Sheets

Specification includes a Sequence Listing.

(56) References Cited

OTHER PUBLICATIONS

Riemenschneider et al., 2006, Histological classification and molecular genetics of meningiomas, Lancet Neurology, 5:1045.
Clark et al., 2013, Genomic Analysis of Non-NF2 Meningiomas Reveals Mutations in TRAF7, KLF4, AKT1, and SMO, Science, 339, 1077.
Ding et al., 2008, Somatic mutations affect key pathways in lung adenocarcinoma, Nature, 455:1069.
Schmitz et al., 2001, INI1 mutations in meningiomas at a potential hotspot in exon 9, Br J Cancer, 84:199.
Xu et al., 2004, TRAF7 potentiates MEKK3-induced AP1 and CHOP activation and induces apoptosis, J Biol Chem, 279:17278.
Bouwmeester et al., 2004, A physical and functional map of the human TNF-alpha/NF-kappa B signal transduction pathway, Nat Cell Biol, 6:97.
Xie et al., 1998, Activating Smoothened mutations in sporadic basal-cell carcinoma, Nature, 391:90.
Wu et al., 2012, Small molecule inhibitors of Smoothened ciliary localization and ciliogenesis, PNAS 109:13644-13649.
Carpten et al., 2007, A transforming mutation in the pleckstrin homology domain of AKT1 in cancer, Nature, 448:439.

* cited by examiner a    Grade II Meningiomas with NF2 mutations

MN-22

MN-54

MN-96*

MN-97*

MN-171*

MN-295

MN-298

MN-1054

*Matching blood samples not available b     Grade I Meningiomas with NF2 mutations

*Matching blood samples not available. Imaging for MN-71 not available.

Grade I Meningiomas with NF2 mutations
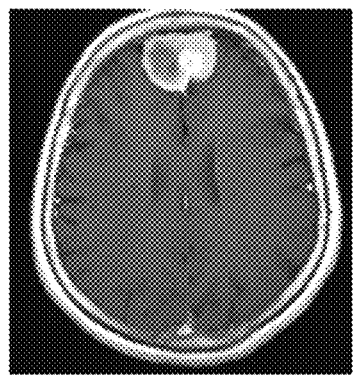
MN-301
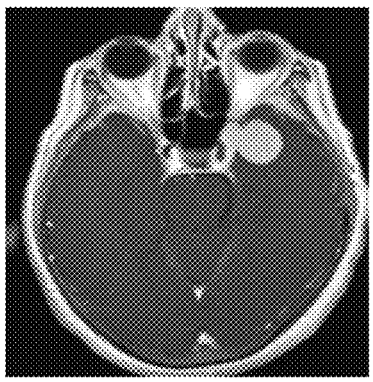
MN-306
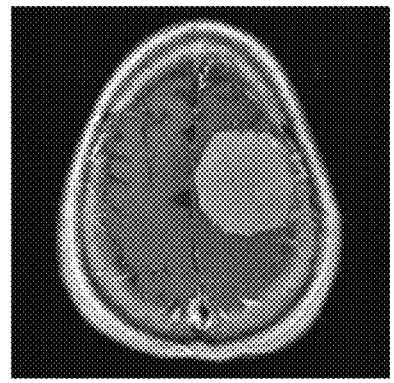
MN-1091
MN-1133
c  Grade II Meningiomas, Chromosome 22 LOH
MN-164*
*Matching blood samples not available.
Figure 10B (continued) – Figure 10C d     Grade I Meningiomas with Chromosome 22 LOH
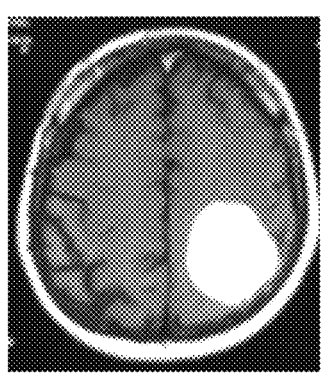
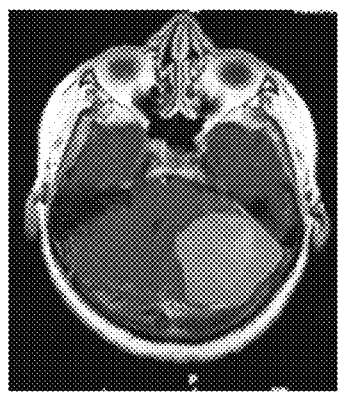
MN-95*       MN-290      MN-1041
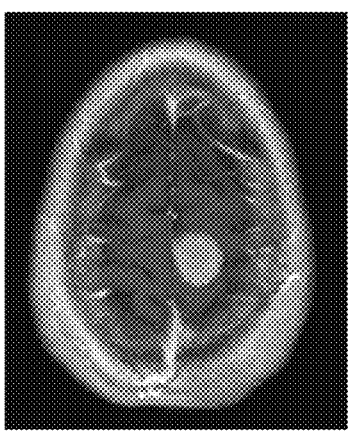
MN-1047      MN-1137
e     Grade II Meningiomas with TRAF7 mutations
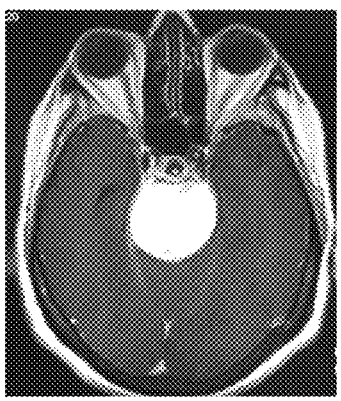
MN-16*      MN-1144
AKT1/TRAF7,      TRAF7,
LOH at chr22      LOH at chr22
*Matching blood samples not available.
Figure 10D – Figure 10E Grade I Meningiomas with TRAF7 mutations

MN-26
AKT1/TRAF7

MN-105
AKT1/TRAF7

MN-292
AKT1/TRAF7

MN-191*
KLF4/TRAF7

MN-201*
KLF4/TRAF7

MN-249
KLF4/TRAF7

MN-1025
KLF4/TRAF7

MN-303
PIK3R1/TRAF7

MN-206*
TRAF7

* Matching blood not available. Imaging for MN-1066 not available.

Grade I Meningiomas with TRAF7 mutations
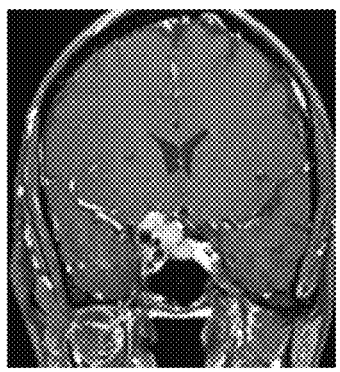 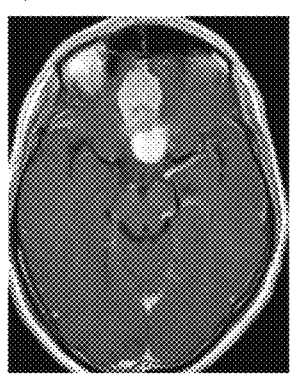 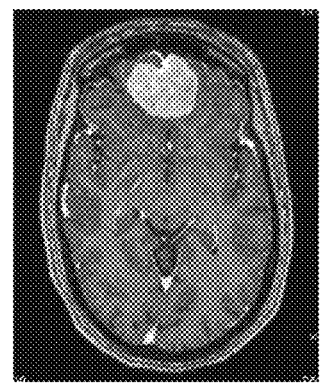
MN-304　　　　　MN-305　　　　　MN-1053
TRAF7　　　　　TRAF7　　　　　　TRAF7
g Grade I Meningiomas with SMO mutations
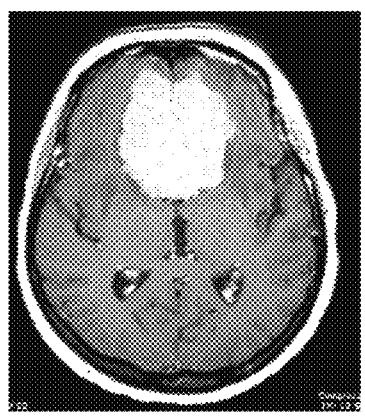 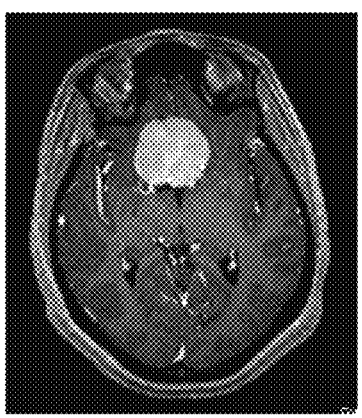
MN-1132　　　　MN-1045
SMO　　　　　　SMO
h Grade I Meningiomas with other mutations
  
MN-289　　　　　MN-300　　　　　MN-296
PIK3CA　　　　　BRCA1　　　　　CREBBP
Figure 10F (continued) – Figure 10H

| Tumor | Grade | Chr22 loss | NF2 | TRAF7 | AKT1 | KLF4 | SMO |
|---|---|---|---|---|---|---|---|
| MN-95 | 1 | Yes | | | | | |
| MN-290 | 1 | Yes | | | | | |
| MN-1041 | 1 | Yes | | | | | |
| MN-1047 | 1 | Yes | | | | | |
| MN-1137 | 1 | Yes | | | | | |
| MN-47 | 1 | Yes | p.Q453X | | | | |
| MN-52 | 1 | Yes | p.F256fs | | | | |
| MN-71 | 1 | Yes | p.T59fs | | | | |
| MN-81 | 1 | Yes | p.Q65fs | | | | |
| MN-169 | 1 | Yes | p.E460X | | | | |
| MN-288 | 1 | Yes | p.K17_M29del | | | | |
| MN-291 | 1 | Yes | p.A211fs | | | | |
| MN-293 | 1 | Yes | p.Q459X | | | | |
| MN-294 | 1 | Yes | c.363+1G>C | | | | |
| MN-297 | 1 | Yes | p.K99fs | | | | |
| MN-301 | 1 | Yes | p.G43fs | | | | |
| MN-306 | 1 | Yes | p.K44X | | | | |
| MN-1091 | 1 | Yes | p.K15fs | | | | |
| MN-1133 | 1 | Yes | p.Y207fs | | | | |
| MN-26 | 1 | | | p.C388Y | p.E17K | | |
| MN-105 | 1 | | | p.R641C | p.E17K | | |
| MN-292 | 1 | | | p.Q637H | p.E17K | | |
| MN-191 | 1 | | | p.K615E | | p.K409Q | |
| MN-201 | 1 | | | p.L580del | | p.K409Q | |
| MN-249 | 1 | | | p.R641C | | p.K409Q | |
| MN-1025 | 1 | | | p.G536S | | p.K409Q | |
| MN-1066 | 1 | | | p.N520S | | p.K409Q | |
| MN-303 | 1 | | | p.S561N | | | |
| MN-206 | 1 | | | p.G390E | | | |
| MN-304 | 1 | | | p.R653Q | | | |
| MN-305 | 1 | | | p.G536S | | | |
| MN-1053 | 1 | | | p.E353insFRRDAS | | | |
| MN-1045 | 1 | | | | | | p.L412F |
| MN-1132 | 1 | | | | | | p.W535L |
| MN-164 | 2 | Yes | | | | | |
| MN-22 | 2 | Yes | c.115-1G>A | | | | |
| MN-54 | 2 | Yes | p.Q319X | | | | |
| MN-96 | 2 | Yes | p.L14fs | | | | |
| MN-97 | 2 | Yes | p.M426fs | | | | |
| MN-171 | 2 | Yes | p.L208P | | | | |
| MN-295 | 2 | Yes | p.N104fs | | | | |
| MN-298 | 2 | Yes | p.R25fs | | | | |
| MN-1054 | 2 | Yes | p.R262X | | | | |
| MN-16 | 2 | Yes | | p.T145M | p.E17K | | |
| MN-1144 | 2 | Yes | | p.F337S | | | |

Figure 15

```
                            SEQUENCE LISTING

<160> NUMBER OF SEQ ID NOS: 11

<210> SEQ ID NO 1
<211> LENGTH: 595
<212> TYPE: PRT
<213> ORGANISM: Homo sapiens

<400> SEQUENCE: 1

Met Ala Gly Ala Ile Ala Ser Arg Met Ser Phe Ser Ser Leu Lys Arg
1               5                   10                  15

Lys Gln Pro Lys Thr Phe Thr Val Arg Ile Val Thr Met Asp Ala Glu
                20                  25                  30

Met Glu Phe Asn Cys Glu Met Lys Trp Lys Gly Lys Asp Leu Phe Asp
            35                  40                  45

Leu Val Cys Arg Thr Leu Gly Leu Arg Glu Thr Trp Phe Phe Gly Leu
    50                  55                  60

Gln Tyr Thr Ile Lys Asp Thr Val Ala Trp Leu Lys Met Asp Lys Lys
65                  70                  75                  80

Val Leu Asp His Asp Val Ser Lys Glu Glu Pro Val Thr Phe His Phe
                85                  90                  95

Leu Ala Lys Phe Tyr Pro Glu Asn Ala Glu Glu Leu Val Gln Glu
                100                 105                 110

Ile Thr Gln His Leu Phe Phe Leu Gln Val Lys Lys Gln Ile Leu Asp
            115                 120                 125

Glu Lys Ile Tyr Cys Pro Pro Glu Ala Ser Val Leu Leu Ala Ser Tyr
130                 135                 140

Ala Val Gln Ala Lys Tyr Gly Asp Tyr Asp Pro Ser Val His Lys Arg
145                 150                 155                 160

Gly Phe Leu Ala Gln Glu Glu Leu Leu Pro Lys Arg Val Ile Asn Leu
                165                 170                 175

Tyr Gln Met Thr Pro Glu Met Trp Glu Glu Arg Ile Thr Ala Trp Tyr
            180                 185                 190

Ala Glu His Arg Gly Arg Ala Arg Asp Glu Ala Glu Met Glu Tyr Leu
        195                 200                 205

Lys Ile Ala Gln Asp Leu Glu Met Tyr Gly Val Asn Tyr Phe Ala Ile
210                 215                 220

Arg Asn Lys Lys Gly Thr Glu Leu Leu Leu Gly Val Asp Ala Leu Gly
225                 230                 235                 240

Leu His Ile Tyr Asp Pro Glu Asn Arg Leu Thr Pro Lys Ile Ser Phe
                245                 250                 255

Pro Trp Asn Glu Ile Arg Asn Ile Ser Tyr Ser Asp Lys Glu Phe Thr
            260                 265                 270

Ile Lys Pro Leu Asp Lys Lys Ile Asp Val Phe Lys Phe Asn Ser Ser
        275                 280                 285

Lys Leu Arg Val Asn Lys Leu Ile Leu Gln Leu Cys Ile Gly Asn His
    290                 295                 300

Asp Leu Phe Met Arg Arg Arg Lys Ala Asp Ser Leu Glu Val Gln Gln
305                 310                 315                 320

Met Lys Ala Gln Ala Arg Glu Glu Lys Ala Arg Lys Gln Met Glu Arg
                325                 330                 335

Gln Arg Leu Ala Arg Glu Lys Gln Met Arg Glu Glu Ala Glu Arg Thr
            340                 345                 350
```

```
Arg Asp Glu Leu Glu Arg Arg Leu Leu Gln Met Lys Glu Glu Ala Thr
            355                 360                 365
Met Ala Asn Glu Ala Leu Met Arg Ser Glu Glu Thr Ala Asp Leu Leu
    370                 375                 380
Ala Glu Lys Ala Gln Ile Thr Glu Glu Ala Lys Leu Leu Ala Gln
385                 390                 395                 400
Lys Ala Ala Glu Ala Glu Gln Glu Met Gln Arg Ile Lys Ala Thr Ala
                    405                 410                 415
Ile Arg Thr Glu Glu Glu Lys Arg Leu Met Glu Gln Lys Val Leu Glu
                420                 425                 430
Ala Glu Val Leu Ala Leu Lys Met Ala Glu Glu Ser Glu Arg Arg Ala
                435                 440                 445
Lys Glu Ala Asp Gln Leu Lys Gln Asp Leu Gln Glu Ala Arg Glu Ala
            450                 455                 460
Glu Arg Arg Ala Lys Gln Lys Leu Leu Glu Ile Ala Thr Lys Pro Thr
465                 470                 475                 480
Tyr Pro Pro Met Asn Pro Ile Pro Ala Pro Leu Pro Asp Ile Pro
                    485                 490                 495
Ser Phe Asn Leu Ile Gly Asp Ser Leu Ser Phe Asp Phe Lys Asp Thr
                500                 505                 510
Asp Met Lys Arg Leu Ser Met Glu Ile Glu Lys Glu Lys Val Glu Tyr
                515                 520                 525
Met Glu Lys Ser Lys His Leu Gln Glu Gln Leu Asn Glu Leu Lys Thr
            530                 535                 540
Glu Ile Glu Ala Leu Lys Leu Lys Glu Arg Glu Thr Ala Leu Asp Ile
545                 550                 555                 560
Leu His Asn Glu Asn Ser Asp Arg Gly Gly Ser Ser Lys His Asn Thr
                    565                 570                 575
Ile Lys Lys Leu Thr Leu Gln Ser Ala Lys Ser Arg Val Ala Phe Phe
                580                 585                 590
Glu Glu Leu
        595

<210> SEQ ID NO 2
<211> LENGTH: 670
<212> TYPE: PRT
<213> ORGANISM: Homo sapiens

<400> SEQUENCE: 2

Met Ser Ser Gly Lys Ser Ala Arg Tyr Asn Arg Phe Ser Gly Gly Pro
1               5                   10                  15
Ser Asn Leu Pro Thr Pro Asp Val Thr Thr Gly Thr Arg Met Glu Thr
            20                  25                  30
Thr Phe Gly Pro Ala Phe Ser Ala Val Thr Thr Ile Thr Lys Ala Asp
        35                  40                  45
Gly Thr Ser Thr Tyr Lys Gln His Cys Arg Thr Pro Ser Ser Ser Ser
    50                  55                  60
Thr Leu Ala Tyr Ser Pro Arg Asp Glu Glu Asp Ser Met Pro Pro Ile
65                  70                  75                  80
Ser Thr Pro Arg Arg Ser Asp Ser Ala Ile Ser Val Arg Ser Leu His
                    85                  90                  95
Ser Glu Ser Ser Met Ser Leu Arg Ser Thr Phe Ser Leu Pro Glu Glu
                100                 105                 110
Glu Glu Glu Pro Glu Pro Leu Val Phe Ala Glu Gln Pro Ser Val Lys
```

```
            115                 120                 125
Leu Cys Cys Gln Leu Cys Cys Ser Val Phe Lys Asp Pro Val Ile Thr
130                 135                 140

Thr Cys Gly His Thr Phe Cys Arg Arg Cys Ala Leu Lys Ser Glu Lys
145                 150                 155                 160

Cys Pro Val Asp Asn Val Lys Leu Thr Val Val Asn Asn Ile Ala
                165                 170                 175

Val Ala Glu Gln Ile Gly Glu Leu Phe Ile His Cys Arg His Gly Cys
            180                 185                 190

Arg Val Ala Gly Ser Gly Lys Pro Pro Ile Phe Glu Val Asp Pro Arg
            195                 200                 205

Gly Cys Pro Phe Thr Ile Lys Leu Ser Ala Arg Lys Asp His Glu Gly
210                 215                 220

Ser Cys Asp Tyr Arg Pro Val Arg Cys Pro Asn Asn Pro Ser Cys Pro
225                 230                 235                 240

Pro Leu Leu Arg Met Asn Leu Glu Ala His Leu Lys Glu Cys Glu His
                245                 250                 255

Ile Lys Cys Pro His Ser Lys Tyr Gly Cys Thr Phe Ile Gly Asn Gln
                260                 265                 270

Asp Thr Tyr Glu Thr His Leu Glu Thr Cys Arg Phe Glu Gly Leu Lys
            275                 280                 285

Glu Phe Leu Gln Gln Thr Asp Asp Arg Phe His Glu Met His Val Ala
290                 295                 300

Leu Ala Gln Lys Asp Gln Glu Ile Ala Phe Leu Arg Ser Met Leu Gly
305                 310                 315                 320

Lys Leu Ser Glu Lys Ile Asp Gln Leu Glu Lys Ser Leu Glu Leu Lys
                325                 330                 335

Phe Asp Val Leu Asp Glu Asn Gln Ser Lys Leu Ser Glu Asp Leu Met
                340                 345                 350

Glu Phe Arg Arg Asp Ala Ser Met Leu Asn Asp Glu Leu Ser His Ile
            355                 360                 365

Asn Ala Arg Leu Asn Met Gly Ile Leu Gly Ser Tyr Asp Pro Gln Gln
370                 375                 380

Ile Phe Lys Cys Lys Gly Thr Phe Val Gly His Gln Gly Pro Val Trp
385                 390                 395                 400

Cys Leu Cys Val Tyr Ser Met Gly Asp Leu Leu Phe Ser Gly Ser Ser
                405                 410                 415

Asp Lys Thr Ile Lys Val Trp Asp Thr Cys Thr Thr Tyr Lys Cys Gln
            420                 425                 430

Lys Thr Leu Glu Gly His Asp Gly Ile Val Leu Ala Leu Cys Ile Gln
            435                 440                 445

Gly Cys Lys Leu Tyr Ser Gly Ser Ala Asp Cys Thr Ile Ile Val Trp
            450                 455                 460

Asp Ile Gln Asn Leu Gln Lys Val Asn Thr Ile Arg Ala His Asp Asn
465                 470                 475                 480

Pro Val Cys Thr Leu Val Ser Ser His Asn Val Leu Phe Ser Gly Ser
                485                 490                 495

Leu Lys Ala Ile Lys Val Trp Asp Ile Val Gly Thr Glu Leu Lys Leu
                500                 505                 510

Lys Lys Glu Leu Thr Gly Leu Asn His Trp Val Arg Ala Leu Val Ala
            515                 520                 525

Ala Gln Ser Tyr Leu Tyr Ser Gly Ser Tyr Gln Thr Ile Lys Ile Trp
            530                 535                 540
```

Asp Ile Arg Thr Leu Asp Cys Ile His Val Leu Gln Thr Ser Gly Gly
545                 550                 555                 560

Ser Val Tyr Ser Ile Ala Val Thr Asn His Ile Val Cys Gly Thr
            565                 570                 575

Tyr Glu Asn Leu Ile His Val Trp Asp Ile Glu Ser Lys Glu Gln Val
            580                 585                 590

Arg Thr Leu Thr Gly His Val Gly Thr Val Tyr Ala Leu Ala Val Ile
        595                 600                 605

Ser Thr Pro Asp Gln Thr Lys Val Phe Ser Ala Ser Tyr Asp Arg Ser
        610                 615                 620

Leu Arg Val Trp Ser Met Asp Asn Met Ile Cys Thr Gln Thr Leu Leu
625                 630                 635                 640

Arg His Gln Gly Ser Val Thr Ala Leu Ala Val Ser Arg Gly Arg Leu
                645                 650                 655

Phe Ser Gly Ala Val Asp Ser Thr Val Lys Val Trp Thr Cys
            660                 665                 670

<210> SEQ ID NO 3
<211> LENGTH: 480
<212> TYPE: PRT
<213> ORGANISM: Homo sapiens

<400> SEQUENCE: 3

Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu

```
                    245                 250                 255
Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
            275                 280                 285

Lys Ile Thr Asp Phe Gly Leu Cys Lys Glu Gly Ile Lys Asp Gly Ala
290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
            355                 360                 365

Pro Arg Thr Leu Gly Pro Glu Ala Lys Ser Leu Leu Ser Gly Leu Leu
            370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
            435                 440                 445

Ile Thr Pro Pro Asp Gln Asp Asp Ser Met Glu Cys Val Asp Ser Glu
450                 455                 460

Arg Arg Pro His Phe Pro Gln Phe Ser Tyr Ser Ala Ser Gly Thr Ala
465                 470                 475                 480

<210> SEQ ID NO 4
<211> LENGTH: 479
<212> TYPE: PRT
<213> ORGANISM: Homo sapiens

<400> SEQUENCE: 4

Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
            20                  25                  30

Thr Leu Arg Gln Ala Gly Ala Pro Asn Asn Arg Trp Arg Glu Glu Leu
        35                  40                  45

Ser His Met Lys Arg Leu Pro Pro Val Leu Pro Gly Arg Pro Tyr Asp
    50                  55                  60

Leu Ala Ala Ala Thr Val Ala Thr Asp Leu Glu Ser Gly Gly Ala Gly
65                  70                  75                  80

Ala Ala Cys Gly Gly Ser Asn Leu Ala Pro Leu Pro Arg Arg Glu Thr
                85                  90                  95

Glu Glu Phe Asn Asp Leu Leu Asp Leu Asp Phe Ile Leu Ser Asn Ser
            100                 105                 110

Leu Thr His Pro Pro Glu Ser Val Ala Ala Thr Val Ser Ser Ser Ala
        115                 120                 125

Ser Ala Ser Ser Ser Ser Ser Pro Ser Ser Ser Gly Pro Ala Ser Ala
    130                 135                 140
```

```
Pro Ser Thr Cys Ser Phe Thr Tyr Pro Ile Arg Ala Gly Asn Asp Pro
145                 150                 155                 160

Gly Val Ala Pro Gly Gly Thr Gly Gly Gly Leu Leu Tyr Gly Arg Glu
            165                 170                 175

Ser Ala Pro Pro Pro Thr Ala Pro Phe Asn Leu Ala Asp Ile Asn Asp
                180                 185                 190

Val Ser Pro Ser Gly Gly Phe Val Ala Glu Leu Leu Arg Pro Glu Leu
        195                 200                 205

Asp Pro Val Tyr Ile Pro Pro Gln Gln Pro Gln Pro Gly Gly Gly
    210                 215                 220

Leu Met Gly Lys Phe Val Leu Lys Ala Ser Leu Ser Ala Pro Gly Ser
225                 230                 235                 240

Glu Tyr Gly Ser Pro Ser Val Ile Ser Val Ser Lys Gly Ser Pro Asp
                245                 250                 255

Gly Ser His Pro Val Val Ala Pro Tyr Asn Gly Gly Pro Pro Arg
                260                 265                 270

Thr Cys Pro Lys Ile Lys Gln Glu Ala Val Ser Ser Cys Thr His Leu
        275                 280                 285

Gly Ala Gly Pro Pro Leu Ser Asn Gly His Arg Pro Ala Ala His Asp
290                 295                 300

Phe Pro Leu Gly Arg Gln Leu Pro Ser Arg Thr Thr Pro Thr Leu Gly
305                 310                 315                 320

Leu Glu Glu Val Leu Ser Ser Arg Asp Cys His Pro Ala Leu Pro Leu
                325                 330                 335

Pro Pro Gly Phe His Pro His Pro Gly Pro Asn Tyr Pro Ser Phe Leu
            340                 345                 350

Pro Asp Gln Met Gln Pro Gln Val Pro Pro Leu His Tyr Gln Glu Leu
        355                 360                 365

Met Pro Pro Gly Ser Cys Met Pro Glu Glu Pro Lys Pro Lys Arg Gly
    370                 375                 380

Arg Arg Ser Trp Pro Arg Lys Arg Thr Ala Thr His Thr Cys Asp Tyr
385                 390                 395                 400

Ala Gly Cys Gly Lys Thr Tyr Thr Lys Ser Ser His Leu Lys Ala His
                405                 410                 415

Leu Arg Thr His Thr Gly Glu Lys Pro Tyr His Cys Asp Trp Asp Gly
            420                 425                 430

Cys Gly Trp Lys Phe Ala Arg Ser Asp Glu Leu Thr Arg His Tyr Arg
        435                 440                 445

Lys His Thr Gly His Arg Pro Phe Gln Cys Gln Lys Cys Asp Arg Ala
    450                 455                 460

Phe Ser Arg Ser Asp His Leu Ala Leu His Met Lys Arg His Phe
465                 470                 475
```

<210> SEQ ID NO 5
<211> LENGTH: 787
<212> TYPE: PRT
<213> ORGANISM: Homo sapiens

<400> SEQUENCE: 5

```
Met Ala Ala Ala Arg Pro Ala Arg Gly Pro Glu Leu Pro Leu Leu Gly
1               5                   10                  15

Leu Leu Leu Leu Leu Leu Leu Gly Asp Pro Gly Arg Gly Ala Ala Ser
                20                  25                  30

Ser Gly Asn Ala Thr Gly Pro Gly Pro Arg Ser Ala Gly Gly Ser Ala
            35                  40                  45
```

-continued

Arg Arg Ser Ala Ala Val Thr Gly Pro Pro Pro Leu Ser His Cys
        50              55              60

Gly Arg Ala Ala Pro Cys Glu Pro Leu Arg Tyr Asn Val Cys Leu Gly
 65              70              75              80

Ser Val Leu Pro Tyr Gly Ala Thr Ser Thr Leu Leu Ala Gly Asp Ser
                85              90              95

Asp Ser Gln Glu Glu Ala His Gly Lys Leu Val Leu Trp Ser Gly Leu
            100             105             110

Arg Asn Ala Pro Arg Cys Trp Ala Val Ile Gln Pro Leu Leu Cys Ala
        115             120             125

Val Tyr Met Pro Lys Cys Glu Asn Asp Arg Val Glu Leu Pro Ser Arg
130             135             140

Thr Leu Cys Gln Ala Thr Arg Gly Pro Cys Ala Ile Val Glu Arg Glu
145             150             155             160

Arg Gly Trp Pro Asp Phe Leu Arg Cys Thr Pro Asp Arg Phe Pro Glu
                165             170             175

Gly Cys Thr Asn Glu Val Gln Asn Ile Lys Phe Asn Ser Ser Gly Gln
            180             185             190

Cys Glu Val Pro Leu Val Arg Thr Asp Asn Pro Lys Ser Trp Tyr Glu
            195             200             205

Asp Val Glu Gly Cys Gly Ile Gln Cys Gln Asn Pro Leu Phe Thr Glu
210             215             220

Ala Glu His Gln Asp Met His Ser Tyr Ile Ala Ala Phe Gly Ala Val
225             230             235             240

Thr Gly Leu Cys Thr Leu Phe Thr Leu Ala Thr Phe Val Ala Asp Trp
                245             250             255

Arg Asn Ser Asn Arg Tyr Pro Ala Val Ile Leu Phe Tyr Val Asn Ala
            260             265             270

Cys Phe Phe Val Gly Ser Ile Gly Trp Leu Ala Gln Phe Met Asp Gly
            275             280             285

Ala Arg Arg Glu Ile Val Cys Arg Ala Asp Gly Thr Met Arg Leu Gly
290             295             300

Glu Pro Thr Ser Asn Glu Thr Leu Ser Cys Val Ile Ile Phe Val Ile
305             310             315             320

Val Tyr Tyr Ala Leu Met Ala Gly Val Val Trp Phe Val Val Leu Thr
                325             330             335

Tyr Ala Trp His Thr Ser Phe Lys Ala Leu Gly Thr Thr Tyr Gln Pro
            340             345             350

Leu Ser Gly Lys Thr Ser Tyr Phe His Leu Leu Thr Trp Ser Leu Pro
            355             360             365

Phe Val Leu Thr Val Ala Ile Leu Ala Val Ala Gln Val Asp Gly Asp
370             375             380

Ser Val Ser Gly Ile Cys Phe Val Gly Tyr Lys Asn Tyr Arg Tyr Arg
385             390             395             400

Ala Gly Phe Val Leu Ala Pro Ile Gly Leu Val Leu Ile Val Gly Gly
                405             410             415

Tyr Phe Leu Ile Arg Gly Val Met Thr Leu Phe Ser Ile Lys Ser Asn
            420             425             430

His Pro Gly Leu Leu Ser Glu Lys Ala Ala Ser Lys Ile Asn Glu Thr
            435             440             445

Met Leu Arg Leu Gly Ile Phe Gly Phe Leu Ala Phe Gly Phe Val Leu
450             455             460

Ile Thr Phe Ser Cys His Phe Tyr Asp Phe Phe Asn Gln Ala Glu Trp
465                 470                 475                 480

Glu Arg Ser Phe Arg Asp Tyr Val Leu Cys Gln Ala Asn Val Thr Ile
            485                 490                 495

Gly Leu Pro Thr Lys Gln Pro Ile Pro Asp Cys Glu Ile Lys Asn Arg
        500                 505                 510

Pro Ser Leu Leu Val Glu Lys Ile Asn Leu Phe Ala Met Phe Gly Thr
    515                 520                 525

Gly Ile Ala Met Ser Thr Trp Val Trp Thr Lys Ala Thr Leu Leu Ile
530                 535                 540

Trp Arg Arg Thr Trp Cys Arg Leu Thr Gly Gln Ser Asp Asp Glu Pro
545                 550                 555                 560

Lys Arg Ile Lys Lys Ser Lys Met Ile Ala Lys Ala Phe Ser Lys Arg
                565                 570                 575

His Glu Leu Leu Gln Asn Pro Gly Gln Glu Leu Ser Phe Ser Met His
            580                 585                 590

Thr Val Ser His Asp Gly Pro Val Ala Gly Leu Ala Phe Asp Leu Asn
        595                 600                 605

Glu Pro Ser Ala Asp Val Ser Ser Ala Trp Ala Gln His Val Thr Lys
    610                 615                 620

Met Val Ala Arg Arg Gly Ala Ile Leu Pro Gln Asp Ile Ser Val Thr
625                 630                 635                 640

Pro Val Ala Thr Pro Val Pro Pro Glu Glu Gln Ala Asn Leu Trp Leu
                645                 650                 655

Val Glu Ala Glu Ile Ser Pro Glu Leu Gln Lys Arg Leu Gly Arg Lys
            660                 665                 670

Lys Lys Arg Arg Lys Arg Lys Lys Glu Val Cys Pro Leu Ala Pro Pro
        675                 680                 685

Pro Glu Leu His Pro Pro Ala Pro Ala Pro Ser Thr Ile Pro Arg Leu
    690                 695                 700

Pro Gln Leu Pro Arg Gln Lys Cys Leu Val Ala Ala Gly Ala Trp Gly
705                 710                 715                 720

Ala Gly Asp Ser Cys Arg Gln Gly Ala Trp Thr Leu Val Ser Asn Pro
                725                 730                 735

Phe Cys Pro Glu Pro Ser Pro Pro Gln Asp Pro Phe Leu Pro Ser Ala
            740                 745                 750

Pro Ala Pro Val Ala Trp Ala His Gly Arg Arg Gln Gly Leu Gly Pro
        755                 760                 765

Ile His Ser Arg Thr Asn Leu Met Asp Thr Glu Leu Met Asp Ala Asp
    770                 775                 780

Ser Asp Phe
785

<210> SEQ ID NO 6
<211> LENGTH: 1068
<212> TYPE: PRT
<213> ORGANISM: Homo sapiens

<400> SEQUENCE: 6

Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

```
Leu Phe Lys Glu Ala Arg Lys Tyr Pro Leu His Gln Leu Leu Gln Asp
         50                  55                  60

Glu Ser Ser Tyr Ile Phe Val Ser Val Thr Gln Ala Glu Arg Glu
 65                  70                  75                  80

Glu Phe Phe Asp Glu Thr Arg Arg Leu Cys Asp Leu Arg Leu Phe Gln
                     85                  90                  95

Pro Phe Leu Lys Val Ile Glu Pro Val Gly Asn Arg Glu Lys Ile
                 100                 105                 110

Leu Asn Arg Glu Ile Gly Phe Ala Ile Gly Met Pro Val Cys Glu Phe
             115                 120                 125

Asp Met Val Lys Asp Pro Glu Val Gln Asp Phe Arg Arg Asn Ile Leu
 130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                 165                 170                 175

Leu Pro Lys His Ile Tyr Asn Lys Leu Asp Lys Gly Gln Ile Ile Val
             180                 185                 190

Val Ile Trp Val Ile Val Ser Pro Asn Asn Asp Lys Gln Lys Tyr Thr
     195                 200                 205

Leu Lys Ile Asn His Asp Cys Val Pro Glu Gln Val Ile Ala Glu Ala
210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                 245                 250                 255

Cys Asp Glu Tyr Phe Leu Glu Lys Tyr Pro Leu Ser Gln Tyr Lys Tyr
             260                 265                 270

Ile Arg Ser Cys Ile Met Leu Gly Arg Met Pro Asn Leu Met Leu Met
         275                 280                 285

Ala Lys Glu Ser Leu Tyr Ser Gln Leu Pro Met Asp Cys Phe Thr Met
 290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                 325                 330                 335

Lys Ile Leu Cys Ala Thr Tyr Val Asn Val Asn Ile Arg Asp Ile Asp
             340                 345                 350

Lys Ile Tyr Val Arg Thr Gly Ile Tyr His Gly Gly Glu Pro Leu Cys
         355                 360                 365

Asp Asn Val Asn Thr Gln Arg Val Pro Cys Ser Asn Pro Arg Trp Asn
 370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                 405                 410                 415

Glu Glu His Cys Pro Leu Ala Trp Gly Asn Ile Asn Leu Phe Asp Tyr
             420                 425                 430

Thr Asp Thr Leu Val Ser Gly Lys Met Ala Leu Asn Leu Trp Pro Val
         435                 440                 445

Pro His Gly Leu Glu Asp Leu Leu Asn Pro Ile Gly Val Thr Gly Ser
 450                 455                 460
```

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
            485                 490                 495

Asn Trp Ser Val Ser Arg Glu Ala Gly Phe Ser Tyr Ser His Ala Gly
            500                 505                 510

Leu Ser Asn Arg Leu Ala Arg Asp Asn Glu Leu Arg Glu Asn Asp Lys
            515                 520                 525

Glu Gln Leu Lys Ala Ile Ser Thr Arg Asp Pro Leu Ser Glu Ile Thr
    530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
            565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
            595                 600                 605

Pro Met Val Arg Gly Phe Ala Val Arg Cys Leu Glu Lys Tyr Leu Thr
    610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
            645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
            675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
            725                 730                 735

Glu Gln Met Arg Arg Pro Asp Phe Met Asp Ala Leu Gln Gly Phe Leu
            740                 745                 750

Ser Pro Leu Asn Pro Ala His Gln Leu Gly Asn Leu Arg Leu Glu Glu
    755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
            805                 810                 815

Ile Arg Ile Met Glu Asn Ile Trp Gln Asn Gly Leu Asp Leu Arg
            820                 825                 830

Met Leu Pro Tyr Gly Cys Leu Ser Ile Gly Asp Cys Val Gly Leu Ile
            835                 840                 845

Glu Val Val Arg Asn Ser His Thr Ile Met Gln Ile Gln Cys Lys Gly
            850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu

```
                      885                 890                 895
Phe Thr Arg Ser Cys Ala Gly Tyr Cys Val Ala Thr Phe Ile Leu Gly
                900                 905                 910
Ile Gly Asp Arg His Asn Ser Asn Ile Met Val Lys Asp Asp Gly Gln
                915                 920                 925
Leu Phe His Ile Asp Phe Gly His Phe Leu Asp His Lys Lys Lys Lys
            930                 935                 940
Phe Gly Tyr Lys Arg Glu Arg Val Pro Phe Val Leu Thr Gln Asp Phe
945                 950                 955                 960
Leu Ile Val Ile Ser Lys Gly Ala Gln Glu Cys Thr Lys Thr Arg Glu
                965                 970                 975
Phe Glu Arg Phe Gln Glu Met Cys Tyr Lys Ala Tyr Leu Ala Ile Arg
                980                 985                 990
Gln His Ala Asn Leu Phe Ile Asn Leu Phe Ser Met Met Leu Gly Ser
            995                 1000                1005
Gly Met Pro Glu Leu Gln Ser Phe Asp Asp Ile Ala Tyr Ile Arg
        1010                1015                1020
Lys Thr Leu Ala Leu Asp Lys Thr Glu Gln Glu Ala Leu Glu Tyr
        1025                1030                1035
Phe Met Lys Gln Met Asn Asp Ala His His Gly Gly Trp Thr Thr
        1040                1045                1050
Lys Met Asp Trp Ile Phe His Thr Ile Lys Gln His Ala Leu Asn
        1055                1060                1065

<210> SEQ ID NO 7
<211> LENGTH: 724
<212> TYPE: PRT
<213> ORGANISM: Homo sapiens

<400> SEQUENCE: 7

Met Ser Ala Glu Gly Tyr Gln Tyr Arg Ala Leu Tyr Asp Tyr Lys Lys
1               5                   10                  15
Glu Arg Glu Glu Asp Ile Asp Leu His Leu Gly Asp Ile Leu Thr Val
                20                  25                  30
Asn Lys Gly Ser Leu Val Ala Leu Gly Phe Ser Asp Gly Gln Glu Ala
            35                  40                  45
Arg Pro Glu Glu Ile Gly Trp Leu Asn Gly Tyr Asn Glu Thr Thr Gly
50                  55                  60
Glu Arg Gly Asp Phe Pro Gly Thr Tyr Val Glu Tyr Ile Gly Arg Lys
65                  70                  75                  80
Lys Ile Ser Pro Pro Thr Pro Lys Pro Arg Pro Arg Pro Leu Pro
                85                  90                  95
Val Ala Pro Gly Ser Ser Lys Thr Glu Ala Asp Val Glu Gln Gln Ala
                100                 105                 110
Leu Thr Leu Pro Asp Leu Ala Glu Gln Phe Ala Pro Pro Asp Ile Ala
            115                 120                 125
Pro Pro Leu Leu Ile Lys Leu Val Glu Ala Ile Glu Lys Lys Gly Leu
        130                 135                 140
Glu Cys Ser Thr Leu Tyr Arg Thr Gln Ser Ser Ser Asn Leu Ala Glu
145                 150                 155                 160
Leu Arg Gln Leu Leu Asp Cys Asp Thr Pro Ser Val Asp Leu Glu Met
                165                 170                 175
Ile Asp Val His Val Leu Ala Asp Ala Phe Lys Arg Tyr Leu Leu Asp
                180                 185                 190
```

```
Leu Pro Asn Pro Val Ile Pro Ala Ala Val Tyr Ser Glu Met Ile Ser
        195                 200                 205

Leu Ala Pro Glu Val Gln Ser Ser Glu Tyr Ile Gln Leu Leu Lys
    210                 215                 220

Lys Leu Ile Arg Ser Pro Ser Ile Pro His Gln Tyr Trp Leu Thr Leu
225                 230                 235                 240

Gln Tyr Leu Leu Lys His Phe Phe Lys Leu Ser Gln Thr Ser Ser Lys
                245                 250                 255

Asn Leu Leu Asn Ala Arg Val Leu Ser Glu Ile Phe Ser Pro Met Leu
            260                 265                 270

Phe Arg Phe Ser Ala Ala Ser Ser Asp Asn Thr Glu Asn Leu Ile Lys
        275                 280                 285

Val Ile Glu Ile Leu Ile Ser Thr Glu Trp Asn Glu Arg Gln Pro Ala
    290                 295                 300

Pro Ala Leu Pro Pro Lys Pro Pro Lys Pro Thr Thr Val Ala Asn Asn
305                 310                 315                 320

Gly Met Asn Asn Asn Met Ser Leu Gln Asp Ala Glu Trp Tyr Trp Gly
                325                 330                 335

Asp Ile Ser Arg Glu Glu Val Asn Glu Lys Leu Arg Asp Thr Ala Asp
            340                 345                 350

Gly Thr Phe Leu Val Arg Asp Ala Ser Thr Lys Met His Gly Asp Tyr
        355                 360                 365

Thr Leu Thr Leu Arg Lys Gly Gly Asn Asn Lys Leu Ile Lys Ile Phe
    370                 375                 380

His Arg Asp Gly Lys Tyr Gly Phe Ser Asp Pro Leu Thr Phe Ser Ser
385                 390                 395                 400

Val Val Glu Leu Ile Asn His Tyr Arg Asn Glu Ser Leu Ala Gln Tyr
                405                 410                 415

Asn Pro Lys Leu Asp Val Lys Leu Leu Tyr Pro Val Ser Lys Tyr Gln
            420                 425                 430

Gln Asp Gln Val Val Lys Glu Asp Asn Ile Glu Ala Val Gly Lys Lys
        435                 440                 445

Leu His Glu Tyr Asn Thr Gln Phe Gln Glu Lys Ser Arg Glu Tyr Asp
    450                 455                 460

Arg Leu Tyr Glu Glu Tyr Thr Arg Thr Ser Gln Glu Ile Gln Met Lys
465                 470                 475                 480

Arg Thr Ala Ile Glu Ala Phe Asn Glu Thr Ile Lys Ile Phe Glu Glu
                485                 490                 495

Gln Cys Gln Thr Gln Glu Arg Tyr Ser Lys Glu Tyr Ile Glu Lys Phe
            500                 505                 510

Lys Arg Glu Gly Asn Glu Lys Glu Ile Gln Arg Ile Met His Asn Tyr
        515                 520                 525

Asp Lys Leu Lys Ser Arg Ile Ser Glu Ile Ile Asp Ser Arg Arg Arg
    530                 535                 540

Leu Glu Glu Asp Leu Lys Lys Gln Ala Ala Glu Tyr Arg Glu Ile Asp
545                 550                 555                 560

Lys Arg Met Asn Ser Ile Lys Pro Asp Leu Ile Gln Leu Arg Lys Thr
                565                 570                 575

Arg Asp Gln Tyr Leu Met Trp Leu Thr Gln Lys Gly Val Arg Gln Lys
            580                 585                 590

Lys Leu Asn Glu Trp Leu Gly Asn Glu Asn Thr Glu Asp Gln Tyr Ser
        595                 600                 605

Leu Val Glu Asp Asp Glu Asp Leu Pro His His Asp Glu Lys Thr Trp
```

-continued

```
             610                 615                 620

Asn Val Gly Ser Ser Asn Arg Asn Lys Ala Glu Asn Leu Leu Arg Gly
625                 630                 635                 640

Lys Arg Asp Gly Thr Phe Leu Val Arg Glu Ser Ser Lys Gln Gly Cys
                645                 650                 655

Tyr Ala Cys Ser Val Val Val Asp Gly Glu Val Lys His Cys Val Ile
                660                 665                 670

Asn Lys Thr Ala Thr Gly Tyr Gly Phe Ala Glu Pro Tyr Asn Leu Tyr
            675                 680                 685

Ser Ser Leu Lys Glu Leu Val Leu His Tyr Gln His Thr Ser Leu Val
            690                 695                 700

Gln His Asn Asp Ser Leu Asn Val Thr Leu Ala Tyr Pro Val Tyr Ala
705                 710                 715                 720

Gln Gln Arg Arg

<210> SEQ ID NO 8
<211> LENGTH: 1863
<212> TYPE: PRT
<213> ORGANISM: Homo sapiens

<400> SEQUENCE: 8

Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
                20                  25                  30

Glu Pro Val Ser Thr Lys Cys Asp His Ile Phe Cys Lys Phe Cys Met
            35                  40                  45

Leu Lys Leu Leu Asn Gln Lys Lys Gly Pro Ser Gln Cys Pro Leu Cys
        50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
    210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
```

```
            260                 265                 270
Pro Cys Gly Thr Asn Thr His Ala Ser Ser Leu Gln His Glu Asn Ser
            275                 280                 285

Ser Leu Leu Leu Thr Lys Asp Arg Met Asn Val Glu Lys Ala Glu Phe
            290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335

Glu Lys Lys Val Asp Leu Asn Ala Asp Pro Leu Cys Glu Arg Lys Glu
                340                 345                 350

Trp Asn Lys Gln Lys Leu Pro Cys Ser Glu Asn Pro Arg Asp Thr Glu
            355                 360                 365

Asp Val Pro Trp Ile Thr Leu Asn Ser Ser Ile Gln Lys Val Asn Glu
            370                 375                 380

Trp Phe Ser Arg Ser Asp Glu Leu Leu Gly Ser Asp Asp Ser His Asp
385                 390                 395                 400

Gly Glu Ser Glu Ser Asn Ala Lys Val Ala Asp Val Leu Asp Val Leu
                405                 410                 415

Asn Glu Val Asp Glu Tyr Ser Gly Ser Ser Glu Lys Ile Asp Leu Leu
                420                 425                 430

Ala Ser Asp Pro His Glu Ala Leu Ile Cys Lys Ser Glu Arg Val His
            435                 440                 445

Ser Lys Ser Val Glu Ser Asn Ile Glu Asp Lys Ile Phe Gly Lys Thr
            450                 455                 460

Tyr Arg Lys Lys Ala Ser Leu Pro Asn Leu Ser His Val Thr Glu Asn
465                 470                 475                 480

Leu Ile Ile Gly Ala Phe Val Thr Glu Pro Gln Ile Ile Gln Glu Arg
                485                 490                 495

Pro Leu Thr Asn Lys Leu Lys Arg Lys Arg Arg Pro Thr Ser Gly Leu
            500                 505                 510

His Pro Glu Asp Phe Ile Lys Lys Ala Asp Leu Ala Val Gln Lys Thr
            515                 520                 525

Pro Glu Met Ile Asn Gln Gly Thr Asn Gln Thr Glu Gln Asn Gly Gln
            530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
                565                 570                 575

Glu Ser Ala Phe Lys Thr Lys Ala Glu Pro Ile Ser Ser Ser Ile Ser
                580                 585                 590

Asn Met Glu Leu Glu Leu Asn Ile His Asn Ser Lys Ala Pro Lys Lys
            595                 600                 605

Asn Arg Leu Arg Arg Lys Ser Ser Thr Arg His Ile His Ala Leu Glu
            610                 615                 620

Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn
                645                 650                 655

Gln Met Pro Val Arg His Ser Arg Asn Leu Gln Leu Met Glu Gly Lys
                660                 665                 670

Glu Pro Ala Thr Gly Ala Lys Lys Ser Asn Lys Pro Asn Glu Gln Thr
            675                 680                 685
```

-continued

Ser Lys Arg His Asp Ser Asp Thr Phe Pro Glu Leu Lys Leu Thr Asn
690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
            725                 730                 735

Thr Val Lys Val Ser Asn Asn Ala Glu Asp Pro Lys Asp Leu Met Leu
            740                 745                 750

Ser Gly Glu Arg Val Leu Gln Thr Glu Arg Ser Val Glu Ser Ser Ser
        755                 760                 765

Ile Ser Leu Val Pro Gly Thr Asp Tyr Gly Thr Gln Glu Ser Ile Ser
770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                805                 810                 815

Gly Cys Ser Lys Asp Asn Arg Asn Asp Thr Glu Gly Phe Lys Tyr Pro
            820                 825                 830

Leu Gly His Glu Val Asn His Ser Arg Glu Thr Ser Ile Glu Met Glu
        835                 840                 845

Glu Ser Glu Leu Asp Ala Gln Tyr Leu Gln Asn Thr Phe Lys Val Ser
850                 855                 860

Lys Arg Gln Ser Phe Ala Pro Phe Ser Asn Pro Gly Asn Ala Glu Glu
865                 870                 875                 880

Glu Cys Ala Thr Phe Ser Ala His Ser Gly Ser Leu Lys Lys Gln Ser
                885                 890                 895

Pro Lys Val Thr Phe Glu Cys Glu Gln Lys Glu Glu Asn Gln Gly Lys
            900                 905                 910

Asn Glu Ser Asn Ile Lys Pro Val Gln Thr Val Asn Ile Thr Ala Gly
        915                 920                 925

Phe Pro Val Val Gly Gln Lys Asp Lys Pro Val Asp Asn Ala Lys Cys
930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
                965                 970                 975

Pro Tyr Arg Ile Pro Pro Leu Phe Pro Ile Lys Ser Phe Val Lys Thr
            980                 985                 990

Lys Cys Lys Lys Asn Leu Leu Glu Glu Asn Phe Glu Glu His Ser Met
        995                 1000                1005

Ser Pro Glu Arg Glu Met Gly Asn Glu Asn Ile Pro Ser Thr Val
    1010                1015                1020

Ser Thr Ile Ser Arg Asn Asn Ile Arg Glu Asn Val Phe Lys Glu
    1025                1030                1035

Ala Ser Ser Ser Asn Ile Asn Glu Val Gly Ser Ser Thr Asn Glu
    1040                1045                1050

Val Gly Ser Ser Ile Asn Glu Ile Gly Ser Ser Asp Glu Asn Ile
    1055                1060                1065

Gln Ala Glu Leu Gly Arg Asn Arg Gly Pro Lys Leu Asn Ala Met
    1070                1075                1080

Leu Arg Leu Gly Val Leu Gln Pro Glu Val Tyr Lys Gln Ser Leu
    1085                1090                1095

-continued

| | | | | | | | | | | | | |
|---|---|---|---|---|---|---|---|---|---|---|---|---|
| Pro | Gly | Ser | Asn | Cys | Lys | His | Pro | Glu | Ile | Lys | Lys | Gln | Glu | Tyr |
| | 1100 | | | | 1105 | | | | 1110 | | | |

| Glu | Glu | Val | Val | Gln | Thr | Val | Asn | Thr | Asp | Phe | Ser | Pro | Tyr | Leu |
| | 1115 | | | | 1120 | | | | 1125 | | | |

| Ile | Ser | Asp | Asn | Leu | Glu | Gln | Pro | Met | Gly | Ser | Ser | His | Ala | Ser |
| | 1130 | | | | 1135 | | | | 1140 | | | |

| Gln | Val | Cys | Ser | Glu | Thr | Pro | Asp | Asp | Leu | Leu | Asp | Asp | Gly | Glu |
| | 1145 | | | | 1150 | | | | 1155 | | | |

| Ile | Lys | Glu | Asp | Thr | Ser | Phe | Ala | Glu | Asn | Asp | Ile | Lys | Glu | Ser |
| | 1160 | | | | 1165 | | | | 1170 | | | |

| Ser | Ala | Val | Phe | Ser | Lys | Ser | Val | Gln | Lys | Gly | Glu | Leu | Ser | Arg |
| | 1175 | | | | 1180 | | | | 1185 | | | |

| Ser | Pro | Ser | Pro | Phe | Thr | His | Thr | His | Leu | Ala | Gln | Gly | Tyr | Arg |
| | 1190 | | | | 1195 | | | | 1200 | | | |

| Arg | Gly | Ala | Lys | Lys | Leu | Glu | Ser | Ser | Glu | Glu | Asn | Leu | Ser | Ser |
| | 1205 | | | | 1210 | | | | 1215 | | | |

| Glu | Asp | Glu | Glu | Leu | Pro | Cys | Phe | Gln | His | Leu | Leu | Phe | Gly | Lys |
| | 1220 | | | | 1225 | | | | 1230 | | | |

| Val | Asn | Asn | Ile | Pro | Ser | Gln | Ser | Thr | Arg | His | Ser | Thr | Val | Ala |
| | 1235 | | | | 1240 | | | | 1245 | | | |

| Thr | Glu | Cys | Leu | Ser | Lys | Asn | Thr | Glu | Glu | Asn | Leu | Leu | Ser | Leu |
| | 1250 | | | | 1255 | | | | 1260 | | | |

| Lys | Asn | Ser | Leu | Asn | Asp | Cys | Ser | Asn | Gln | Val | Ile | Leu | Ala | Lys |
| | 1265 | | | | 1270 | | | | 1275 | | | |

| Ala | Ser | Gln | Glu | His | His | Leu | Ser | Glu | Glu | Thr | Lys | Cys | Ser | Ala |
| | 1280 | | | | 1285 | | | | 1290 | | | |

| Ser | Leu | Phe | Ser | Ser | Gln | Cys | Ser | Glu | Leu | Glu | Asp | Leu | Thr | Ala |
| | 1295 | | | | 1300 | | | | 1305 | | | |

| Asn | Thr | Asn | Thr | Gln | Asp | Pro | Phe | Leu | Ile | Gly | Ser | Ser | Lys | Gln |
| | 1310 | | | | 1315 | | | | 1320 | | | |

| Met | Arg | His | Gln | Ser | Glu | Ser | Gln | Gly | Val | Gly | Leu | Ser | Asp | Lys |
| | 1325 | | | | 1330 | | | | 1335 | | | |

| Glu | Leu | Val | Ser | Asp | Asp | Glu | Glu | Arg | Gly | Thr | Gly | Leu | Glu | Glu |
| | 1340 | | | | 1345 | | | | 1350 | | | |

| Asn | Asn | Gln | Glu | Glu | Gln | Ser | Met | Asp | Ser | Asn | Leu | Gly | Glu | Ala |
| | 1355 | | | | 1360 | | | | 1365 | | | |

| Ala | Ser | Gly | Cys | Glu | Ser | Glu | Thr | Ser | Val | Ser | Glu | Asp | Cys | Ser |
| | 1370 | | | | 1375 | | | | 1380 | | | |

| Gly | Leu | Ser | Ser | Gln | Ser | Asp | Ile | Leu | Thr | Thr | Gln | Gln | Arg | Asp |
| | 1385 | | | | 1390 | | | | 1395 | | | |

| Thr | Met | Gln | His | Asn | Leu | Ile | Lys | Leu | Gln | Gln | Glu | Met | Ala | Glu |
| | 1400 | | | | 1405 | | | | 1410 | | | |

| Leu | Glu | Ala | Val | Leu | Glu | Gln | His | Gly | Ser | Gln | Pro | Ser | Asn | Ser |
| | 1415 | | | | 1420 | | | | 1425 | | | |

| Tyr | Pro | Ser | Ile | Ile | Ser | Asp | Ser | Ser | Ala | Leu | Glu | Asp | Leu | Arg |
| | 1430 | | | | 1435 | | | | 1440 | | | |

| Asn | Pro | Glu | Gln | Ser | Thr | Ser | Glu | Lys | Ala | Val | Leu | Thr | Ser | Gln |
| | 1445 | | | | 1450 | | | | 1455 | | | |

| Lys | Ser | Ser | Glu | Tyr | Pro | Ile | Ser | Gln | Asn | Pro | Glu | Gly | Leu | Ser |
| | 1460 | | | | 1465 | | | | 1470 | | | |

| Ala | Asp | Lys | Phe | Glu | Val | Ser | Ala | Asp | Ser | Ser | Thr | Ser | Lys | Asn |
| | 1475 | | | | 1480 | | | | 1485 | | | |

| Lys | Glu | Pro | Gly | Val | Glu | Arg | Ser | Ser | Pro | Ser | Lys | Cys | Pro | Ser |

1490                1495                1500

Leu Asp Asp Arg Trp Tyr Met His Ser Cys Ser Gly Ser Leu Gln
    1505                1510                1515

Asn Arg Asn Tyr Pro Ser Gln Glu Leu Ile Lys Val Val Asp
    1520                1525                1530

Val Glu Gln Gln Leu Glu Glu Ser Gly Pro His Asp Leu Thr
    1535                1540                1545

Glu Thr Ser Tyr Leu Pro Arg Gln Asp Leu Glu Gly Thr Pro Tyr
    1550                1555                1560

Leu Glu Ser Gly Ile Ser Leu Phe Ser Asp Asp Pro Glu Ser Asp
    1565                1570                1575

Pro Ser Glu Asp Arg Ala Pro Glu Ser Ala Arg Val Gly Asn Ile
    1580                1585                1590

Pro Ser Ser Thr Ser Ala Leu Lys Val Pro Gln Leu Lys Val Ala
    1595                1600                1605

Glu Ser Ala Gln Ser Pro Ala Ala Ala His Thr Thr Asp Thr Ala
    1610                1615                1620

Gly Tyr Asn Ala Met Glu Glu Ser Val Ser Arg Glu Lys Pro Glu
    1625                1630                1635

Leu Thr Ala Ser Thr Glu Arg Val Asn Lys Arg Met Ser Met Val
    1640                1645                1650

Val Ser Gly Leu Thr Pro Glu Glu Phe Met Leu Val Tyr Lys Phe
    1655                1660                1665

Ala Arg Lys His His Ile Thr Leu Thr Asn Leu Ile Thr Glu Glu
    1670                1675                1680

Thr Thr His Val Val Met Lys Thr Asp Ala Glu Phe Val Cys Glu
    1685                1690                1695

Arg Thr Leu Lys Tyr Phe Leu Gly Ile Ala Gly Gly Lys Trp Val
    1700                1705                1710

Val Ser Tyr Phe Trp Val Thr Gln Ser Ile Lys Glu Arg Lys Met
    1715                1720                1725

Leu Asn Glu His Asp Phe Glu Val Arg Gly Asp Val Val Asn Gly
    1730                1735                1740

Arg Asn His Gln Gly Pro Lys Arg Ala Arg Glu Ser Gln Asp Arg
    1745                1750                1755

Lys Ile Phe Arg Gly Leu Glu Ile Cys Cys Tyr Gly Pro Phe Thr
    1760                1765                1770

Asn Met Pro Thr Asp Gln Leu Glu Trp Met Val Gln Leu Cys Gly
    1775                1780                1785

Ala Ser Val Val Lys Glu Leu Ser Ser Phe Thr Leu Gly Thr Gly
    1790                1795                1800

Val His Pro Ile Val Val Val Gln Pro Asp Ala Trp Thr Glu Asp
    1805                1810                1815

Asn Gly Phe His Ala Ile Gly Gln Met Cys Glu Ala Pro Val Val
    1820                1825                1830

Thr Arg Glu Trp Val Leu Asp Ser Val Ala Leu Tyr Gln Cys Gln
    1835                1840                1845

Glu Leu Asp Thr Tyr Leu Ile Pro Gln Ile Pro His Ser His Tyr
    1850                1855                1860

<210> SEQ ID NO 9
<211> LENGTH: 2442
<212> TYPE: PRT
<213> ORGANISM: Homo sapiens

```
<400> SEQUENCE: 9

Met Ala Glu Asn Leu Leu Asp Gly Pro Pro Asn Pro Lys Arg Ala Lys
1               5                   10                  15

Leu Ser Ser Pro Gly Phe Ser Ala Asn Asp Ser Thr Asp Phe Gly Ser
            20                  25                  30

Leu Phe Asp Leu Glu Asn Asp Leu Pro Asp Glu Leu Ile Pro Asn Gly
        35                  40                  45

Gly Glu Leu Gly Leu Leu Asn Ser Gly Asn Leu Val Pro Asp Ala Ala
    50                  55                  60

Ser Lys His Lys Gln Leu Ser Glu Leu Leu Arg Gly Ser Gly Ser
65                  70                  75                  80

Ser Ile Asn Pro Gly Ile Gly Asn Val Ser Ala Ser Ser Pro Val Gln
                85                  90                  95

Gln Gly Leu Gly Gly Gln Ala Gln Gly Gln Pro Asn Ser Ala Asn Met
            100                 105                 110

Ala Ser Leu Ser Ala Met Gly Lys Ser Pro Leu Ser Gln Gly Asp Ser
            115                 120                 125

Ser Ala Pro Ser Leu Pro Lys Gln Ala Ala Ser Thr Ser Gly Pro Thr
130                 135                 140

Pro Ala Ala Ser Gln Ala Leu Asn Pro Gln Ala Gln Lys Gln Val Gly
145                 150                 155                 160

Leu Ala Thr Ser Ser Pro Ala Thr Ser Gln Thr Gly Pro Gly Ile Cys
                165                 170                 175

Met Asn Ala Asn Phe Asn Gln Thr His Pro Gly Leu Leu Asn Ser Asn
            180                 185                 190

Ser Gly His Ser Leu Ile Asn Gln Ala Ser Gln Gly Gln Ala Gln Val
            195                 200                 205

Met Asn Gly Ser Leu Gly Ala Ala Gly Arg Gly Arg Gly Ala Gly Met
            210                 215                 220

Pro Tyr Pro Thr Pro Ala Met Gln Gly Ala Ser Ser Val Leu Ala
225                 230                 235                 240

Glu Thr Leu Thr Gln Val Ser Pro Gln Met Thr Gly His Ala Gly Leu
                245                 250                 255

Asn Thr Ala Gln Ala Gly Gly Met Ala Lys Met Gly Ile Thr Gly Asn
            260                 265                 270

Thr Ser Pro Phe Gly Gln Pro Phe Ser Gln Ala Gly Gly Gln Pro Met
            275                 280                 285

Gly Ala Thr Gly Val Asn Pro Gln Leu Ala Ser Lys Gln Ser Met Val
    290                 295                 300

Asn Ser Leu Pro Thr Phe Pro Thr Asp Ile Lys Asn Thr Ser Val Thr
305                 310                 315                 320

Asn Val Pro Asn Met Ser Gln Met Gln Thr Ser Val Gly Ile Val Pro
                325                 330                 335

Thr Gln Ala Ile Ala Thr Gly Pro Thr Ala Asp Pro Glu Lys Arg Lys
            340                 345                 350

Leu Ile Gln Gln Gln Leu Val Leu Leu Leu His Ala His Lys Cys Gln
            355                 360                 365

Arg Arg Glu Gln Ala Asn Gly Glu Val Arg Ala Cys Ser Leu Pro His
            370                 375                 380

Cys Arg Thr Met Lys Asn Val Leu Asn His Met Thr His Cys Gln Ala
385                 390                 395                 400

Gly Lys Ala Cys Gln Val Ala His Cys Ala Ser Ser Arg Gln Ile Ile
```

```
                    405                 410                 415
Ser His Trp Lys Asn Cys Thr Arg His Asp Cys Pro Val Cys Leu Pro
            420                 425                 430

Leu Lys Asn Ala Ser Asp Lys Arg Asn Gln Gln Thr Ile Leu Gly Ser
            435                 440                 445

Pro Ala Ser Gly Ile Gln Asn Thr Ile Gly Ser Val Gly Thr Gly Gln
        450                 455                 460

Gln Asn Ala Thr Ser Leu Ser Asn Pro Asn Pro Ile Asp Pro Ser Ser
465                 470                 475                 480

Met Gln Arg Ala Tyr Ala Ala Leu Gly Leu Pro Tyr Met Asn Gln Pro
                485                 490                 495

Gln Thr Gln Leu Gln Pro Gln Val Pro Gly Gln Gln Pro Ala Gln Pro
            500                 505                 510

Gln Thr His Gln Gln Met Arg Thr Leu Asn Pro Leu Gly Asn Asn Pro
            515                 520                 525

Met Asn Ile Pro Ala Gly Gly Ile Thr Thr Asp Gln Gln Pro Pro Asn
        530                 535                 540

Leu Ile Ser Glu Ser Ala Leu Pro Thr Ser Leu Gly Ala Thr Asn Pro
545                 550                 555                 560

Leu Met Asn Asp Gly Ser Asn Ser Gly Asn Ile Gly Thr Leu Ser Thr
                565                 570                 575

Ile Pro Thr Ala Ala Pro Pro Ser Ser Thr Gly Val Arg Lys Gly Trp
            580                 585                 590

His Glu His Val Thr Gln Asp Leu Arg Ser His Leu Val His Lys Leu
            595                 600                 605

Val Gln Ala Ile Phe Pro Thr Pro Asp Pro Ala Ala Leu Lys Asp Arg
        610                 615                 620

Arg Met Glu Asn Leu Val Ala Tyr Ala Lys Lys Val Glu Gly Asp Met
625                 630                 635                 640

Tyr Glu Ser Ala Asn Ser Arg Asp Glu Tyr Tyr His Leu Leu Ala Glu
                645                 650                 655

Lys Ile Tyr Lys Ile Gln Lys Glu Leu Glu Glu Lys Arg Arg Ser Arg
            660                 665                 670

Leu His Lys Gln Gly Ile Leu Gly Asn Gln Pro Ala Leu Pro Ala Pro
            675                 680                 685

Gly Ala Gln Pro Pro Val Ile Pro Gln Ala Gln Pro Val Arg Pro Pro
        690                 695                 700

Asn Gly Pro Leu Ser Leu Pro Val Asn Arg Met Gln Val Ser Gln Gly
705                 710                 715                 720

Met Asn Ser Phe Asn Pro Met Ser Leu Gly Asn Val Gln Leu Pro Gln
                725                 730                 735

Ala Pro Met Gly Pro Arg Ala Ala Ser Pro Met Asn His Ser Val Gln
            740                 745                 750

Met Asn Ser Met Gly Ser Val Pro Gly Met Ala Ile Ser Pro Ser Arg
            755                 760                 765

Met Pro Gln Pro Pro Asn Met Met Gly Ala His Thr Asn Asn Met Met
        770                 775                 780

Ala Gln Ala Pro Ala Gln Ser Gln Phe Leu Pro Gln Asn Gln Phe Pro
785                 790                 795                 800

Ser Ser Ser Gly Ala Met Ser Val Gly Met Gly Gln Pro Pro Ala Gln
                805                 810                 815

Thr Gly Val Ser Gln Gly Gln Val Pro Gly Ala Ala Leu Pro Asn Pro
            820                 825                 830
```

```
Leu Asn Met Leu Gly Pro Gln Ala Ser Gln Leu Pro Cys Pro Pro Val
        835                 840                 845

Thr Gln Ser Pro Leu His Pro Thr Pro Pro Ala Ser Thr Ala Ala
850                 855                 860

Gly Met Pro Ser Leu Gln His Thr Thr Pro Pro Gly Met Thr Pro Pro
865                 870                 875                 880

Gln Pro Ala Ala Pro Thr Gln Pro Ser Thr Pro Val Ser Ser Ser Gly
                885                 890                 895

Gln Thr Pro Thr Pro Thr Pro Gly Ser Val Pro Ser Ala Thr Gln Thr
                900                 905                 910

Gln Ser Thr Pro Thr Val Gln Ala Ala Gln Ala Gln Val Thr Pro
        915                 920                 925

Gln Pro Gln Thr Pro Val Gln Pro Pro Ser Val Ala Thr Pro Gln Ser
        930                 935                 940

Ser Gln Gln Gln Pro Thr Pro Val His Ala Gln Pro Pro Gly Thr Pro
945                 950                 955                 960

Leu Ser Gln Ala Ala Ala Ser Ile Asp Asn Arg Val Pro Thr Pro Ser
                965                 970                 975

Ser Val Ala Ser Ala Glu Thr Asn Ser Gln Gln Pro Gly Pro Asp Val
                980                 985                 990

Pro Val Leu Glu Met Lys Thr Glu Thr Gln Ala Glu Asp Thr Glu Pro
                995                 1000                1005

Asp Pro Gly Glu Ser Lys Gly Glu Pro Arg Ser Glu Met Met Glu
    1010                1015                1020

Glu Asp Leu Gln Gly Ala Ser Gln Val Lys Glu Glu Thr Asp Ile
    1025                1030                1035

Ala Glu Gln Lys Ser Glu Pro Met Glu Val Asp Glu Lys Lys Pro
    1040                1045                1050

Glu Val Lys Val Glu Val Lys Glu Glu Glu Glu Ser Ser Ser Asn
    1055                1060                1065

Gly Thr Ala Ser Gln Ser Thr Ser Pro Ser Gln Pro Arg Lys Lys
    1070                1075                1080

Ile Phe Lys Pro Glu Glu Leu Arg Gln Ala Leu Met Pro Thr Leu
    1085                1090                1095

Glu Ala Leu Tyr Arg Gln Asp Pro Glu Ser Leu Pro Phe Arg Gln
    1100                1105                1110

Pro Val Asp Pro Gln Leu Leu Gly Ile Pro Asp Tyr Phe Asp Ile
    1115                1120                1125

Val Lys Asn Pro Met Asp Leu Ser Thr Ile Lys Arg Lys Leu Asp
    1130                1135                1140

Thr Gly Gln Tyr Gln Glu Pro Trp Gln Tyr Val Asp Asp Val Trp
    1145                1150                1155

Leu Met Phe Asn Asn Ala Trp Leu Tyr Asn Arg Lys Thr Ser Arg
    1160                1165                1170

Val Tyr Lys Phe Cys Ser Lys Leu Ala Glu Val Phe Glu Gln Glu
    1175                1180                1185

Ile Asp Pro Val Met Gln Ser Leu Gly Tyr Cys Cys Gly Arg Lys
    1190                1195                1200

Tyr Glu Phe Ser Pro Gln Thr Leu Cys Cys Tyr Gly Lys Gln Leu
    1205                1210                1215

Cys Thr Ile Pro Arg Asp Ala Ala Tyr Tyr Ser Tyr Gln Asn Arg
    1220                1225                1230
```

```
Tyr His Phe Cys Glu Lys Cys Phe Thr Glu Ile Gln Gly Glu Asn
1235                1240                1245

Val Thr Leu Gly Asp Asp Pro Ser Gln Pro Gln Thr Thr Ile Ser
1250                1255                1260

Lys Asp Gln Phe Glu Lys Lys Lys Asn Asp Thr Leu Asp Pro Glu
1265                1270                1275

Pro Phe Val Asp Cys Lys Glu Cys Gly Arg Lys Met His Gln Ile
1280                1285                1290

Cys Val Leu His Tyr Asp Ile Ile Trp Pro Ser Gly Phe Val Cys
1295                1300                1305

Asp Asn Cys Leu Lys Lys Thr Gly Arg Pro Arg Lys Glu Asn Lys
1310                1315                1320

Phe Ser Ala Lys Arg Leu Gln Thr Thr Arg Leu Gly Asn His Leu
1325                1330                1335

Glu Asp Arg Val Asn Lys Phe Leu Arg Arg Gln Asn His Pro Glu
1340                1345                1350

Ala Gly Glu Val Phe Val Arg Val Val Ala Ser Ser Asp Lys Thr
1355                1360                1365

Val Glu Val Lys Pro Gly Met Lys Ser Arg Phe Val Asp Ser Gly
1370                1375                1380

Glu Met Ser Glu Ser Phe Pro Tyr Arg Thr Lys Ala Leu Phe Ala
1385                1390                1395

Phe Glu Glu Ile Asp Gly Val Asp Val Cys Phe Phe Gly Met His
1400                1405                1410

Val Gln Glu Tyr Gly Ser Asp Cys Pro Pro Pro Asn Thr Arg Arg
1415                1420                1425

Val Tyr Ile Ser Tyr Leu Asp Ser Ile His Phe Phe Arg Pro Arg
1430                1435                1440

Cys Leu Arg Thr Ala Val Tyr His Glu Ile Leu Ile Gly Tyr Leu
1445                1450                1455

Glu Tyr Val Lys Lys Leu Gly Tyr Val Thr Gly His Ile Trp Ala
1460                1465                1470

Cys Pro Pro Ser Glu Gly Asp Asp Tyr Ile Phe His Cys His Pro
1475                1480                1485

Pro Asp Gln Lys Ile Pro Lys Pro Lys Arg Leu Gln Glu Trp Tyr
1490                1495                1500

Lys Lys Met Leu Asp Lys Ala Phe Ala Glu Arg Ile Ile His Asp
1505                1510                1515

Tyr Lys Asp Ile Phe Lys Gln Ala Thr Glu Asp Arg Leu Thr Ser
1520                1525                1530

Ala Lys Glu Leu Pro Tyr Phe Glu Gly Asp Phe Trp Pro Asn Val
1535                1540                1545

Leu Glu Glu Ser Ile Lys Glu Leu Glu Gln Glu Glu Glu Glu Arg
1550                1555                1560

Lys Lys Glu Glu Ser Thr Ala Ala Ser Glu Thr Thr Glu Gly Ser
1565                1570                1575

Gln Gly Asp Ser Lys Asn Ala Lys Lys Lys Asn Lys Lys Lys Thr
1580                1585                1590

Asn Lys Asn Lys Ser Ser Ile Ser Arg Ala Asn Lys Lys Lys Pro
1595                1600                1605

Ser Met Pro Asn Val Ser Asn Asp Leu Ser Gln Lys Leu Tyr Ala
1610                1615                1620

Thr Met Glu Lys His Lys Glu Val Phe Phe Val Ile His Leu His
```

```
              1625                1630                1635
Ala Gly Pro Val Ile Asn Thr Leu Pro Pro Ile Val Asp Pro Asp
              1640                1645                1650

Pro Leu Leu Ser Cys Asp Leu Met Asp Gly Arg Asp Ala Phe Leu
              1655                1660                1665

Thr Leu Ala Arg Asp Lys His Trp Glu Phe Ser Ser Leu Arg Arg
              1670                1675                1680

Ser Lys Trp Ser Thr Leu Cys Met Leu Val Glu Leu His Thr Gln
              1685                1690                1695

Gly Gln Asp Arg Phe Val Tyr Thr Cys Asn Glu Cys Lys His His
              1700                1705                1710

Val Glu Thr Arg Trp His Cys Thr Val Cys Glu Asp Tyr Asp Leu
              1715                1720                1725

Cys Ile Asn Cys Tyr Asn Thr Lys Ser His Ala His Lys Met Val
              1730                1735                1740

Lys Trp Gly Leu Gly Leu Asp Asp Glu Gly Ser Ser Gln Gly Glu
              1745                1750                1755

Pro Gln Ser Lys Ser Pro Gln Glu Ser Arg Arg Leu Ser Ile Gln
              1760                1765                1770

Arg Cys Ile Gln Ser Leu Val His Ala Cys Gln Cys Arg Asn Ala
              1775                1780                1785

Asn Cys Ser Leu Pro Ser Cys Gln Lys Met Lys Arg Val Val Gln
              1790                1795                1800

His Thr Lys Gly Cys Lys Arg Lys Thr Asn Gly Gly Cys Pro Val
              1805                1810                1815

Cys Lys Gln Leu Ile Ala Leu Cys Cys Tyr His Ala Lys His Cys
              1820                1825                1830

Gln Glu Asn Lys Cys Pro Val Pro Phe Cys Leu Asn Ile Lys His
              1835                1840                1845

Lys Leu Arg Gln Gln Gln Ile Gln His Arg Leu Gln Gln Ala Gln
              1850                1855                1860

Leu Met Arg Arg Arg Met Ala Thr Met Asn Thr Arg Asn Val Pro
              1865                1870                1875

Gln Gln Ser Leu Pro Ser Pro Thr Ser Ala Pro Pro Gly Thr Pro
              1880                1885                1890

Thr Gln Gln Pro Ser Thr Pro Gln Thr Pro Gln Pro Pro Ala Gln
              1895                1900                1905

Pro Gln Pro Ser Pro Val Ser Met Ser Pro Ala Gly Phe Pro Ser
              1910                1915                1920

Val Ala Arg Thr Gln Pro Pro Thr Thr Val Ser Thr Gly Lys Pro
              1925                1930                1935

Thr Ser Gln Val Pro Ala Pro Pro Pro Pro Ala Gln Pro Pro Pro
              1940                1945                1950

Ala Ala Val Glu Ala Ala Arg Gln Ile Glu Arg Glu Ala Gln Gln
              1955                1960                1965

Gln Gln His Leu Tyr Arg Val Asn Ile Asn Asn Ser Met Pro Pro
              1970                1975                1980

Gly Arg Thr Gly Met Gly Thr Pro Gly Ser Gln Met Ala Pro Val
              1985                1990                1995

Ser Leu Asn Val Pro Arg Pro Asn Gln Val Ser Gly Pro Val Met
              2000                2005                2010

Pro Ser Met Pro Pro Gly Gln Trp Gln Gln Ala Pro Leu Pro Gln
              2015                2020                2025
```

```
Gln Gln Pro Met Pro Gly Leu Pro Arg Pro Val Ile Ser Met Gln
    2030            2035            2040

Ala Gln Ala Ala Val Ala Gly Pro Arg Met Pro Ser Val Gln Pro
    2045            2050            2055

Pro Arg Ser Ile Ser Pro Ser Ala Leu Gln Asp Leu Leu Arg Thr
    2060            2065            2070

Leu Lys Ser Pro Ser Ser Pro Gln Gln Gln Gln Gln Val Leu Asn
    2075            2080            2085

Ile Leu Lys Ser Asn Pro Gln Leu Met Ala Ala Phe Ile Lys Gln
    2090            2095            2100

Arg Thr Ala Lys Tyr Val Ala Asn Gln Pro Gly Met Gln Pro Gln
    2105            2110            2115

Pro Gly Leu Gln Ser Gln Pro Gly Met Gln Pro Gln Pro Gly Met
    2120            2125            2130

His Gln Gln Pro Ser Leu Gln Asn Leu Asn Ala Met Gln Ala Gly
    2135            2140            2145

Val Pro Arg Pro Gly Val Pro Pro Gln Gln Gln Ala Met Gly Gly
    2150            2155            2160

Leu Asn Pro Gln Gly Gln Ala Leu Asn Ile Met Asn Pro Gly His
    2165            2170            2175

Asn Pro Asn Met Ala Ser Met Asn Pro Gln Tyr Arg Glu Met Leu
    2180            2185            2190

Arg Arg Gln Leu Leu Gln Gln Gln Gln Gln Gln Gln Gln Gln Gln
    2195            2200            2205

Gln Gln Gln Gln Gln Gln Gln Gly Ser Ala Gly Met Ala Gly
    2210            2215            2220

Gly Met Ala Gly His Gly Gln Phe Gln Gln Pro Gln Gly Pro Gly
    2225            2230            2235

Gly Tyr Pro Pro Ala Met Gln Gln Gln Arg Met Gln Gln His
    2240            2245            2250

Leu Pro Leu Gln Gly Ser Ser Met Gly Gln Met Ala Ala Gln Met
    2255            2260            2265

Gly Gln Leu Gly Gln Met Gly Gln Pro Gly Leu Gly Ala Asp Ser
    2270            2275            2280

Thr Pro Asn Ile Gln Gln Ala Leu Gln Gln Arg Ile Leu Gln Gln
    2285            2290            2295

Gln Gln Met Lys Gln Gln Ile Gly Ser Pro Gly Gln Pro Asn Pro
    2300            2305            2310

Met Ser Pro Gln Gln His Met Leu Ser Gly Gln Pro Gln Ala Ser
    2315            2320            2325

His Leu Pro Gly Gln Gln Ile Ala Thr Ser Leu Ser Asn Gln Val
    2330            2335            2340

Arg Ser Pro Ala Pro Val Gln Ser Pro Arg Pro Gln Ser Gln Pro
    2345            2350            2355

Pro His Ser Ser Pro Ser Pro Arg Ile Gln Pro Gln Pro Ser Pro
    2360            2365            2370

His His Val Ser Pro Gln Thr Gly Ser Pro His Pro Gly Leu Ala
    2375            2380            2385

Val Thr Met Ala Ser Ser Ile Asp Gln Gly His Leu Gly Asn Pro
    2390            2395            2400

Glu Gln Ser Ala Met Leu Pro Gln Leu Asn Thr Pro Ser Arg Ser
    2405            2410            2415
```

Ala Leu Ser Ser Glu Leu Ser Leu Val Gly Asp Thr Thr Gly Asp
    2420                2425                    2430

Thr Leu Glu Lys Phe Val Glu Gly Leu
    2435                2440

<210> SEQ ID NO 10
<211> LENGTH: 385
<212> TYPE: PRT
<213> ORGANISM: Homo sapiens

<400> SEQUENCE: 10

Met Met Met Met Ala Leu Ser Lys Thr Phe Gly Gln Lys Pro Val Lys
1               5                   10                  15

Phe Gln Leu Glu Asp Asp Gly Glu Phe Tyr Met Ile Gly Ser Glu Val
                20                  25                  30

Gly Asn Tyr Leu Arg Met Phe Arg Gly Ser Leu Tyr Lys Arg Tyr Pro
            35                  40                  45

Ser Leu Trp Arg Arg Leu Ala Thr Val Glu Glu Arg Lys Lys Ile Val
50                  55                  60

Ala Ser Ser His Gly Lys Lys Thr Lys Pro Asn Thr Lys Asp His Gly
65                  70                  75                  80

Tyr Thr Thr Leu Ala Thr Ser Val Thr Leu Leu Lys Ala Ser Glu Val
                85                  90                  95

Glu Glu Ile Leu Asp Gly Asn Asp Glu Lys Tyr Lys Ala Val Ser Ile
                100                 105                 110

Ser Thr Glu Pro Pro Thr Tyr Leu Arg Glu Gln Lys Ala Lys Arg Asn
            115                 120                 125

Ser Gln Trp Val Pro Thr Leu Pro Asn Ser Ser His His Leu Asp Ala
130                 135                 140

Val Pro Cys Ser Thr Thr Ile Asn Arg Asn Arg Met Gly Arg Asp Lys
145                 150                 155                 160

Lys Arg Thr Phe Pro Leu Cys Phe Asp Asp His Asp Pro Ala Val Ile
                165                 170                 175

His Glu Asn Ala Ser Gln Pro Glu Val Leu Val Pro Ile Arg Leu Asp
                180                 185                 190

Met Glu Ile Asp Gly Gln Lys Leu Arg Asp Ala Phe Thr Trp Asn Met
            195                 200                 205

Asn Glu Lys Leu Met Thr Pro Glu Met Phe Ser Glu Ile Leu Cys Asp
210                 215                 220

Asp Leu Asp Leu Asn Pro Leu Thr Phe Val Pro Ala Ile Ala Ser Ala
225                 230                 235                 240

Ile Arg Gln Gln Ile Glu Ser Tyr Pro Thr Asp Ser Ile Leu Glu Asp
                245                 250                 255

Gln Ser Asp Gln Arg Val Ile Ile Lys Leu Asn Ile His Val Gly Asn
            260                 265                 270

Ile Ser Leu Val Asp Gln Phe Glu Trp Asp Met Ser Glu Lys Glu Asn
        275                 280                 285

Ser Pro Glu Lys Phe Ala Leu Lys Leu Cys Ser Glu Leu Gly Leu Gly
290                 295                 300

Gly Glu Phe Val Thr Thr Ile Ala Tyr Ser Ile Arg Gly Gln Leu Ser
305                 310                 315                 320

Trp His Gln Lys Thr Tyr Ala Phe Ser Glu Asn Pro Leu Pro Thr Val
                325                 330                 335

Glu Ile Ala Ile Arg Asn Thr Gly Asp Ala Asp Gln Trp Cys Pro Leu
                340                 345                 350

```
Leu Glu Thr Leu Thr Asp Ala Glu Met Glu Lys Lys Ile Arg Asp Gln
            355                 360                 365

Asp Arg Asn Thr Arg Arg Met Arg Arg Leu Ala Asn Thr Ala Pro Ala
    370                 375                 380

Trp
385

<210> SEQ ID NO 11
<211> LENGTH: 381
<212> TYPE: PRT
<213> ORGANISM: Homo sapiens

<400> SEQUENCE: 11

Met Glu Ser Gly Ser Thr Ala Ala Ser Glu Glu Ala Arg Ser Leu Arg
1               5                   10                  15

Glu Cys Glu Leu Tyr Val Gln Lys His Asn Ile Gln Ala Leu Leu Lys
                20                  25                  30

Asp Ser Ile Val Gln Leu Cys Thr Ala Arg Pro Glu Arg Pro Met Ala
            35                  40                  45

Phe Leu Arg Glu Tyr Phe Glu Arg Leu Glu Lys Glu Glu Ala Lys Gln
    50                  55                  60

Ile Gln Asn Leu Gln Lys Ala Gly Thr Arg Thr Asp Ser Arg Glu Asp
65              70                  75                  80

Glu Ile Ser Pro Pro Pro Asn Pro Val Lys Gly Arg Arg Arg
                85                  90                  95

Arg Gly Ala Ile Ser Ala Glu Val Tyr Thr Glu Glu Asp Ala Ala Ser
                100                 105                 110

Tyr Val Arg Lys Val Ile Pro Lys Asp Tyr Lys Thr Met Ala Ala Leu
            115                 120                 125

Ala Lys Ala Ile Glu Lys Asn Val Leu Phe Ser His Leu Asp Asp Asn
130                 135                 140

Glu Arg Ser Asp Ile Phe Asp Ala Met Phe Ser Val Ser Phe Ile Ala
145                 150                 155                 160

Gly Glu Thr Val Ile Gln Gln Gly Asp Glu Gly Asp Asn Phe Tyr Val
                165                 170                 175

Ile Asp Gln Gly Glu Thr Asp Val Tyr Val Asn Asn Glu Trp Ala Thr
            180                 185                 190

Ser Val Gly Glu Gly Gly Ser Phe Gly Glu Leu Ala Leu Ile Tyr Gly
        195                 200                 205

Thr Pro Arg Ala Ala Thr Val Lys Ala Lys Thr Asn Val Lys Leu Trp
210                 215                 220

Gly Ile Asp Arg Asp Ser Tyr Arg Arg Ile Leu Met Gly Ser Thr Leu
225                 230                 235                 240

Arg Lys Arg Lys Met Tyr Glu Glu Phe Leu Ser Lys Val Ser Ile Leu
                245                 250                 255

Glu Ser Leu Asp Lys Trp Glu Arg Leu Thr Val Ala Asp Ala Leu Glu
            260                 265                 270

Pro Val Gln Phe Glu Asp Gly Gln Lys Ile Val Val Gln Gly Glu Pro
        275                 280                 285

Gly Asp Glu Phe Phe Ile Ile Leu Glu Gly Ser Ala Ala Val Leu Gln
        290                 295                 300

Arg Arg Ser Glu Asn Glu Glu Phe Val Glu Val Gly Arg Leu Gly Pro
305                 310                 315                 320

Ser Asp Tyr Phe Gly Glu Ile Ala Leu Leu Met Asn Arg Pro Arg Ala
```

-continued

```
                325                 330                 335
Ala Thr Val Val Ala Arg Gly Pro Leu Lys Cys Val Lys Leu Asp Arg
            340                 345                 350

Pro Arg Phe Glu Arg Val Leu Gly Pro Cys Ser Asp Ile Leu Lys Arg
        355                 360                 365

Asn Ile Gln Gln Tyr Asn Ser Phe Val Ser Leu Ser Val
    370                 375                 380
```

COMPOSITIONS AND METHODS FOR DIAGNOSING AND TREATING MENINGIOMA

CROSS-REFERENCE TO RELATED APPLICATION

This application is a U.S. national phase application filed under 35 U.S.C. 371 claiming priority to International Patent Application No. PCT/US2013/032311, filed on Mar. 15, 2013, which claims priority from U.S. Provisional App. Ser. No. 61/621,758, filed Apr. 9, 2012, and U.S. Provisional App. Ser. No. 61/755,796, filed Jan. 23, 2013, which are hereby incorporated by reference in their entireties herein.

BACKGROUND OF THE INVENTION

While considerable attention has been paid to the genomic analysis of malignant tumors, benign tumors are much less studied. Meningiomas, arising from the meninges of the central nervous system, are the most common primary brain tumors, with a prevalence of ~170,000 cases in the US (Wiemels et al., 2010, J Neurooncol, 99:307). While 90% are histologically classified as benign, meningiomas frequently invade surrounding brain and critical neurovascular structures, often causing neurological deficits. Symptomatic patients require surgical intervention or radiotherapy, as there are no established chemotherapeutic targets. Moreover, approximately 10% of meningiomas represent atypical (Grade II) or anaplastic (Grade III) forms, and are associated with increased symptom severity and greater recurrence risk. The risk factors for meningioma formation, other than female gender, increasing age and ionizing radiation exposure, are unknown. Similarly, other than loss of chromosome 22 and NF2 coding mutations, observed in 40-60% of sporadic meningiomas (Riemenschneider et al., 2006, Lancet neurology, 5:1045), the genetic architecture remains obscure, limiting options for the development of rational therapies.

Thus, there is a need in the art for compositions and methods of diagnosing meningiomas and assessing the risk for developing meningiomas. The present invention satisfies this unmet need.

SUMMARY

The present invention relates to the discovery that particular mutations are associated with neoplasia, such as meningioma. Thus, the invention relates to compositions and methods useful for the assessment, characterization, classification and treatment of neoplasia, including meningioma, based upon the presence or absence of particular mutations that are associated with neoplasia, including meningioma.

In one embodiment, the invention is a method of identifying a mutation in a gene associated with neoplasia in a subject in need thereof, including the steps of obtaining a test sample from the subject, wherein the test sample comprises a nucleic acid comprising at least one gene, or fragment thereof, associated with neoplasia; determining the sequence of the nucleic acid comprising the at least one gene, or fragment thereof, associated with neoplasia in the test sample; comparing the sequence of the nucleic acid comprising the at least one gene, or fragment thereof, associated with neoplasia in the test sample with the sequence of at least one mutation of a gene associated with neoplasia, wherein when the sequence of the nucleic acid comprising the at least one gene, or fragment thereof, associated with neoplasia in the test sample is homologous to the sequence of the at least one mutation of the gene associated with neoplasia, the mutation in the gene associated with neoplasia in the subject is identified. In some embodiments, the least one gene associated with neoplasia is at least one gene selected from the group consisting of NF2, TRAF7, AKT1, KLF4, SMO, PIK3CA, PIK3R1, BRCA1, CREBBP, SMARCB1 and PRKAR1A. In some embodiments, the at least one mutation of the gene associated with neoplasia encodes an amino acid having at least one mutation selected from the group consisting of NF2 Q453X, NF2 F256fs, NF2 T59fs, NF2 Q65fs, NF2 E460X, NF2 K17_M29del, NF2 A21 Ifs, NF2 Q459X, NF2 363+1G>C, NF2 K99fs, NF2 G43fs, NF2 K44X, NF2 K15fs, NF2 Y207fs, NF2 115-1G>A, NF2 Q319X, NF2 Ll4fs, NF2 M426fs, NF2 L208P, NF2 N104fs, NF2 R25fs, NF2 R262X, TRAF7 C388Y, TRAF7 R641C, TRAF7 Q637H, TRAF7 K615E, TRAF7 L580del, TRAF7 R641C, TRAF7 G536S, TRAF7 N520S, TRAF7 S561N, TRAF7 G390E, TRAF7 R653Q, TRAF7 E353insFRRDAS, TRAF7 T145M, TRAF7 F337S, AKT1 E17K, KLF4 K409Q, SMO L412F, SMO W535L, PIK3CA R108H, PIK3R1 del306-307, PRKAR1A A213D. In one embodiment, the test sample of the subject comprises genomic DNA. In some embodiments, the method includes the step of determining whether chromosome 22 is present in the test sample of the subject. In some embodiments, the neoplasia is meningioma. In one embodiment, the subject is a human. In some embodiments, determining the sequence of the nucleic acid comprises at least one of the group consisting of PCR, Northern analysis, Southern analysis, DNA array analysis, and direct sequence analysis.

In another embodiment, the invention is a method of diagnosing neoplasia in a subject in need thereof, including the steps of obtaining a test sample from the subject, wherein the test sample comprises a nucleic acid comprising at least one gene, or fragment thereof, associated with neoplasia; determining the sequence of the nucleic acid comprising the at least one gene, or fragment thereof, associated with neoplasia in the test sample; comparing the sequence of the nucleic acid comprising the at least one gene, or fragment thereof, associated with neoplasia in the test sample with the sequence of at least one mutation of a gene associated with neoplasia, wherein when the sequence of the nucleic acid comprising the at least one gene, or fragment thereof, associated with neoplasia in the test sample is homologous to the sequence of the at least one mutation of the gene associated with neoplasia, the subject is diagnosed with neoplasia. In some embodiments, the at least one gene associated with neoplasia is at least one gene selected from the group consisting of NF2, TRAF7, AKT1, KLF4, SMO, PIK3CA, PIK3R1, BRCA1, CREBBP, SMARCB1 and PRKAR1A. In some embodiments, the at least one mutation of the gene associated with neoplasia encodes an amino acid having at least one mutation selected from the group consisting of NF2 Q453X, NF2 F256fs, NF2 T59fs, NF2 Q65fs, NF2 E460X, NF2 K17_M29del, NF2 A21 Ifs, NF2 Q459X, NF2 363+1G>C, NF2 K99fs, NF2 G43fs, NF2 K44X, NF2 K15fs, NF2 Y207fs, NF2 115-1G>A, NF2 Q319X, NF2 L14fs, NF2 M426fs, NF2 L208P, NF2 N104fs, NF2 R25fs, NF2 R262X, TRAF7 C388Y, TRAF7 R641C, TRAF7 Q637H, TRAF7 K615E, TRAF7 L580del, TRAF7 R641C, TRAF7 G536S, TRAF7 N520S, TRAF7 S561N, TRAF7 G390E, TRAF7 R653Q, TRAF7 E353insFRRDAS, TRAF7 T145M, TRAF7 F337S, AKT1 E17K, KLF4 K409Q, SMO L412F, SMO W535L, PIK3CA R108H, PIK3R1 del306-307 and PRKAR1A A213D. In one embodiment, the test sample of the subject comprises genomic DNA. In some embodiments, the method includes the step of determining whether chromosome 22 is present in the test sample of the subject, wherein the presence or absence of chromosome 22 aides in the classification of neoplasia. In some embodiments, the neoplasia is meningioma. In one embodiment, the subject is a human. In some embodiments, determining the sequence of the nucleic acid comprises at least one of the group consisting of PCR, Northern analysis, Southern analysis, DNA array analysis, and direct sequence analysis.

In another embodiment, the invention is a method of identifying the type of meningioma present in a subject, including the steps of obtaining a test sample from the subject, wherein the test sample comprises a nucleic acid comprising at least one gene, or fragment thereof, associated with meningioma; determining the sequence of the nucleic acid comprising the at least one gene, or fragment thereof, associated with meningioma in the test sample; comparing the sequence of the nucleic acid comprising the at least one gene, or fragment thereof, associated with meningioma in the test sample with the sequence of at least one mutation of a gene associated with meningioma, wherein when the sequence of the nucleic acid comprising the at least one gene, or fragment thereof, associated with meningioma in the test sample is homologous to the sequence of the at least one mutation of the gene associated with meningioma, the type of meningioma present in the subject is identified. In some embodiments, the at least one gene associated with meningioma is at least one gene selected from the group consisting of NF2, TRAF7, AKT1, KLF4, SMO, PIK3CA, PIK3R1, BRCA1, CREBBP, SMARCB1 and PRKAR1A. In some embodiments, the at least one mutation of the gene associated with meningioma encodes an amino acid having at least one mutation selected from the group consisting of NF2 Q453X, NF2 F256fs, NF2 T59fs, NF2 Q65fs, NF2 E460X, NF2 K17_M29del, NF2 A211fs, NF2 Q459X, NF2 363+1G>C, NF2 K99fs, NF2 G43fs, NF2 K44X, NF2 K15fs, NF2 Y207fs, NF2 115-IG>A, NF2 Q319X, NF2 L14fs, NF2 M426fs, NF2 L208P, NF2 N104fs, NF2 R25fs, NF2 R262X, TRAF7 C388Y, TRAF7 R641C, TRAF7 Q637H, TRAF7 K615E, TRAF7 L580del, TRAF7 R641C, TRAF7 G536S, TRAF7 N520S, TRAF7 S561N, TRAF7 G390E, TRAF7 R653Q, TRAF7 E353insFRRDAS, TRAF7 T145M, TRAF7 F337S, AKT1 E17K, KLF4 K409Q, SMO L412F, SMO W535L, PIK3CA R108H, PIK3R1 del306-307 and PRKAR1A A213D. In one embodiment, the test sample of the subject comprises genomic DNA. In some embodiments, the method includes the step of determining whether chromosome 22 is present in the test sample of the subject, wherein the presence or absence of chromosome 22 aides in identifying the type of meningioma. In some embodiments, the type of meningioma is at one selected from the group consisting of grade I, grade II and grade III. In one embodiment, the subject is a human. In some embodiments, determining the sequence of the nucleic acid comprises at least one of the group consisting of PCR, Northern analysis, Southern analysis, DNA array analysis, and direct sequence analysis.

In another embodiment, the invention is a method of determining the appropriate neoplasia treatment regimen to administer to a subject in need thereof, including the steps of obtaining a test sample from the subject, wherein the test sample comprises a nucleic acid comprising at least one gene, or fragment thereof, associated with neoplasia; determining the sequence of the nucleic acid comprising the at least one gene, or fragment thereof, associated with neoplasia in the test sample; comparing the sequence of the nucleic acid comprising the at least one gene, or fragment thereof, associated with neoplasia in the test sample with the sequence of at least one mutation of a gene associated with neoplasia, wherein when the sequence of the nucleic acid comprising the at least one gene, or fragment thereof, associated with neoplasia in the test sample is homologous to the sequence of the at least one mutation of the gene associated with neoplasia, the at least one mutation of a gene associated with neoplasia in the patient is identified and the appropriate neoplasia treatment regimen to administer to the subject is determined. In some embodiments, the at least one gene associated with neoplasia is at least one gene selected from the group consisting of NF2, TRAF7, AKT1, KLF4, SMO, PIK3CA, PIK3R1, BRCA1, CREBBP, SMARCB1 and PRKAR1A. In some embodiments, the at least one mutation of the gene associated with neoplasia encodes an amino acid having at least one mutation selected from the group consisting of NF2 Q453X, NF2 F256fs, NF2 T59fs, NF2 Q65fs, NF2 E460X, NF2 K17_M29del, NF2 A21 fs, NF2 Q459X, NF2 363+1G>C, NF2 K99fs, NF2 G43fs, NF2 K44X, NF2 K15fs, NF2 Y207fs, NF2 115-1G>A, NF2 Q319X, NF2 L14fs, NF2 M426fs, NF2 L208P, NF2 N104fs, NF2 R25fs, NF2 R262X, TRAF7 C388Y, TRAF7 R641C, TRAF7 Q637H, TRAF7 K615E, TRAF7 L580del, TRAF7 R641C, TRAF7 G536S, TRAF7 N520S, TRAF7 S561N, TRAF7 G390E, TRAF7 R653Q, TRAF7 E353insFRRDAS, TRAF7 T145M, TRAF7 F337S, AKT1 E17K, KLF4 K409Q, SMO L412F, SMO W535L, PIK3CA R108H, PIK3R1 del306-307 and PRKAR1A A213D. In one embodiment, the test sample of the subject comprises genomic DNA. In some embodiments, the method includes the step of determining whether chromosome 22 is present in the test sample of the subject, wherein the presence or absence of chromosome 22 aides in determining the appropriate neoplasia treatment regimen to administer. In one embodiment, the neoplasia is meningioma. In one embodiment, the subject is a human. In some embodiments, determining the sequence of the nucleic acid comprises at least one of the group consisting of PCR, Northern analysis, Southern analysis, DNA array analysis, and direct sequence analysis.

In another embodiment, the invention is a method of treating or preventing neoplasia in a subject in need thereof, including the steps of administering to the subject, a therapeutically effective amount of an inhibitor of a mutant gene, or mutant gene product, associated with neoplasia, wherein the subject has been diagnosed as having neoplasia, and wherein after the inhibitor is administered to the subject, the neoplasia is treated or prevented. In various embodiments, the inhibitor of the mutant gene, or mutant gene product, is at least one selected from the group consisting of a chemical compound, a protein, a peptide, a peptidomemetic, an antibody, a ribozyme, a small molecule chemical compound, and an antisense nucleic acid molecule. In some embodiments, the mutant gene, or mutant gene product, at least one gene selected from the group consisting of mutant NF2, mutant TRAF7, mutant AKT1, mutant KLF4, mutant SMO, mutant PIK3CA, mutant PIK3R1, mutant BRCA1, mutant CREBBP, mutant SMARCB1 and mutant PRKAR1A. In some embodiments, the mutant gene, or mutant gene product, is a nucleic acid encoding an amino acid having at least one mutation selected from the group consisting of NF2 Q453X, NF2 F256fs, NF2 T59fs, NF2 Q65fs, NF2 E460X, NF2 K17_M29del, NF2 A211fs, NF2 Q459X, NF2 363+1G>C, NF2 K99fs, NF2 G43fs, NF2 K44X, NF2 K15fs, NF2 Y207fs, NF2 115-IG>A, NF2 Q319X, NF2 L14fs, NF2 M426fs, NF2 L208P, NF2 N104fs, NF2 R25fs, NF2 R262X, TRAF7 C388Y, TRAF7 R641C, TRAF7 Q637H, TRAF7 K615E, TRAF7 L580del, TRAF7 R641C, TRAF7 G536S, TRAF7 N520S, TRAF7 S561N, TRAF7 G390E, TRAF7 R653Q, TRAF7 E353insFRRDAS, TRAF7 T145M, TRAF7 F337S, AKT1 E17K, KLF4 K409Q, SMO L412F, SMO W535L, PIK3CA R108H, PIK3R1 del306-307 and PRKAR1A A213D. In some embodiments, the mutant gene, or mutant gene product, is an amino acid having at least one mutation selected from the group consisting of NF2 Q453X, NF2 F256fs, NF2 T59fs, NF2 Q65fs, NF2 E460X, NF2 K17_M29del, NF2 A211fs, NF2 Q459X, NF2 363+1G>C, NF2 K99fs, NF2 G43fs, NF2 K44X, NF2 K15fs, NF2 Y207fs, NF2 115-1G>A, NF2 Q319X, NF2 L14fs, NF2 M426fs, NF2 L208P, NF2 N104fs, NF2 R25fs, NF2 R262X, TRAF7 C388Y, TRAF7 R641C, TRAF7 Q637H, TRAF7 K615E, TRAF7 L580del, TRAF7 R641C, TRAF7 G536S, TRAF7 N520S, TRAF7 S561N, TRAF7 G390E, TRAF7 R653Q, TRAF7 E353insFRRDAS, TRAF7 T145M, TRAF7 F337S, AKT1 E17K, KLF4 K409Q, SMO L412F, SMO W535L, PIK3CA R108H, PIK3R1 del306-307 and PRKAR1A A213D. In some embodiments, the neoplasia is meningioma. In one embodiment, the subject is a human.

In another embodiment, the invention is an isolated nucleic acid comprising a mutant gene, or fragment thereof, associated with neoplasia, wherein the mutant gene, or fragment thereof, is at least one selected from the group consisting of mutant NF2, mutant TRAF7, mutant AKT1, mutant KLF4, mutant SMO, mutant PIK3CA, mutant PIK3R1, mutant BRCA1, mutant CREBBP, mutant SMARCB1 and mutant PRKAR1A. In some embodiments, the at least one mutant gene, or fragment thereof, comprises a nucleic acid sequence encoding an amino acid having at least one mutation selected from the group consisting of NF2 Q453X, NF2 F256fs, NF2 T59fs, NF2 Q65fs, NF2 E460X, NF2 K17_M29del, NF2 A21 fs, NF2 Q459X, NF2 363+1G>C, NF2 K99fs, NF2 G43fs, NF2 K44X, NF2 K15fs, NF2 Y207fs, NF2 115-1G>A, NF2 Q319X, NF2 L14fs, NF2 M426fs, NF2 L208P, NF2 N104fs, NF2 R25fs, NF2 R262X, TRAF7 C388Y, TRAF7 R641C, TRAF7 Q637H, TRAF7 K615E, TRAF7 L580del, TRAF7 R641C, TRAF7 G536S, TRAF7 N520S, TRAF7 S561N, TRAF7 G390E, TRAF7 R653Q, TRAF7 E353insFRRDAS, TRAF7 T145M, TRAF7 F337S, AKT1 E17K, KLF4 K409Q, SMO L412F, SMO W535L, PIK3CA R108H, PIK3R1 del306-307 and PRKAR1A A213D.

In another embodiment, the invention is an isolated polypeptide, or fragment thereof, encoded by a mutant gene associated with neoplasia, wherein the mutant gene, or fragment thereof, is at least one selected from the group consisting of mutant NF2, mutant TRAF7, mutant AKT1, mutant KLF4, mutant SMO, mutant PIK3CA, mutant PIK3R1, mutant BRCA1, mutant CREBBP, mutant SMARCB1 and mutant PRKAR1A. In some embodiments, the isolated polypeptide comprises an amino acid sequence having at least one mutation selected from the group consisting of NF2 Q453X, NF2 F256fs, NF2 T59fs, NF2 Q65fs, NF2 E460X, NF2 K17_M29del, NF2 A21 Ifs, NF2 Q459X, NF2 363+1G>C, NF2 K99fs, NF2 G43fs, NF2 K44X, NF2 K15fs, NF2 Y207fs, NF2 115-1G>A, NF2 Q319X, NF2 L14fs, NF2 M426fs, NF2 L208P, NF2 N104fs, NF2 R25fs, NF2 R262X, TRAF7 C388Y, TRAF7 R641C, TRAF7 Q637H, TRAF7 K615E, TRAF7 L580del, TRAF7 R641C, TRAF7 G536S, TRAF7 N520S, TRAF7 S561N, TRAF7 G390E, TRAF7 R653Q, TRAF7 E353insFRRDAS, TRAF7 T145M, TRAF7 F337S, AKT1 E17K, KLF4 K409Q, SMO L412F, SMO W535L, PIK3CA R108H, PIK3R1 del306-307 and PRKAR1A A213D.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A is an axial MRI image, which shows contrast enhancing meningioma originating from the anterior skull base. FIG. 1B is a sagittal MRI image, which shows extensive brain invasion due to an atypical meningioma. FIG. 1C is a Q-Q plot for the significance of observed mutations for genes with at least 2 mutations in the exome sequencing data set. NF2, TRAF7, AKT1, KLF4 and SMO genes are enriched for deleterious mutations. The circle size is proportional to the number of mutations identified. FIG. 1D is an image depicting the mutational profile of 300 meningioma samples based on exome (n=50) and targeted sequencing for NF2, TRAF7 and SMO coding exons along with recurrent $AKT1^{E17K}$ and $KLF4^{K409}$ mutations. Analysis for chromosome 22 copy number is also shown. Each bar represents a meningioma sample. FIG. 1E is an image depicting that a majority of TRAF7 mutations are clustered within its WD40 domains. FIG. 1F is an image demonstrating that the recurrent $KLF4^{K409}$ mutation is located within its first zinc finger domain makes direct DNA contact. FIG. 1G is a set of images depicting immunohistochemical staining with a mutation specific antibody, which identifies the recurrent $AKT1^{E17}K$ mutation (left and right panels, AKT mutant and control meningiomas, respectively). FIG. 1H is a circos plot of large scale genomic abnormalities identified, showing both deletions and amplifications). Whereas all NF2/loss meningiomas (outer circles) show chromosome 22 loss which can be associated with further large scale genomic abnormalities in grade II tumors, chromosomal stability is a hallmark of non-NF2 tumors (inner circles).

FIG. 2, comprising FIG. 2A through FIG. 2D are a set of images demonstrating that along the skull base, NF2/loss meningiomas were found in the lateral and posterior regions (FIG. 2A), whereas virtually all medial meningiomas were non-NF2 mutant (FIG. 2B through FIG. 2D). AKT1 (FIG. 2B) and SMO (FIG. 2D) mutant tumors were identified near the midline. FIG. 2E is an image demonstrating that along the cerebral convexities, the ratio of NF2/loss meningiomas increased posteriorly. In the parieto-occipital regions, cerebellar convexities and spinal cord, virtually all meningiomas were due to NF2/loss. FIG. 2F through FIG. 2I are a set of images demonstrating that the mutational profile of meningiomas correlated with histological subtypes with virtually all secretory meningiomas being KLF4 mutants (FIG. 2F). Whereas majority of fibrous (FIG. 2G) and psammatous (FIG. 2H) tumors were associated with NF2/loss, most meningothelial meningiomas (FIG. 2I) were due to non-NF2 mutations. FIG. 2J is an image demonstrating that unsupervised hierarchical clustering based on or gene expression analyses defined 2 major meningioma subgroups based on driver mutations. Non-NF2 mutant meningiomas were further subclassified based on a small number of genes that showed differential expression ($lod_{de}>5$) between TRAF7/KLF4, TRAF7/AKT1 and SMO subclasses. FIG. 2K is an image demonstrating that gene expression and H3K27 promoter acetylation ChIP-seq analyses showed strong correlation and identified several genes differentially expressed and acetylated between NF2/loss and non-NF2 meningiomas (log 2 fold changes are shown)

FIG. 3, comprising FIG. 3A is an image demonstrating that AKT1 mutant meningiomas showed increased MAPKinase activity, whereas KLF4 tumors revealed higher VEGF signaling. FIG. 3B is an image demonstrating that Hedgehog pathway was activated in SMO mutant meningiomas. FIG. 3C is an image demonstrating that activity of several pathways (including Wnt, receptor kinase and integrin signaling) were increased in NF2/loss meningiomas. FIG. 3D is an image demonstrating that reactome analysis of differentially expressed genes in NF2/loss versus non-NF2 meningiomas confirmed differential activity of several pathways. The size of each circle is proportional to fold change of differential expression; the outer circle shows differential promoter acetylation, which correlates with gene expression levels for most transcripts. Differentially expressed genes were grouped according to the pathway they belong. FIG. 3E through FIG. 3G are a set of images demonstrating that NF2/loss meningiomas showed increased expression of several MHC class II molecules which correlated with the presence of infiltrating immune cells. These cells formed distinct clusters from EMA positive tumor cells as identified by MHC class II staining. FIG. 3E and FIG. 3G represent two different NF2 mutant meningiomas; FIG. 3F is higher magnification of the image in FIG. 3E.

FIG. 5A through FIG. 5C, is s set of images and graphs depicting the results of experiments demonstrating representative $AKT1^{E17}K$, KLF4, and NF2 staining and quantification.*: P<0.05; : P<0.01; *: P<0.001. FIG. 5A demonstrates that $AKT1^{E17K}$ product, as visualized by a mutation specific antibody, is specifically expressed in AKT1 mutant meningiomas. FIG. 5B demonstrates that KLF4 is not differentially expressed between meningioma subtypes. FIG. 5C demonstrates that NF2 protein levels are markedly decreased in NF2 mutant tumors.

FIG. 6A through FIG. 6C, is a set of images depicting the results of experiments demonstrating KLF4-DNA interactions. FIG. 6A depicts interactions between K409 and a guanosine in the DNA binding motif. FIG. 6B depicts putative novel interactions made upon K409Q mutation, with possible hydrogen bond formations with an adjacent guanosine and with H412. FIG. 6C depicts a surface representation of the entire KLF4 zinc finger in complex with DNA. PDB ID: 2WBU.

FIG. 7A and FIG. 7B, is a set of images depicting the results of experiments demonstrating the crystal structures of wild-type (wt) AKT1 and $AKT1^{E17K}$. FIG. 7A depicts the wt AKT1 lipid-binding pocket and phosphatidylinositol 3,4,5-trisphosphate. FIG. 7B demonstrates that $AKT1^{E17K}$ coordinates novel interactions between AKT1 and ligand in the lipid-binding pocket, which has been shown to promote tumorigenesis in various cancers. PDB IDs: 1UNQ (wt ATK1), 2UZS ($AKT1^{E17K}$).

FIG. 9A through FIG. 9D, is a set of graphs depicting the results of experiments, providing a representative demonstration of copy number variation as determined by whole genome genotyping data using the Illumina Human OmniExpress-12v1.0 BeadChips. FIG. 9A depicts the Log 2 ratio of normalized signal intensities between tumor and blood samples. FIG. 9B depicts the absolute difference of B allele frequencies (BAF) between tumor and blood samples. FIG. 9C and FIG. 9D depict BAF for tumor and blood samples, respectively.

FIG. 10, comprising FIG. 10A through FIG. 10H, are a set of images depicting pre-operative magnetic resonance imaging (MRI) of exome-sequenced meningiomas. Samples indicated by asterisk (*) do not have blood pairing. Images not available for two subjects (MN-71, MN-1066). FIG. 10A is a set of MRI images of NF2 mutated Grade II meningioma. FIG. 10B is a set of MRI images of NF2 mutated Grade I meningioma. FIG. 10C is a set of MRI images of Grade II meningioma with chromosome 22 loss only. FIG. 10D is a set of MRI images of Grade I meningioma with chromosome 22 loss only. FIG. 10E is a set of MRI images of Grade II meningioma with coding TRAF7 mutations. FIG. 10F is a set of MRI images of Grade I meningioma with coding TRAF7 mutations. FIG. 10G is a set of MRI images of Grade I meningioma with SMO mutations. FIG. 10H is a set of MRI images of Grade I meningioma with no identifiable or other driver mutations.

FIG. 15 is a table depicting exome sequencing that identifies meningioma driver mutations.

DETAILED DESCRIPTION

Figures 1A, 1B, 1C, 1D:
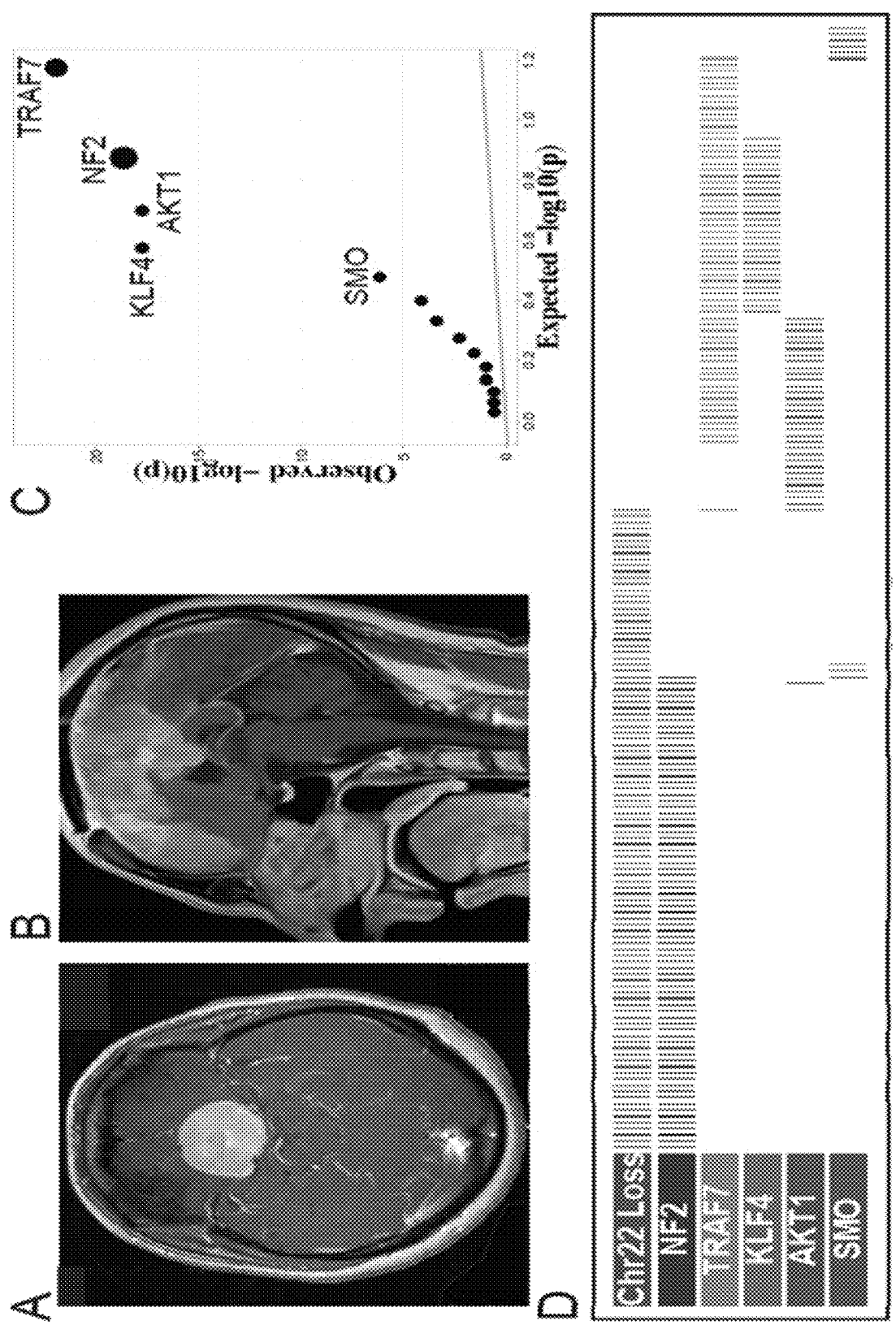
FIG. 1A through FIG. 1H, are a set of images depicting the results of experiments demonstrating the genomic architecture of meningiomas.

The present invention relates to the discovery that particular mutations are associated with neoplasia, such as meningioma. Thus, the invention relates to compositions and methods useful for the assessment, characterization, classification and treatment of neoplasia, including meningioma, based upon the presence or absence of particular mutations that are associated with neoplasia, including meningioma. In various embodiments, the gene having a mutation associated with neoplasia is at least one of NF2, TRAF7, AKT1, KLF4, SMO, PIK3CA, PIK3R1, BRCA1, CREBBP, SMARCB1 and PRKAR1A. In some embodiments, the neoplasia-associated mutations described herein occur concomitantly with the loss of chromosome 22.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

An "allele" refers to one specific form of a genetic sequence (such as a gene) within a cell, an individual or within a population, the specific form differing from other forms of the same gene in the sequence of at least one, and frequently more than one, variant sites within the sequence of the gene. The sequences at these variant sites that differ between different alleles are termed "variants," "polymorphisms," or "mutations."

As used herein, to "alleviate" a disease means reducing the frequency or severity of at least one sign or symptom of a disease or disorder.

As used herein the terms "alteration," "defect," "variation," or "mutation," refers to a mutation in a gene in a cell that affects the function, activity, expression (transcription or translation) or conformation of the polypeptide that it encodes. Mutations encompassed by the present invention can be any mutation of a gene in a cell that results in the enhancement or disruption of the function, activity, expression or conformation of the encoded polypeptide, including the complete absence of expression of the encoded protein and can include, for example, missense and nonsense mutations, insertions, deletions, frameshifts and premature terminations. Without being so limited, mutations encompassed by the present invention may alter splicing the mRNA (splice site mutation) or cause a shift in the reading frame (frameshift mutation). A "mutation" also refers to a change in nucleic acid or polypeptide sequence relative to a reference sequence (which is preferably a naturally-occurring normal or "wild-type" sequence), and includes translocations, deletions, insertions, and substitutions/point mutations. A "mutant" as used herein, refers to either a nucleic acid or protein comprising a mutation.

The term "amplification" refers to the operation by which the number of copies of a target nucleotide sequence present in a sample is multiplied.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab and F(ab)2, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, an "immunoassay" refers to any binding assay that uses an antibody capable of binding specifically to a target molecule to detect and quantify the target molecule.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen.

However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "applicator," as the term is used herein, is meant any device including, but not limited to, a hypodermic syringe, a pipette, an iontophoresis device, a patch, and the like, for administering the compositions of the invention to a subject.

"Neoplasia," as used herein, refers to the abnormal growth or division of cells. The growth of neoplastic cells exceeds, and is not coordinated with, that of the normal tissues around it. The growth of neoplastic cells may result in a lump or tumor. Neoplasms may be benign, pre-malignant or malignant. Neoplasia occurs in a variety of cells and tissues, including the oral cavity (e.g., mouth, tongue, pharynx, etc.), digestive system (e.g., esophagus, stomach, small intestine, colon, rectum, liver, bile duct, gall bladder, pancreas, etc.), respiratory system (e.g., larynx, lung, bronchus, etc.), bones, joints, skin (e.g., basal cell, squamous cell, meningioma, etc.), breast, genital system, (e.g., uterus, ovary, prostate, testis, etc.), urinary system (e.g., bladder, kidney, ureter, etc.), eye, nervous system (e.g., brain, etc.), endocrine system (e.g., thyroid, etc.), and hematopoietic system (e.g., lymphoma, myeloma, leukemia, acute lymphocytic leukemia, chronic lymphocytic leukemia, acute myeloid leukemia, chronic myeloid leukemia, etc.).

The term "coding sequence," as used herein, means a sequence of a nucleic acid or its complement, or a part thereof, that can be transcribed and/or translated to produce the mRNA and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the coding sequence can be deduced therefrom. In contrast, the term "non-coding sequence," as used herein, means a sequence of a nucleic acid or its complement, or a part thereof, that is not translated into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, and the like.

As used herein, the term "control nucleic acid" is meant to refer to a nucleic acid (e.g., RNA, DNA) that does not come from a subject known to have, or suspected to have, a mutation in a gene in a cell (e.g., for a control subject). For example, the control can be a wild type nucleic acid sequence which does not contain a variation in its nucleic acid sequence. Also, as used herein, a control nucleic acid can be a fragment or portion of gene that does not include the defect/variation that is the mutation of interest (that is, the mutation to be detected in an assay).

As used herein, "clonal expansion" refers to the increase in the number of progeny cells originating from one cell.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

As used herein, the term "diagnosis" refers to the determination of the nature of a case of disease. In some embodiments of the present invention, methods for making a diagnosis are provided which permit determination of a particular mutation associated with neoplasia, such as meningioma.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

By "driver mutation," as used herein, is meant a mutation that is causally associated with the development, survival, proliferation and/or the progression of a neoplastic cell. Typically, a driver mutation imparts a growth advantage to the neoplastic cell. A driver mutation is often, but is not necessarily, required for the continued maintenance of the neoplastic cell phenotype. In contrast, a "passenger mutation" is a mutation present in a neoplastic cell genome and does not functionally contribute to the neoplastic cell phenotype.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., DNA, rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides; at least about 1000 nucleotides to about 1500 nucleotides; about 1500 nucleotides to about 2500 nucleotides; or about 2500 nucleotides (and any integer value in between). As used herein, the term "fragment," as applied to a protein or peptide, refers to a subsequence of a larger protein or peptide. A "fragment" of a protein or peptide can be at least about 20 amino acids in length; for example, at least about 50 amino acids in length; at least about 100 amino acids in length; at least about 200 amino acids in length; at least about 300 amino acids in length; or at least about 400 amino acids in length (and any integer value in between).

The term "gene" refers to a nucleic acid (e.g., DNA) sequence that includes coding sequences necessary for the production of a polypeptide, precursor, or RNA (e.g., mRNA). The polypeptide may be encoded by a full length coding sequence or by any portion of the coding sequence so long as the desired activity or functional property (e.g., enzymatic activity, ligand binding, signal transduction, immunogenicity, etc.) of the full-length or fragment is retained. The term also encompasses the coding region of a structural gene and the sequences located adjacent to the coding region on both the 5' and 3' ends for a distance of about 2 kb or more on either end such that the gene corresponds to the length of the full-length mRNA and 5' regulatory sequences which influence the transcriptional properties of the gene. Sequences located 5' of the coding region and present on the mRNA are referred to as 5'-untranslated sequences. The 5'-untranslated sequences usually contain the regulatory sequences. Sequences located 3' or downstream of the coding region and present on the mRNA are referred to as 3'-untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

A "genome" is all the genetic material of an organism. In some instances, the term genome may refer to the chromosomal DNA. Genome may be multichromosomal such that the DNA is cellularly distributed among a plurality of individual chromosomes. For example, in human there are 22 pairs of chromosomes plus a gender associated XX or XY pair. DNA derived from the genetic material in the chromosomes of a particular organism is genomic DNA. The term genome may also refer to genetic materials from organisms that do not have chromosomal structure. In addition, the term genome may refer to mitochondria DNA. A genomic library is a collection of DNA fragments representing the whole or a portion of a genome. Frequently, a genomic library is a collection of clones made from a set of randomly generated, sometimes overlapping DNA fragments representing the entire genome or a portion of the genome of an organism.

The term "chromosome" refers to the heredity-bearing gene carrier of a cell which comprises DNA and protein components (especially histones). The conventional internationally recognized individual human genome chromosome numbering system is employed herein. The size of an individual chromosome can vary from one type to another within a given multi-chromosomal genome and from one genome to another. In the case of the human genome, the entire DNA mass of a given chromosome is usually greater than about 100,000,000 bp. For example, the size of the entire human genome is about $3\times10^9$ bp. The largest chromosome, chromosome no. 1, contains about $2.\times10^8$ by while the smallest chromosome, chromosome no. 22, contains about $5.3\times10^7$ bp.

A "chromosomal region" is a portion of a chromosome. The actual physical size or extent of any individual chromosomal region can vary greatly. The term "region" is not necessarily definitive of a particular one or more genes because a region need not take into specific account the particular coding segments (exons) of an individual gene.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared X 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "housekeeping gene" as used herein refers to genes that are generally always expressed and thought to be involved in routine cellular metabolism. Housekeeping genes are well known and include such genes as glyceraldehyde-3-phosphate dehydrogenase (G3PDH or GAPDH), albumin, actins, tubulins, cyclophilin, hypoxanthine phsophoribosyltransferase (HRPT), 28S, and 18S rRNAs and the like.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids. A single molecule that contains pairing of complementary nucleic acids within its structure is said to be "self-hybridized." A single DNA molecule with internal complementarity could assume a variety of secondary structures including loops, kinks or, for long stretches of base pairs, coils.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

"Instructional material," as that term is used herein, includes a publication, a recording, a diagram, or any other medium of expression which can be used to communicate the usefulness of the nucleic acid, peptide, and/or compound of the invention in the kit for identifying, diagnosing or alleviating or treating the various diseases or disorders recited herein. Optionally, or alternately, the instructional material may describe one or more methods of identifying, diagnosing or alleviating the diseases or disorders in a cell or a tissue of a subject. The instructional material of the kit may, for example, be affixed to a container that contains the nucleic acid, peptide, and/or compound of the invention or be shipped together with a container that contains the nucleic acid, peptide, and/or compound. Alternatively, the instructional material may be shipped separately from the container with the intention that the recipient uses the instructional material and the compound cooperatively.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

The term "label" when used herein refers to a detectable compound or composition that is conjugated directly or indirectly to a probe to generate a "labeled" probe. The label may be detectable by itself (e.g. radioisotope labels or fluorescent labels) or, in the case of an enzymatic label, may catalyze chemical alteration of a substrate compound or composition that is detectable (e.g., avidin-biotin). In some instances, primers can be labeled to detect a PCR product.

The terms "microarray" and "array" refer broadly to both "DNA microarrays" and "DNA chip(s)," and encompass all art-recognized solid supports, and all art-recognized methods for affixing nucleic acid molecules thereto or for synthesis of nucleic acids thereon. Preferred arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 5,800,992, 6,040,193, 5,424,186 and Fodor et al., 1991, Science, 251:767-777, each of which is incorporated by reference in its entirety for all purposes. Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as fiber optics, glass or any other appropriate substrate. (See U.S. Pat. Nos. 5,770,358, 5,789, 162, 5,708,153, 6,040,193 and 5,800,992, which are hereby incorporated by reference in their entirety for all purposes.) Arrays may be packaged in such a manner as to allow for diagnostic use or can be an all-inclusive device; e.g., U.S. Pat. Nos. 5,856,174 and 5,922,591 incorporated in their entirety by reference for all purposes. Arrays are commercially available from, for example, Affymetrix (Santa Clara, Calif.) and Applied Biosystems (Foster City, Calif.), and are directed to a variety of purposes, including genotyping, diagnostics, mutation analysis, marker expression, and gene expression monitoring for a variety of eukaryotic and prokaryotic organisms. The number of probes on a solid support may be varied by changing the size of the individual features. In one embodiment the feature size is 20 by 25 microns square, in other embodiments features may be, for example, 8 by 8, 5 by 5 or 3 by 3 microns square, resulting in about 2,600,000, 6,600,000 or 18,000,000 individual probe features.

Assays for amplification of the known sequence are also disclosed. For example primers for PCR may be designed to amplify regions of the sequence. For RNA, a first reverse transcriptase step may be used to generate double stranded DNA from the single stranded RNA. The array may be designed to detect sequences from an entire genome; or one or more regions of a genome, for example, selected regions of a genome such as those coding for a protein or RNA of interest; or a conserved region from multiple genomes; or multiple genomes. Arrays and methods of genetic analysis using arrays is described in Cutler, et al., 2001, Genome Res. 11(11):1913-1925 and Warrington, et al., 2002, Hum Mutat 19:402-409 and in US Patent Pub No 20030124539, each of which is incorporated herein by reference in its entirety.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

A "nucleic acid" refers to a polynucleotide and includes poly-ribonucleotides and poly-deoxyribonucleotides. Nucleic acids according to the present invention may include any polymer or oligomer of pyrimidine and purine bases, preferably cytosine, thymine, and uracil, and adenine and guanine, respectively. (See Albert L. Lehninger, Principles of Biochemistry, at 793-800 (Worth Pub. 1982) which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferably at least 8, 15 or 25 nucleotides in length, but may be up to 50, 100, 1000, or 5000 nucleotides long or a compound that specifically hybridizes to a polynucleotide. Polynucleotides include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety.) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this disclosure. It will be understood that when a nucleotide sequence is represented herein by a DNA sequence (e.g., A, T, G, and C), this also includes the corresponding RNA sequence (e.g., A, U, G, C) in which "U" replaces "T".

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "polymerase chain reaction" ("PCR") refers to the method of K. B. Mullis (U.S. Pat. Nos. 4,683,195 4,683,202, and 4,965,188, hereby incorporated by reference), which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". As used herein, the terms "PCR product," "PCR fragment," "amplification product" or "amplicon" refer to the resultant mixture of compounds after two or more cycles of the PCR steps of denaturation, annealing and extension are complete. These terms encompass the case where there has been amplification of one or more segments of one or more target sequences.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences.

The term "perfect match," "match," "perfect match probe" or "perfect match control" refers to a nucleic acid that has a sequence that is perfectly complementary to a particular target sequence. The nucleic acid is typically perfectly complementary to a portion (subsequence) of the target sequence. A perfect match (PM) probe can be a "test probe", a "normalization control" probe, an expression level control probe and the like. A perfect match control or perfect match is, however, distinguished from a "mismatch" or "mismatch probe." The term "mismatch," "mismatch control" or "mismatch probe" refers to a nucleic acid whose sequence is not perfectly complementary to a particular target sequence. As a non-limiting example, for each mismatch (MM) control in a high-density probe array there typically exists a corresponding perfect match (PM) probe that is perfectly complementary to the same particular target sequence. The mismatch may comprise one or more bases. While the mismatch(es) may be located anywhere in the mismatch probe, terminal mismatches are less desirable because a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, "polynucleotide" includes cDNA, RNA, DNA/RNA hybrid, antisense RNA, ribozyme, genomic DNA, synthetic forms, and mixed polymers, both sense and antisense strands, and may be chemically or biochemically modified to contain non-natural or derivatized, synthetic, or semi-synthetic nucleotide bases. Also, contemplated are alterations of a wild type or synthetic gene, including but not limited to deletion, insertion, substitution of one or more nucleotides, or fusion to other polynucleotide sequences.

The term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer, which may include constituents which are co-factors or which affect conditions such as pH and the like at various suitable temperatures. A primer is preferably a single strand sequence, such that amplification efficiency is optimized, but double stranded sequences can be utilized.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The term "reaction mixture" or "PCR reaction mixture" or "master mix" or "master mixture" refers to an aqueous solution of constituents in a PCR reaction that can be constant across different reactions. An exemplary PCR reaction mixture includes buffer, a mixture of deoxyribonucleoside triphosphates, primers, probes, and DNA polymerase. Generally, template RNA or DNA is the variable in a PCR.

"Sample" or "biological sample" as used herein means a biological material derived from a subject. The biological sample may contain any biological material suitable for detecting a mutation in a gene, and may comprise cellular and/or non-cellular material obtained from the individual.

A "somatic mutation," as used herein, is a genetic alteration acquired by a somatic cell that can be passed on to progeny cells of the mutated somatic cell in the course of cell division. Somatic mutations differ from germ line mutations, which are inherited genetic alterations that occur in germ cells.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under "medium stringency conditions," a nucleic acid sequence of interest will hybridize only to its exact complement, sequences with single base mismatches, and closely related sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

As used herein, "substantially purified" refers to being essentially free of other components. For example, a substantially purified cell is a cell which has been separated from other cell types with which it is normally associated in its naturally occurring state. In some instances, a population of substantially purified cells refers to a homogenous population of cells. In other instances, this term refers simply to a cell that have been separated from the cells with which they are naturally associated in their natural state.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Targets are sometimes referred to in the art as anti-probes. As the term target is used herein, no difference in meaning is intended.

As used herein, the terms "therapy" or "therapeutic regimen" refer to those medical steps taken to alleviate or alter a disorder or disease state, e.g., a course of treatment intended to reduce or eliminate the affects or symptoms of a disease using pharmacological, surgical, dietary and/or other techniques. A therapeutic regimen may include a prescribed dosage of one or more drugs or surgery. Therapies will most often be beneficial and reduce the disorder or disease state but in many instances the effect of a therapy will have non-desirable or side-effects. The effect of therapy will also be impacted by the physiological state of the host, e.g., age, gender, genetics, weight, other disease conditions, etc.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

As used herein, the term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and/or functional properties (i.e., altered characteristics) when compared to the wild-type gene or gene product. It is noted that naturally occurring mutants can be isolated; these are identified by the fact that they have altered characteristics (including altered nucleic acid or amino acid sequences) when compared to the wild-type gene or gene product.

Standard codon/amino acid designators:

| Codon | Amino Acid | 3-Letter Abbreviation | 1-Letter Abbreviation |
|---|---|---|---|
| TTT | Phenylalanine | Phe | F |
| TTC | Phenylalanine | Phe | F |
| TTA | Leucine | Leu | L |
| TTG | Leucine | Leu | L |
| TCT | Serine | Ser | S |
| TCC | Serine | Ser | S |
| TCA | Serine | Ser | S |
| TCG | Serine | Ser | S |
| TAT | Tyrosine | Tyr | Y |
| TAC | Tyrosine | Tyr | Y |

-continued

| Codon | Amino Acid | 3-Letter Abbreviation | 1-Letter Abbreviation |
|---|---|---|---|
| TAA | Termination | Ter | X |
| TAG | Termination | Ter | X |
| TGT | Cysteine | Cys | C |
| TGC | Cysteine | Cys | C |
| TGA | Termination | Ter | X |
| TGG | Tryptophan | Trp | W |
| CTT | Leucine | Leu | L |
| CTC | Leucine | Leu | L |
| CTA | Leucine | Leu | L |
| CTG | Leucine | Leu | L |
| CCT | Proline | Pro | P |
| CCC | Proline | Pro | P |
| CCA | Proline | Pro | P |
| CCG | Proline | Pro | P |
| CAT | Histidine | His | H |
| CAC | Histidine | His | H |
| CAA | Glutamine | Gln | Q |
| CAG | Glutamine | Gln | Q |
| CGT | Arginine | Arg | R |
| CGC | Arginine | Arg | R |
| CGA | Arginine | Arg | R |
| CGG | Arginine | Arg | R |
| ATT | Isoleucine | Ile | I |
| ATC | Isoleucine | Ile | I |
| ATA | Isoleucine | Ile | I |
| ATG | Methionine | Met | M |
| ACT | Threonine | Thr | T |
| ACC | Threonine | Thr | T |
| ACA | Threonine | Thr | T |
| ACG | Threonine | Thr | T |
| AAT | Asparagine | Asn | N |
| AAC | Asparagine | Asn | N |
| AAA | Lysine | Lys | K |
| AAG | Lysine | Lys | K |
| AGT | Serine | Ser | S |
| AGC | Serine | Ser | S |
| AGA | Arginine | Arg | R |
| AGG | Arginine | Arg | R |
| GTT | Valine | Val | V |
| GTC | Valine | Val | V |
| GTA | Valine | Val | V |
| GTG | Valine | Val | V |
| GCT | Alanine | Ala | A |
| GCC | Alanine | Ala | A |
| GCA | Alanine | Ala | A |
| GCG | Alanine | Ala | A |
| GAT | Aspartate | Asp | D |
| GAC | Aspartate | Asp | D |
| GAA | Glutamate | Glu | E |
| GAG | Glutamate | Glu | E |
| GGT | Glycine | Gly | G |
| GGC | Glycine | Gly | G |
| GGA | Glycine | Gly | G |
| GGG | Glycine | Gly | G |

Description

The present invention relates to the discovery that particular mutations are associated with neoplasia, including meningioma. The invention relates to compositions and methods useful for the assessment, characterization, classification, molecular classification, and treatment of neoplasia, including meningioma, based upon the presence or absence of particular mutations that are associated with neoplasia, including meningioma.

In various embodiments, the compositions of the invention relate to mutations associated with meningioma, genes having at least one mutation associated with meningioma, modulators of genes having at least one mutation associated with meningioma, modulators of gene products having at least one mutation associated with meningioma, as well as modulators of genes and gene products upstream and downstream of the genes identified as having a mutation associated with meningioma.

In other embodiments, the methods of the invention relate to methods of diagnosing meningioma, methods of prognosis of meningioma, methods of grading and classifying meningioma, methods of molecular classification of meningioma, methods of determining the optimal treatment regimen for meningioma, and methods of monitoring the outcome of a treatment regimen of meningioma.

In some embodiments, the mutation of the invention associated with meningioma is a somatic mutation. In some embodiments, the mutation of the invention associated with meningioma is a driver mutation. In one embodiment, the gene having a mutation associated with meningioma is NF2. In some embodiments, the mutant gene associated with meningioma is NF2 having at least one of the mutations selected from Q453X, F256fs, T59fs, Q65fs, E460X, K17_M29del, A211fs, Q459X, 363+1G>C, K99fs, G43fs, K44X, K15fs, Y207fs, 115-1G>A, Q319X, L14fs, M426fs, L208P, N104fs, R25fs, or R262X.

In another embodiment, the gene having a mutation associated with meningioma is TRAF7. In some embodiments, the mutant gene associated with meningioma is TRAF7 having at least one of the mutations selected from C388Y, R641C, Q637H, K615E, L580del, R641C, G536S, N520S, S561N, G390E, R653Q, E353insFRRDAS, T145M, or F337S.

In another embodiment, the gene having a mutation associated with meningioma is AKT1. In some embodiments, the mutant gene associated with meningioma is AKT1 having the mutation E17K.

In another embodiment, the gene having a mutation associated with meningioma is KLF4. In some embodiments, the mutant gene associated with meningioma is KLF4 having the mutation K409Q.

In another embodiment, the gene having a mutation associated with meningioma is SMO. In some embodiments, the mutant gene associated with meningioma is SMO having at least one of the mutations selected from L412F or W535L.

In another embodiment, the gene having a mutation associated with meningioma is PIK3CA. In some embodiments, the mutant gene associated with meningioma is PIK3CA having the mutation R108H.

In another embodiment, the gene having a mutation associated with meningioma is PIK3R1. In some embodiments, the mutant gene associated with meningioma is PIK3R1 having a deletion at amino acid positions 306-307.

In another embodiment, the gene having a mutation associated with meningioma is PRKAR1A. In some embodiments, the mutant gene associated with meningioma is PRKAR1A having the mutation A213D.

In another embodiment, the gene having a mutation associated with meningioma is BRCA1, CREBBP or SMARCB1.

In some cases, the meningioma-associated mutations described herein occur concomitantly with the loss of chromosome 22.

Assays

The present invention relates to the discovery that particular mutations in particular genes are associated with the development and progression of neoplasia, including meningioma. In various embodiments, the invention relates to a genetic screening assay of a subject to determine whether the subject has a mutation associated with neoplasia, such as meningioma. The present invention provides methods of assessing for the presence or absence of a mutation associated with neoplasia, as well as methods of diagnosing a subject having a mutation associated with neoplasia. The mutations associated with neoplasia described herein include alterations (e.g., substitution, deletion, insertion, or transition) in the nucleic acid sequence of a variety of genes, as elsewhere described herein throughout. The positions of the mutations in the gene sequences described herein are numbered in relation to the nucleic acid sequence or amino acid sequence. That is, the numbered position of an altered nucleotide, or amino acid, is the position number of that nucleotide, or amino acid, in the nucleic acid or amino acid sequence. In various embodiments, the mutations associated with neoplasia of the invention are somatic mutations. In various embodiments, the mutations associated with neoplasia of the invention are driver mutations. In various embodiments, the gene having a mutation that is associated with neoplasia is a gene of at least one of NF2, TRAF7, AKT1, KLF4, SMO, PIK3CA, PIK3R1, BRCA1, CREBBP, SMARCB1 and PRKAR1A.

In one embodiment, the method of the invention is a diagnostic assay for diagnosing neoplasia, including meningioma, in a subject in need thereof, by determining whether a mutation is present in a gene associated with neoplasia in a biological sample obtained from the subject. The results of the diagnostic assay can be used alone, or in combination with other information from the subject, or from the biological sample obtained from the subject. The mutation identified by the assay can be any mutation in any gene associated with neoplasia. The mutation identified by the assay can be any mutation in any gene elsewhere disclosed herein. The mutation identified by the assay can be any mutation elsewhere described herein. In various embodiments, the gene having a mutation associated with neoplasia is at least one of NF2, TRAF7, AKT1, KLF4, SMO, PIK3CA, PIK3R1, BRCA1, CREBBP, SMARCB1 and PRKAR1A.

In another embodiment, the method of the invention is a prognostic assay for developing a prognosis of the outcome of neoplasia, including meningioma, in a subject in need thereof, by determining whether a mutation is present in a gene associated with neoplasia in a biological sample obtained from the subject. The results of the prognostic assay can be used alone, or in combination with other information from the subject, or from the biological sample obtained from the subject. The mutation identified by the assay can be any mutation in any gene associated with neoplasia. The mutation identified by the assay can be any mutation in any gene elsewhere disclosed herein. The mutation identified by the assay can be any mutation elsewhere described herein. In various embodiments, the gene having a mutation associated with neoplasia is at least one of NF2, TRAF7, AKT1, KLF4, SMO, PIK3CA, PIK3R1, BRCA1, CREBBP, SMARCB1 and PRKAR1A. In some embodiments, the assay for developing a prognosis of the outcome of neoplasia includes determining the likelihood that the meningioma is, or will become, malignant.

In a further embodiment, the method of the invention is an assay for monitoring the effectiveness of a treatment for neoplasia, including meningioma, in a subject in need thereof, by determining whether a mutation is present in a gene associated with neoplasia in a biological sample obtained from the subject. The assay can be performed before, during or after the treatment has been administered, or any combination thereof. The results of the assay can be used alone, or in combination with other information from the subject, or from the biological sample obtained from the subject. The mutation identified by the assay can be any mutation in any gene associated with neoplasia. The mutation identified by the assay can be any mutation in any gene elsewhere disclosed herein. The mutation identified by the assay can be any mutation elsewhere described herein. In various embodiments, the gene having a mutation associated with neoplasia is at least one of NF2, TRAF7, AKT1, KLF4, SMO, PIK3CA, PIK3R1, BRCA1, CREBBP, SMARCB1 and PRKAR1A.

In another embodiment, the method of the invention is an assay for determining the appropriate treatment for neoplasia, including meningioma, to be administered to subject in need thereof, by determining whether a particular mutation is present in a particular gene associated with neoplasia in a biological sample obtained from the subject. Certain mutations associated with neoplasia respond better to certain treatment regimens, and less well, or not all, to other treatment regimens. Thus, the mutations identified in the assays of the invention are useful in determining the appropriate treatment regimen to administer to a particular subject. Knowing which particular mutation, or mutations, are present in the biological sample of a particular subject, can guide the medical provider to select the optimal treatment regimen (e.g., the therapeutic composition, the therapeutic composition combinations, the dose, the frequency of administration, excision, etc.) to administer to any particular subject. The assay can be performed, before, during or after the treatment has been administered, or any combination thereof. The results of the assay can be used alone, or in combination with other information from the subject, or the biological sample obtained from the subject. The mutation identified by the assay can be any mutation in any gene associated with neoplasia. The mutation identified by the assay can be any mutation in any gene elsewhere disclosed herein. The mutation identified by the assay can be any mutation elsewhere described herein. In various embodiments, the gene having a mutation associated with neoplasia is at least one of NF2, TRAF7, AKT1, KLF4, SMO, PIK3CA, PIK3R1, BRCA1, CREBBP, SMARCB1 and PRKAR1A.

In another embodiment, the method of the invention is an assay for determining the optimal treatment for a subject's neoplasia, including meningioma, to be administered to subject in need thereof, by determining whether a particular mutation is present in a particular gene associated with neoplasia in a biological sample obtained from the subject. Certain mutations associated with neoplasia respond better to certain treatment regimens, and less well, or not all, to other treatment regimens. Thus, the mutations identified in the assays of the invention are useful in determining the appropriate treatment regimen to administer to a particular subject. Knowing which particular mutation, or mutations, are present in the biological sample of a particular subject, can guide the medical provider to select the optimal treatment regimen (e.g., the therapeutic composition, the therapeutic composition combinations, the dose, the frequency of administration, excision, etc.) to administer to any particular subject. The assay can be performed, before, during or after the treatment has been administered, or any combination thereof. The results of the assay can be used alone, or in combination with other information from the subject, or the biological sample obtained from the subject. The mutation identified by the assay can be any mutation in any gene associated with neoplasia. The mutation identified by the assay can be any mutation in any gene elsewhere disclosed herein. The mutation identified by the assay can be any mutation elsewhere described herein. In various embodiments, the gene having a mutation associated with neoplasia is at least one of NF2, TRAF7, AKT1, KLF4, SMO, PIK3CA, PIK3R1, BRCA1, CREBBP, SMARCB1 and PRKAR1A.

In the assay methods of the invention, a test biological sample from a subject is assessed for the presence of at least one mutation in at least one gene associated with neoplasia, including meningioma. In various embodiments, the subject is a human subject, and may be of any race, sex and age. Representative subjects include those who are suspected of having neoplasia, those who have been diagnosed with neoplasia, those whose have neoplasia, those who have had neoplasia, those who at risk of a recurrence of neoplasia, and those who are at risk of developing neoplasia. In particular embodiments, the neoplasia is meningioma.

In one embodiment, the test sample is a sample containing at least a fragment of a nucleic acid of a gene, or mutant gene, associated with neoplasia. The term, "fragment," as used herein, indicates that the portion of the gene, DNA, mRNA or cDNA is a polynucleotide of a length that is sufficient to identify it as a fragment of a gene, or mutant gene, associated with neoplasia. In one representative embodiment, a fragment comprises one or more exons of the gene, or mutant gene, associated with neoplasia. In another representative embodiment, a fragment comprises part of an exon of the gene, or mutant gene, associated with neoplasia. In some embodiments, the fragment can also include an intron/exon junction of the gene, or mutant gene, associated with neoplasia.

The test sample is prepared from a biological sample obtained from the subject. The biological sample can be a sample from any source which contains nucleic acid (e.g., DNA, chromosomal nucleic acid, or RNA), such as a body fluid or a tissue, or a tumor, or a combination thereof. A biological sample of nucleic acid from a cell, or a neoplastic cell, or a meningioma cell, or a tumor can be obtained by appropriate methods, such as, for example, biopsy. In certain embodiments, a biological sample containing genomic DNA is used. A biological sample can be used as the test sample; alternatively, a biological sample can be processed to enhance access to nucleic acids, or copies of nucleic acids (e.g., copies of nucleic acids comprising a mutation associated with meningioma), and the processed biological sample can then be used as the test sample. For example, in various embodiments, nucleic acid (e.g., genomic DNA or cDNA prepared from mRNA) is prepared from a biological sample, for use in the methods. Alternatively or in addition, if desired, an amplification method can be used to amplify nucleic acids comprising all or a fragment of a mRNA or genomic DNA in a biological sample, for use as the test sample in the assessment for the presence or absence of a mutation associated with neoplasia.

The test sample is assessed to determine whether one or more mutations are present in the nucleic acid of the subject. In general, detecting a mutation may be carried out by determining the presence or absence of nucleic acids containing a mutation of interest in the test sample.

In some embodiments, hybridization methods, such as Southern analysis, Northern analysis, or in situ hybridizations, can be used (see Current Protocols in Molecular Biology, Ausubel, F. et al., eds., John Wiley & Sons, including all supplements). For example, the presence of a mutation can be indicated by hybridization of nucleic acid in the genomic DNA, RNA, or cDNA to a nucleic acid probe. A "nucleic acid probe", as used herein, can be a DNA probe or an RNA probe; the nucleic acid probe can contain at least one polymorphism of interest, as described herein. The probe can be, for example, the gene, a gene fragment (e.g., one or more exons), a vector comprising the gene, a probe or primer, etc. For representative examples of use of nucleic acid probes, see, for example, U.S. Pat. Nos. 5,288,611 and 4,851,330.

To detect one or more mutations of interest, a hybridization sample is formed by contacting the test sample with at least one nucleic acid probe. A preferred probe for detecting mRNA or genomic DNA is a labeled nucleic acid probe capable of hybridizing to mRNA or genomic DNA of a gene, or a mutant gene, associated with neoplasia. The nucleic acid probe can be, for example, a full-length nucleic acid molecule, or a portion thereof, such as an oligonucleotide of at least 15, 30, 50, 100, 250 or 500 nucleotides in length and sufficient to specifically hybridize under stringent conditions to appropriate target mRNA, cDNA or genomic DNA. The hybridization sample is maintained under conditions which are sufficient to allow specific hybridization of the nucleic acid probe to mRNA, cDNA or genomic DNA of a gene, or mutant gene, associated with neoplasia. Specific hybridization can be performed under high stringency conditions or moderate stringency conditions, as appropriate. In a preferred embodiment, the hybridization conditions for specific hybridization are high stringency. Specific hybridization, if present, is then detected using standard methods. If specific hybridization occurs between the nucleic acid probe having a mutant sequence and a gene, mRNA or cDNA in the test sample, the mutation that is present in the nucleic acid probe is also present in the nucleic acid sequence of the subject. More than one nucleic acid probe can also be used concurrently in this method. Specific hybridization of any one of the nucleic acid probes is indicative of the presence of the mutation of interest, as described herein.

In Northern analysis (see Current Protocols in Molecular Biology, Ausubel, F. et al., eds., John Wiley & Sons, supra), the hybridization methods described above are used to identify the presence of a mutation of interest in an RNA, such as a mRNA. For Northern analysis, a test sample comprising RNA is prepared from a biological sample from the subject by appropriate means. Specific hybridization of a nucleic acid probe, as described above, to RNA from the subject is indicative of the presence of a mutation of interest, as described herein.

Alternatively, a peptide nucleic acid (PNA) probe can be used instead of a nucleic acid probe in the hybridization methods described herein. PNA is a DNA mimic having a peptide-like, inorganic backbone, such as N-(2-aminoethyl) glycine units, with an organic base (A, G, C, T or U) attached to the glycine nitrogen via a methylene carbonyl linker (see, for example, 1994, Nielsen et al., Bioconjugate Chemistry 5:1). The PNA probe can be designed to specifically hybridize to a nucleic acid sequence comprising one or more mutations of interest. Hybridization of the PNA probe to a nucleic acid sequence is indicative of the presence of the mutation of interest.

In another embodiment of the methods of the invention, mutation analysis by restriction digestion can be used to detect a gene, or mutant gene, associated neoplasia, including meningioma, if the mutation results in the creation or elimination of a restriction site. A sample containing nucleic acid from the subject is used. Polymerase chain reaction (PCR) can be used to amplify all or a fragment of a nucleic acid (and, if necessary, the flanking sequences) in the sample. RFLP analysis is conducted as described (see Current Protocols in Molecular Biology, supra). The digestion pattern of the relevant fragments indicates the presence or absence of mutation in gene, or mutant gene, associated with neoplasia.

Direct sequence analysis can also be used to detect specific mutations in a gene associated with neoplasia. A sample comprising DNA or RNA can be used, and PCR or other appropriate methods can be used to amplify all or a fragment of the nucleic acid, and/or its flanking sequences, if desired. The sequence, or a fragment thereof (e.g., one or more exons), or cDNA, or fragment of the cDNA, or mRNA, or fragment of the mRNA, is determined, using standard methods. The sequence of the gene, gene fragment, cDNA, cDNA fragment, mRNA, or mRNA fragment is compared with the known nucleic acid sequence of gene of interest, as appropriate. The presence or absence of a mutation can then be identified.

Allele-specific oligonucleotides can also be used to detect the presence of a mutation in gene associated with neoplasia, through, for example, the use of dot-blot hybridization of amplified oligonucleotides with allele-specific oligonucleotide (ASO) probes (see, for example, 1986, Saiki et al., Nature 324:163-166). An "allele-specific oligonucleotide" (also referred to herein as an "allele-specific oligonucleotide probe") is an oligonucleotide of approximately 10-50 base pairs, preferably approximately 15-30 base pairs, that specifically hybridizes to the mutant sequence, and that contains a mutation. An allele-specific oligonucleotide probe that is specific for a particular mutation can be prepared, using standard methods (see Current Protocols in Molecular Biology, supra). To identify a mutation, a sample comprising nucleic acid is used. PCR can be used to amplify all or a fragment of the test nucleic acid sequence. The nucleic acid containing the amplified sequence (or fragment thereof) is dot-blotted, using standard methods (see Sambrook et al. (2012, Molecular Cloning: A Laboratory Manual, Cold Spring Harbor Laboratory, New York), and Ausubel et al. (1997, Current Protocols in Molecular Biology, John Wiley & Sons, New York)), and the blot is contacted with the oligonucleotide probe. The presence of specific hybridization of the probe to the amplified nucleic acid is then detected. Specific hybridization of an allele-specific oligonucleotide probe containing the mutation of interest, to test nucleic acid from the subject is indicative of the presence of the mutation of interest.

In another embodiment of the invention, fluorescence resonance energy transfer (FRET) can be used to detect the presence of a mutation. FRET is the process of a distance-dependent excited state interaction in which the emission of one fluorescent molecule is coupled to the excitation of another. A typical acceptor and donor pair for resonance energy transfer consists of 4-[[4-(dimethylamino) phenyl] azo]benzoic acid (DABCYL) and 5-[(2-aminoethylamino] naphthalene sulfonic acid (EDANS). EDANS is excited by illumination with 336 nm light, and emits a photon with wavelength 490 nxn. If a DABCYL moiety is located within 20 angstroms of the EDANS, this photon will be efficiently absorbed. DABCYL and MANS will be attached to two different oligonucleotide probes designed to hybridize head-to-tail to nucleic acid adjacent to and/or overlapping the site of one of the mutations of interest. Melting curve analysis is then applied: cycles of denaturation, cooling, and re-heating are applied to a test sample mixed with the oligonucleotide probes, and the fluorescence is continuously monitored to detect a decrease in DABCYL fluorescence or an increase in EDANS fluorescence (loss of quenching). While the two probes remain hybridized adjacent to one another, FRET will be very efficient. Physical separation of the oligonucleotide probes results in inefficient FRET, as the two dyes are no longer in close proximity. The presence or absence of a mutation of interest can be assessed by comparing the fluorescence intensity profile obtained from the test sample, to fluorescence intensity profiles of control samples comprising known mutations of interest.

In another embodiment, arrays of oligonucleotide probes that are complementary to target nucleic acid sequence segments from a subject can be used to identify mutations in a gene associated with neoplasia. For example, in one embodiment, an oligonucleotide array can be used. Oligonucleotide arrays typically comprise a plurality of different oligonucleotide probes that are coupled to a surface of a substrate in different known locations. These oligonucleotide arrays, also known as "Genechips," have been generally described in the art, for example, U.S. Pat. No. 5,143,854 and PCT patent publication Nos. WO 90/15070 and 92/10092. These arrays can generally be produced using mechanical synthesis methods or light directed synthesis methods which incorporate a combination of photolithographic methods and solid phase oligonucleotide synthesis methods. See Fodor et al., Science, 251:767-777 (1991), Pirrung et al., U.S. Pat. No. 5,143,854 (see also PCT Application No. WO 90/15070) and Fodor et al., PCT Publication No. WO 92/10092 and U.S. Pat. No. 5,424,186. Techniques for the synthesis of these arrays using mechanical synthesis methods are described in, e.g., U.S. Pat. No. 5,384,261.

After an oligonucleotide array is prepared, a nucleic acid of interest is hybridized with the array and scanned for mutations. Hybridization and scanning are generally carried out by methods described herein and also in, e.g., Published PCT Application Nos. WO 92/10092 and WO 95/11995, and U.S. Pat. No. 5,424,186, the entire teachings of which are incorporated by reference herein. In brief, a target nucleic acid sequence which includes one or more previously identified mutations or markers is amplified by well-known amplification techniques, e.g., PCR. Typically, this involves the use of primer sequences that are complementary to the two strands of the target sequence both upstream and downstream of the mutation. Asymmetric PCR techniques may also be used. Amplified target, generally incorporating a label, is then hybridized with the array under appropriate conditions. Upon completion of hybridization and washing of the array, the array is scanned to determine the position on the array to which the target sequence hybridizes. The hybridization data obtained from the scan is typically in the form of fluorescence intensities as a function of location on the array.

Although often described in terms of a single detection block (e.g., for detection of a single mutation), arrays can include multiple detection blocks, and thus be capable of analyzing multiple, specific mutations. In alternate arrangements, it will generally be understood that detection blocks may be grouped within a single array or in multiple, separate arrays so that varying, optimal conditions may be used during the hybridization of the target to the array. This allows for the separate optimization of hybridization conditions for each situation. Additional description of use of oligonucleotide arrays for detection of polymorphisms can be found, for example, in U.S. Pat. Nos. 5,858,659 and 5,837,832, the entire teachings of which are incorporated by reference herein.

Other methods of nucleic acid analysis can be used to detect mutations of interest in genes associated with neoplasia. Representative methods include direct manual sequencing (1988, Church and Gilbert, Proc. Natl. Acad. Sci. USA 81:1991-1995; 1977, Sanger et al., Proc. Natl. Acad. Sci. 74:5463-5467; Beavis et al. U.S. Pat. No. 5,288, 644); automated fluorescent sequencing; single-stranded conformation polymorphism assays (SSCP); clamped denaturing gel electrophoresis (CDGE); denaturing gradient gel electrophoresis (DGGE) (1981, Sheffield et al., Proc. Natl. Acad. Sci. USA 86:232-236), mobility shift analysis (1989, Orita et al., Proc. Natl. Acad. Sci. USA 86:2766-2770; 1987, Rosenbaum and Reissner, Biophys. Chem. 265:1275; 1991, Keen et al., Trends Genet. 7:5); restriction enzyme analysis (1978, Flavell et al., Cell 15:25; 1981, Geever, et al., Proc. Natl. Acad. Sci. USA 78:5081); heteroduplex analysis; chemical mismatch cleavage (CMC) (1985, Cotton et al., Proc. Natl. Acad. Sci. USA 85:4397-4401); RNase protection assays (1985, Myers, et al., Science 230:1242); use of polypeptides which recognize nucleotide mismatches, such as E. coli mutS protein (see, for example, U.S. Pat. No. 5,459,039); Luminex xMAP™ technology; high-throughput sequencing (HTS) (2011, Gundry and Vijg, Mutat Res, doi: 10.1016/j.mrfmmm.2011.10.001); next-generation sequencing (NGS) (2009, Voelkerding et al., Clinical Chemistry 55:641-658; 2011, Su et al., Expert Rev Mol Diagn. 11:333-343; 2011, Ji and Myllykangas, Biotechnol Genet Eng Rev 27:135-158); ion semiconductor sequencing (2011, Rusk, Nature Methods doi: 10. 1038/nmeth.f.330; 2011, Rothberg et al., Nature 475:348-352) and/or allele-specific PCR, for example. These and other methods can be used to identify the presence of one or more mutations of interest in the genes associated with neoplasia, including meningioma, in a biological sample obtained from a subject. In one embodiment of the invention, the methods of assessing a biological sample for the presence or absence of a mutation in a gene associated with neoplasia, as described herein, are used to diagnose in a subject a mutation in a gene associated with neoplasia. Furthermore, one, or more than one mutation may be found.

The probes and primers according to the invention can be labeled directly or indirectly with a radioactive or nonradioactive compound, by methods well known to those skilled in the art, in order to obtain a detectable and/or quantifiable signal; the labeling of the primers or of the probes according to the invention is carried out with radioactive elements or with nonradioactive molecules. Among the radioactive isotopes used, mention may be made of $^{32}P$, $^{33}P$, $^{35}S$ or $^{3}H$. The nonradioactive entities are selected from ligands such as biotin, avidin, streptavidin or digoxigenin, haptenes, dyes, and luminescent agents such as radioluminescent, chemoluminescent, bioluminescent, fluorescent or phosphorescent agents.

Nucleic acids can be obtained from the cells using known techniques. Nucleic acid herein refers to RNA, including mRNA, and DNA, including genomic DNA. The nucleic acid can be double-stranded or single-stranded (i.e., a sense or an antisense single strand) and can be complementary to a nucleic acid encoding a polypeptide. The nucleic acid content may also be an RNA o DNA extraction performed on a fresh or fixed tissue sample.

Routine methods also can be used to extract genomic DNA from a tissue sample, including, for example, phenol extraction. Alternatively, genomic DNA can be extracted with kits such as the QIAamp™. Tissue Kit (Qiagen, Chatsworth, Calif.), the Wizard™ Genomic DNA purification kit (Promega, Madison, Wis.), the Puregene DNA Isolation System (Gentra Systems, Inc., Minneapolis, Minn.), and the A.S.A.P.™ Genomic DNA isolation kit (Boehringer Mannheim, Indianapolis, Ind.).

There are many methods known in the art for the detection of specific nucleic acid sequences and new methods are continually reported. A great majority of the known specific nucleic acid detection methods utilize nucleic acid probes in specific hybridization reactions. Preferably, the detection of hybridization to the duplex form is a Southern blot technique. In the Southern blot technique, a nucleic acid sample is separated in an agarose gel based on size (molecular weight) and affixed to a membrane, denatured, and exposed to (admixed with) the labeled nucleic acid probe under hybridizing conditions. If the labeled nucleic acid probe forms a hybrid with the nucleic acid on the blot, the label is bound to the membrane.

In the Southern blot, the nucleic acid probe is preferably labeled with a tag. That tag can be a radioactive isotope, a fluorescent dye or the other well-known materials. Another type of process for the specific detection of nucleic acids of exogenous organisms in a body sample known in the art are the hybridization methods as exemplified by U.S. Pat. Nos. 6,159,693 and 6,270,974, and related patents. To briefly summarize one of those methods, a nucleic acid probe of at least 10 nucleotides, preferably at least 15 nucleotides, more preferably at least 25 nucleotides, having a sequence complementary to a desired region of the gene, or mutant gene, of interest is hybridized in a sample, subjected to depolymerizing conditions, and the sample is treated with an ATP/luciferase system, which will luminesce if the nucleic sequence is present. In quantitative Southern blotting, levels of the mutant gene can be compared to wild-type levels of the gene.

A further process for the detection of hybridized nucleic acid takes advantage of the polymerase chain reaction (PCR). The PCR process is well known in the art (U.S. Pat. Nos. 4,683,195, 4,683,202, and 4,800,159). To briefly summarize PCR, nucleic acid primers, complementary to opposite strands of a nucleic acid amplification target sequence, are permitted to anneal to the denatured sample. A DNA polymerase (typically heat stable) extends the DNA duplex from the hybridized primer. The process is repeated to amplify the nucleic acid target. If the nucleic acid primers do not hybridize to the sample, then there is no corresponding amplified PCR product. In this case, the PCR primer acts as a hybridization probe.

In PCR, the nucleic acid probe can be labeled with a tag as discussed before. Most preferably the detection of the duplex is done using at least one primer directed to a RS. In yet another embodiment of PCR, the detection of the hybridized duplex comprises electrophoretic gel separation followed by dye-based visualization.

DNA amplification procedures by PCR are well known and are described in U.S. Pat. No. 4,683,202. Briefly, the primers anneal to the target nucleic acid at sites distinct from one another and in an opposite orientation. A primer annealed to the target sequence is extended by the enzymatic action of a heat stable DNA polymerase. The extension product is then denatured from the target sequence by heating, and the process is repeated. Successive cycling of this procedure on both DNA strands provides exponential amplification of the region flanked by the primers.

Amplification is then performed using a PCR-type technique, that is to say the PCR technique or any other related technique. Two primers, complementary to the gene, or mutant gene, associated with neoplasia are then added to the nucleic acid content along with a polymerase, and the polymerase amplifies the DNA region between the primers.

The expression specifically hybridizing in stringent conditions refers to a hybridizing step in the process of the invention where the oligonucleotide sequences selected as probes or primers are of adequate length and sufficiently unambiguous so as to minimize the amount of non-specific binding that may occur during the amplification. The oligonucleotide probes or primers herein described may be prepared by any suitable methods such as chemical synthesis methods.

Hybridization is typically accomplished by annealing the oligonucleotide probe or primer to the DNA under conditions of stringency that prevent non-specific binding but permit binding of this DNA which has a significant level of homology with the probe or primer. Among the conditions of stringency is the melting temperature (Tm) for the amplification step using the set of primers, which is in the range of about 55° C. to about 70° C. Preferably, the Tm for the amplification step is in the range of about 59° C. to about 72° C. Most preferably, the Tm for the amplification step is about 60° C. Typical hybridization and washing stringency conditions depend in part on the size (i.e., number of nucleotides in length) of the DNA or the oligonucleotide probe, the base composition and monovalent and divalent cation concentrations (Ausubel et al., 1994, eds Current Protocols in Molecular Biology).

In a preferred embodiment, the process for determining the quantitative and qualitative profile according to the present invention is characterized in that the amplifications are real-time amplifications performed using a labeled probe, preferably a labeled hydrolysis-probe, capable of specifically hybridizing in stringent conditions with a segment of a gene, or mutant gene, associated with neoplasia. The labeled probe is capable of emitting a detectable signal every time each amplification cycle occurs.

The real-time amplification, such as real-time PCR, is well known in the art, and the various known techniques will be employed in the best way for the implementation of the present process. These techniques are performed using various categories of probes, such as hydrolysis probes, hybridization adjacent probes, or molecular beacons. The techniques employing hydrolysis probes or molecular beacons are based on the use of a fluorescence quencher/reporter system, and the hybridization adjacent probes are based on the use of fluorescence acceptor/donor molecules.

Hydrolysis probes with a fluorescence quencher/reporter system are available in the market, and are for example commercialized by the Applied Biosystems group (USA). Many fluorescent dyes may be employed, such as FAM dyes (6-carboxy-fluorescein), or any other dye phosphoramidite reagents.

In another preferred embodiment, the process for determining the quantitative and qualitative profile according to the present invention is characterized in that the amplification products can be elongated, wherein the elongation products are separated relative to their length. The signal obtained for the elongation products is measured, and the quantitative and qualitative profile of the labeling intensity relative to the elongation product length is established.

The elongation step, also called a run-off reaction, allows one to determine the length of the amplification product. The length can be determined using conventional techniques, for example, using gels such as polyacrylamide gels for the separation, DNA sequencers, and adapted software. Because some mutations display length heterogeneity, some mutations can be determined by a change in length of elongation products.

In one aspect, the invention includes a primer that is complementary to a nucleic acid sequence flanking the mutation of interest, and more particularly the primer includes 12 or more contiguous nucleotides substantially complementary to the sequence flanking the mutation of interest. Preferably, a primer featured in the invention includes a nucleotide sequence sufficiently complementary to hybridize to a nucleic acid sequence of about 12 to 25 nucleotides. More preferably, the primer differs by no more than 1, 2, or 3 nucleotides from the target flanking nucleotide sequence In another aspect, the length of the primer can vary in length, preferably about 15 to 28 nucleotides in length (e.g., 16, 17, 18, 19, 20, 21, 22, 23, 24, 25, 26, or 27 nucleotides in length).

The present invention also pertains to kits useful in the methods of the invention. Such kits comprise components useful in any of the methods described herein, including for example, hybridization probes or primers (e.g., labeled probes or primers), reagents for detection of labeled molecules, restriction enzymes (e.g., for RFLP analysis), allele-specific oligonucleotides, means for amplification of subject's nucleic acids, or means for analyzing the nucleic acid sequence of the gene of interest and instructional materials. For example, in one embodiment, the kit comprises components useful for analysis of mutations associated with neoplasia. In a preferred embodiment of the invention, the kit comprises components for detecting one or more of the mutations of associated with neoplasia, including meningioma, as elsewhere described herein.

Therapeutic Compositions and Methods

In various embodiments, the present invention includes compositions and methods of treating pathologies associated with neoplasia, including meningioma, by diminishing the expression level or activity level mutant gene, the expression of which mutant gene is associated with neoplasia. It will be understood by one skilled in the art, based upon the disclosure provided herein, that a decrease in the level of a mutant gene associated with neoplasia, encompasses the decrease in expression of the mutant gene associated with neoplasia. Additionally, the skilled artisan will appreciate, once armed with the teachings of the present invention, that a decrease in the level of a gene, or mutant gene, associated with neoplasia, includes a decrease in the activity of a gene, or mutant gene, associated with neoplasia. Thus, decreasing the level or activity of a mutant gene, the expression of which mutant gene is associated with neoplasia, including meningioma, includes, but is not limited to, decreasing transcription, translation, or both, of a nucleic acid encoding a gene, or mutant gene, associated with neoplasia; and it also includes decreasing any activity of the gene, or mutant gene, associated with neoplasia, as well. In various embodiments, the gene having a mutation associated with neoplasia is at least one of NF2, TRAF7, AKT1, KLF4, SMO, PIK3CA, PIK3R1, BRCA1, CREBBP, SMARCB1 and PRKAR1A.

Inhibition of the gene, or mutant gene, associated with neoplasia, including meningioma, can be assessed using a wide variety of methods, including those disclosed herein, as well as methods well-known in the art or to be developed in the future. That is, the routineer will appreciate, based upon the disclosure provided herein, that decreasing the level or activity of a gene, or mutant gene, associated with neoplasia, can be readily assessed using methods that assess the level of a nucleic acid encoding the gene, or mutant gene, associated with neoplasia (e.g., mRNA) and/or the level of protein encoded by the gene, or mutant gene, associated with neoplasia, present in a biological sample.

One skilled in the art, based upon the disclosure provided herein, would understand that the compositions and methods of the invention are useful in treating pathologies associated with neoplasia, including meningioma, in subjects who have neoplasia, whether or not the subject is also being treated with other medication or chemotherapy. Further, the skilled artisan will further appreciate, based upon the teachings provided herein, that the pathologies associated with neoplasia treatable by the compositions and methods described herein encompass any pathology associated with neoplasia, including meningioma, where at least one of the genes NF2, TRAF7, AKT1, KLF4, SMO, PIK3CA, PIK3R1, BRCA1, CREBBP, SMARCB1 and PRKAR1A plays a role.

An inhibitor composition of the invention can include, but should not be construed as being limited to, a chemical compound, a protein, a peptide, a peptidomemetic, an antibody, a ribozyme, a small molecule chemical compound, and an antisense nucleic acid molecule (e.g., siRNA, miRNA, etc.). One skilled in the art would readily appreciate, based on the disclosure provided herein, that an inhibitor composition encompasses a chemical compound that decreases the level or activity of a gene, or mutant gene, associated with neoplasia. Additionally, an inhibitor composition encompasses a chemically modified compound, and derivatives, as is well known to one skilled in the chemical arts.

Further, one skilled in the art would, when equipped with this disclosure and the methods exemplified herein, appreciate that an inhibitor composition includes such inhibitors as discovered in the future, as can be identified by well-known criteria in the art of pharmacology, such as the physiological results of inhibition of a gene, or mutant gene, associated with neoplasia, as described in detail herein and/or as known in the art. Therefore, the present invention is not limited in any way to any particular inhibitor as exemplified or disclosed herein; rather, the invention encompasses those inhibitors that would be understood by the routineer to be useful as are known in the art and as are discovered in the future.

Further methods of identifying and producing an inhibitor composition are well known to those of ordinary skill in the art, including, but not limited, obtaining an inhibitor from a naturally occurring source (i.e., *Streptomyces* sp., *Pseudomonas* sp., *Stylotella aurantium*). Alternatively, an inhibitor composition can be synthesized chemically. Further, the routineer would appreciate, based upon the teachings provided herein, that an inhibitor composition can be obtained from a recombinant organism. Compositions and methods for chemically synthesizing inhibitor compositions and for obtaining them from natural sources are well known in the art and are described in the art.

One skilled in the art will appreciate that an inhibitor can be administered as a small molecule chemical, a protein, a nucleic acid construct encoding a protein, an antisense nucleic acid, a nucleic acid construct encoding an antisense nucleic acid, or combinations thereof. Numerous vectors and other compositions and methods are well known for administering a protein or a nucleic acid construct encoding a protein to cells or tissues. Therefore, the invention includes a method of administering a protein or a nucleic acid encoding a protein that is an inhibitor of a gene, or mutant gene, associated with neoplasia. (Sambrook et al., 1989, Molecular Cloning: A Laboratory Manual, Cold Spring Harbor Laboratory, New York; Ausubel et al., 1997, Current Protocols in Molecular Biology, John Wiley & Sons, New York).

One skilled in the art will realize that diminishing the amount or activity of a gene, or mutant gene, that itself increases the amount or activity of a gene, or mutant gene, associated with neoplasia, can serve in the compositions and methods of the present invention to decrease the amount or activity of the gene, or mutant gene, associated with neoplasia. Therefore, inhibitor compositions that inhibit the amount or activity of a modulator of a gene, or mutant gene, associated with neoplasia, are included in the compositions and methods of the invention. In various embodiments, the gene having a mutation associated with neoplasia is at least one of NF2, TRAF7, AKT1, KLF4, SMO, PIK3CA, PIK3R1, BRCA1, CREBBP, SMARCB1 and PRKAR1A.

One skilled in the art will also realize that increasing the amount or activity of a gene, or mutant gene, that itself decreases the amount or activity of a gene, or mutant gene, associated with neoplasia, including meningioma, can serve in the compositions and methods of the present invention to decrease the amount or activity of the gene, or mutant gene, associated with neoplasia. Therefore, activator compositions that activate the amount or activity of a modulator of a gene, or mutant gene, associated with neoplasia, are included in the compositions and methods of the invention. In various embodiments, the gene having a mutation associated with neoplasia is at least one of NF2, TRAF7, AKT1, KLF4, SMO, PIK3CA, PIK3R1, BRCA1, CREBBP, SMARCB1 and PRKAR1A.

One skilled in the art will realize that diminishing the amount or activity of a gene, or mutant gene, that itself is an effector of a gene, or mutant gene, associated with neoplasia, including meningioma, can serve in the compositions and methods of the present invention to decrease the amount or activity of the gene, or mutant gene, associated with neoplasia. Therefore, inhibitor compositions that inhibit the amount or activity of an effector of a gene, or mutant gene, associated with neoplasia, are included in the compositions and methods of the invention. In various embodiments, the gene having a mutation associated with neoplasia is at least one of NF2, TRAF7, AKT1, KLF4, SMO, PIK3CA, PIK3R1, BRCA1, CREBBP, SMARCB 1 and PRKAR1A.

Antisense oligonucleotides are DNA or RNA molecules that are complementary to some portion of an mRNA molecule. When present in a cell, antisense oligonucleotides hybridize to an existing mRNA molecule and inhibit translation into a gene product. Inhibiting the expression of a gene using an antisense oligonucleotide is well known in the art (Marcus-Sekura, 1988, Anal. Biochem. 172:289), as are methods of expressing an antisense oligonucleotide in a cell (Inoue, U.S. Pat. No. 5,190,931). The compositions and methods of the invention include the use of an antisense oligonucleotide to diminish the level of a gene, or mutant gene, associated with neoplasia.

The compositions and methods of the invention also include the use of an antisense oligonucleotide to diminish the level of an activating modulator of the gene, or mutant gene, associated with neoplasia, thereby causing a decrease in the amount or activity of the gene, or mutant gene, associated with neoplasia.

Contemplated in the present invention are antisense oligonucleotides that are synthesized and provided to a cell by way of methods well known to those of ordinary skill in the art. As an example, an antisense oligonucleotide can be synthesized to be between about 10 and about 100, more preferably between about 15 and about 50 nucleotides long. The synthesis of nucleic acid molecules is well known in the art, as is the synthesis of modified antisense oligonucleotides to improve biological activity in comparison to unmodified antisense oligonucleotides (Tullis, 1991, U.S. Pat. No. 5,023,243).

Similarly, the expression of a gene may be inhibited by the hybridization of an antisense molecule to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

Alternatively, inhibition of a gene, or mutant gene, associated with neoplasia, or of a activating modulator of the gene, or mutant gene, associated with neoplasia, can be accomplished through the use of a ribozyme. Using ribozymes for inhibiting gene expression is well known to those of skill in the art (see, e.g., Cech et al., 1992, J. Biol. Chem. 267:17479; Hampel et al., 1989, Biochemistry 28: 4929; Altman et al., U.S. Pat. No. 5,168,053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn. 260:3030), allowing the selective cleavage of specific mRNA molecules. Given the nucleotide sequence of the molecule, one of ordinary skill in the art could synthesize an antisense oligonucleotide or ribozyme without undue experimentation, provided with the disclosure and references incorporated herein.

One skilled in the art will appreciate that inhibitors of a gene, or mutant gene, associated with neoplasia, such as meningioma, can be administered singly or in any combination. Further, inhibitors can be administered singly or in any combination in a temporal sense, in that they may be administered simultaneously, before, and/or after each other. One of ordinary skill in the art will appreciate, based on the disclosure provided herein, that inhibitors can be used to treat pathologies associated with neoplasia, and that an inhibitor can be used alone or in any combination with another inhibitor to effect a therapeutic result.

It will be appreciated by one skilled in the art, when armed with the present disclosure including the methods detailed herein, that the invention is not limited to treatment of a pathology associated with neoplasia that is already established. Particularly, the pathology need not have manifested to the point of detriment to the subject; indeed, the pathology need not be detected in a subject before treatment is administered. That is, significant pathology associated with neoplasia does not have to occur before the present invention may provide benefit. Therefore, the present invention includes a method for preventing a pathology associated with neoplasia in a subject, in that an inhibitor, as discussed previously elsewhere herein, can be administered to a subject prior to the onset of a pathology, thereby preventing the pathology. The preventive methods described herein also include the treatment of a subject that is in remission for the prevention of a recurrence of neoplasia.

One skilled in the art, when armed with the disclosure herein, would appreciate that the prevention of a pathology associated with neoplasia encompasses administering to a subject an inhibitor as a preventative measure against a pathology associated with neoplasia.

The invention encompasses administration of an inhibitor composition to practice the methods of the invention; the skilled artisan would understand, based on the disclosure provided herein, how to formulate and administer the appropriate inhibitor compositions to a subject. However, the present invention is not limited to any particular method of administration or treatment regimen.

Pharmaceutical Compositions

Compositions identified as potential useful compounds for treatment and/or prevention of neoplasia, such as meningioma, can be formulated and administered to a subject for treatment of neoplasia, as now described.

The invention encompasses the preparation and use of pharmaceutical compositions comprising a composition useful for treatment of neoplasia, including meningioma, disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically-acceptable carrier" means a chemical composition with which an appropriate inhibitor thereof, may be combined and which, following the combination, can be used to administer the appropriate inhibitor thereof, to a subject.

The pharmaceutical compositions useful for practicing the invention may be administered to deliver a dose of between about 0.1 ng/kg/day and 100 mg/kg/day.

In various embodiments, the pharmaceutical compositions useful in the methods of the invention may be administered, by way of example, systemically, parenterally, or topically, such as, in oral formulations, inhaled formulations, including solid or aerosol, and by topical or other similar formulations. In addition to the appropriate therapeutic composition, such pharmaceutical compositions may contain pharmaceutically acceptable carriers and other ingredients known to enhance and facilitate drug administration. Other possible formulations, such as nanoparticles, liposomes, resealed erythrocytes, and immunologically based systems may also be used to administer an appropriate inhibitor thereof, according to the methods of the invention.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation.

Pharmaceutical compositions that are useful in the methods of the invention may be prepared, packaged, or sold in formulations suitable for oral, rectal, vaginal, parenteral, topical, pulmonary, intranasal, buccal, intravenous, ophthalmic, intrathecal and other known routes of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and U.S. Pat. No. 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as *arachis*, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent.

Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as *arachis*, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or *arachis* oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, cutaneous, subcutaneous, intraperitoneal, intravenous, intramuscular, intracistemal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares. Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, contain 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

Typically dosages of the compound of the invention which may be administered to an animal, preferably a human, range in amount from about 0.01 mg to 20 about 100 g per kilogram of body weight of the animal. While the precise dosage administered will vary depending upon any number of factors, including, but not limited to, the type of animal and type of disease state being treated, the age of the animal and the route of administration. Preferably, the dosage of the compound will vary from about 1 mg to about 100 mg per kilogram of body weight of the animal. More preferably, the dosage will vary from about 1 µg to about 1 g per kilogram of body weight of the animal. The compound can be administered to an animal as frequently as several times daily, or it can be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

Induced Pluripotent Stem Cells

The present invention also provides induced pluripotent stem (iPS) cells derived by nuclear reprogramming of a somatic cell and their method of use, as well as methods of reprogramming of a differentiated cell without using eggs, embryos, or embryonic stem (ES) cells. As further discussed herein, the present invention also provides various nuclear reprogramming factors capable of generating pluripotent stem cells from somatic cells. The nuclear reprogramming factor may comprise one or more gene products. The nuclear reprogramming factor may also comprise a combination of gene products. Each nuclear reprogramming factor may be used alone or in combination with other nuclear reprogramming factors as disclosed elsewhere herein. In addition, nuclear reprogramming may be performed with small molecules, compounds, or other agents such that iPS cells are obtained.

In a preferred embodiment, the nuclear reprogramming factor comprises a gene product of at least one of Oct3/4, mutant KLF4, Myc, and Sox2. In some embodiments, the mutant KLF4 has the mutation K409Q.

The present invention also provides a nuclear reprogramming factor comprising any combination of gene products, small molecules and/or substances as described herein, further comprising one or more factors improving the efficiency of iPS cell induction.

In another embodiment, the present invention is a method for preparing an induced pluripotent stem cell by nuclear reprogramming of a somatic cell, which comprises the step of contacting the nuclear reprogramming factor of the invention with the somatic cell. In some embodiments, the method comprises the step of adding the at least one nuclear reprogramming factor to a culture of the somatic cell. In some embodiments, the method comprises the step of introducing a gene encoding the at least one nuclear reprogramming factor into the somatic cell. In some embodiments, the method comprises the step of introducing the at least one nuclear reprogramming factor gene into the somatic cell by using a recombinant vector containing at least one kind of gene encoding the at least one nuclear reprogramming factor. In some embodiments, the method comprises the step of introducing the at least one nuclear reprogramming factor gene into the somatic cell by using an transiently expresses nucleic acid (e.g., plasmid, mRNA) containing at least one kind of gene encoding the at least one nuclear reprogramming factor. In some embodiments, the method comprises a somatic cell isolated from a patient as the somatic cell.

In another embodiment, the present invention provides an induced pluripotent stem cell obtained by the methods described herein. The present invention also provides a somatic cell derived by inducing differentiation of the induced pluripotent stem cell obtained by the methods described herein.

By using the nuclear reprogramming factor provided by the present invention, reprogramming of a differentiated cell nucleus can be conveniently and highly reproducibly induced without using embryos or ES cells, and an induced pluripotent stem cell, as an undifferentiated cell having differentiation ability, pluripotency, and growth ability similar to those of ES cells, can be established. For example, an induced pluripotent stem cell having high growth ability and differentiation pluripotency can be prepared from a patient's own somatic cell by using at least one nuclear reprogramming factor of the present invention. Cells obtainable by differentiating said cell (for example, cardiac muscle cells, insulin producing cells, nerve cells and the like) are extremely useful, because they can be utilized for stem cell transplantation therapies for a variety of diseases such as cardiac insufficiency, insulin dependent diabetes mellitus, Parkinson's disease and spinal cord injury. Further, various cells obtainable by differentiating the induced pluripotent stem cell (for example, cardiac muscle cells, hepatic cells and the like) are highly useful as systems for evaluating efficacy or toxicity of compounds, medicaments, poisons and the like.

Other components of the methods described which may be included in the nuclear reprogramming methods of the present invention can found as described in U.S. Pat. No. 8,058,065, which is incorporated herein by reference in its entirety for all purposes.

By using the nuclear reprogramming factor of the present invention, the nucleus of a somatic cell can be reprogrammed to obtain an induced pluripotent stem cell. The term "induced pluripotent stem cells" means cells having properties similar to those of ES cells, and more specifically, the term encompasses undifferentiated cells having pluripotency and growth ability. However, the term should not be construed narrowly in any sense, and should be construed in the broadest sense. The method for preparing induced pluripotent stem cells by using a nuclear reprogramming factor is explained in International Publication WO2005/80598 and a means for isolating induced pluripotent stem cells is also specifically explained. Therefore, by referring to the aforementioned publication, those skilled in the art can easily prepare induced pluripotent stem cells by using the at least one nuclear reprogramming factor of the present invention. Methods for preparing induced pluripotent stem cells from somatic cells by using the at least one nuclear reprogramming factor of the present invention are not particularly limited. Any method may be employed as long as the nuclear reprogramming factor can contact with somatic cells under an environment in which the somatic cells and induced pluripotent stem cells can proliferate. An advantage of the present invention is that an induced pluripotent stem cell can be prepared by contacting a nuclear reprogramming factor with a somatic cell in the absence of eggs, embryos, or embryonic stem (ES) cells.

For example, a gene product contained in the at least one nuclear reprogramming factor of the present invention may be added to a medium. Alternatively, by using a vector containing a gene that is capable of expressing the at least one nuclear reprogramming factor of the present invention, a means of transducing said gene into a somatic cell may be employed. When such vector is used, two or more kinds of genes may be incorporated into the vector, and each of the gene products may be simultaneously expressed in a somatic cell. When one or more of the gene products contained in the nuclear reprogramming factor of the present invention are already expressed in a somatic cell to be reprogrammed, said gene products may be excluded from the nuclear reprogramming factor of the present invention. It is understood that such embodiments fall within the scope of the present invention.

The at least one nuclear reprogramming factor of the present invention can be used to generate iPS cells from differentiated adult somatic cells. In the preparation of induced pluripotent stem cells by using the nuclear reprogramming factor of the present invention, types of somatic cells to be reprogrammed are not particularly limited, and any kind of somatic cells may be used. For example, matured somatic cells may be used, as well as somatic cells of an embryonic period. Other examples of cells capable of being generated into iPS cells and/or encompassed by the present invention include mammalian cells such as fibroblasts, B cells, T cells, dendritic cells, ketatinocytes, adipose cells, epithelial cells, epidermal cells, chondrocytes, cumulus cells, neural cells, glial cells, astrocytes, cardiac cells, esophageal cells, muscle cells, melanocytes, hematopoietic cells, pancreatic cells, hepatocytes, macrophages, monocytes, mononuclear cells, and gastric cells, including gastric epithelial cells. The cells can be embryonic, or adult somatic cells, differentiated cells, cells with an intact nuclear membrane, non-dividing cells, quiescent cells, terminally differentiated primary cells, and the like.

When induced pluripotent stem cells are used for therapeutic treatment of diseases, it is desirable to use somatic cells isolated from patients. For example, somatic cells involved in diseases, somatic cells participating in therapeutic treatment of diseases and the like can be used. A method for selecting induced pluripotent stem cells that appear in a medium according to the method of the present invention is not particularly limited, and a well-known means may be suitably employed, for example, a drug resistance gene or the like can be used as a marker gene to isolate induced pluripotent stem cells using drug resistance as an index. Various media that can maintain undifferentiated state and pluripotency of ES cells and various media which cannot maintain such properties are known in this field, and induced pluripotent stem cells can be efficiently isolated by using a combination of appropriate media. Differentiation and proliferation abilities of isolated induced pluripotent stem cells can be easily confirmed by those skilled in the art by using confirmation means widely applied to ES cells.

Thus, another embodiment of the invention comprises a pluripotent stem cell induced by reprogramming a somatic cell in the absence of eggs, embryos, or embryonic stem (ES) cells. The pluripotent stem cell can be a mammalian cell, for example a mouse, human, rat, bovine, ovine, horse, hamster, dog, guinea pig, or ape cell. For example, direct reprogramming of somatic cells provides an opportunity to generate patient- or disease-specific pluripotent stem cells.

The present invention also provides for the generation of somatic cells derived by inducing differentiation of the pluripotent stem cells derived from the methods described herein. The present invention thus provides a somatic cell derived by inducing differentiation of the induced pluripotent stem cell derived by the methods described herein.

In another embodiment, there is disclosed a method for improving differentiation ability and/or growth ability of a cell, which comprises contacting at least one nuclear reprogramming factor with a cell.

In a particularly preferred embodiment, the present invention comprises a method for stem cell therapy comprising: isolating and collecting a somatic cell from a patient; inducing the somatic cell from the patient into an iPS cell; (3) inducing differentiation of the iPS cell, and (4) transplanting the cell differentiated for the iPS cell into the patient.

In preferred embodiment, the present invention includes a method for evaluating a physiological function of a compound comprising treating cells obtained by inducing differentiation of an induced pluripotent stem cell with the compound.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: The Novel Neoplasia Genes. TRAF7 and KLF4, Along with SMO and AKT1, Define Clinically Distinct Meningiomas Meningiomas are the most common primary brain tumors. While typically of benign histology, they can be associated with significant neurological morbidity and have the potential for malignant transformation. Reported herein is a genomic analysis of 300 meningiomas using whole-exome and targeted next-generation sequencing leading to the identification of driver mutations in two genes, TRAF7 and KLF4, not previously known to play a role in neoplasia. Three known-neoplasia genes, NF2, AKT1 or SMO, were also found to contribute to meningioma formation. Non-NF2 tumors were typically benign, showed chromosomal stability and localized to the medial skull base. In contrast, NF2 mutant meningiomas showed genomic instability, increased risk for malignancy and localized to the cerebral and cerebellar hemispheres. Gene expression and ChIP-seq analyses showed subgroup-specific differential gene expression and pathway activation. Collectively the data presented herein clarify the genomic architecture of the majority of meningiomas, provide previously unappreciated genetic, pathological and clinical correlations, and suggest novel avenues for targeted therapeutics. (Clark et al., 2013, Science, DOI 10. 1126/cience. 1233009; www.sciencemag.org/content/early/2013/01/23/science. 1233009/suppl/DC1; www.sciencemag.org/content/early/2013/01/23/science.1233009/suppl/DC2, incorporated herein by reference in their entireties for all purposes).

The materials and methods employed in these experiments are now described.

Clinical Materials Institutional Review Board approvals for genetic studies, along with written consent from all study subjects, were obtained at the participating institutions. Formal pathology reports along with pre-operative magnetic resonance imaging (MRI) studies were collected from participants.

Selective Tissue Dissection

For each frozen specimen submitted for whole exome sequencing, sections were re-reviewed to confirm the diagnosis and assess the adequacy of the frozen tissue for experimental analysis. On H&E-stained sections from frozen tissue blocks, areas of interest were identified and microscopically dissected to ensure each sample to consist of >70% tumor cells; unwanted regions such as inflammatory and necrotic areas were excluded. Tumors in the replication cohort did not undergo selective tissue dissection. DNA/RNA/protein was then prepared using the Allprep DNA/RNA/protein Mini Kit (Qiagen Science, MD).

Whole-Genome Genotyping

The Illumina Platform was used for whole-genome genotyping and analysis of the samples (n=94). Human OmniExpress-12v 1.0 BeadChips that contain 733,202 markers were used according to the manufacturer's protocol (Illumina, San Diego, Calif., USA). All samples had an overall genotype call rate more than 98%. The copy number alterations (CNA) were detected by comparing the normalized signal intensity between tumor and matched blood or tumor and the average of all blood samples. Segmentation was performed on log intensity (R) ratios using DNACopy algorithm (Olshen et al., 2004, Biostatistics, 5:557). Large scale chromosomal deletion or amplification was defined as affecting more than one-third of the chromosomal arm with accompanying log ratio of signal intensities <−0.1 or >0.1, and B allele frequencies (BAF) at heterozygous sites deviating from 0.5 by at least 0.05 units. Large scale copy neutral LOH was defined similarly, with the exception of log ratio of signal intensities being between −0.1 and 0.1.

Exome Capture and Sequencing

Nimblegen/Roche human solution-capture exome array (Roche Nimblegen, Inc.) was used to capture the exomes of blood and tumor samples according to the manufacturer's protocol with modifications (Bilguvar et al., 2010, Nature, 467:207). Sequencing of the library was performed on Illumina HiSeq instruments using 74 base pairs paired-end reads by multiplexing two tumor samples or three blood samples per lane.

Exome Sequence Analysis

Sequence reads that passed Illumina quality filter were analyzed. Before alignment, low-quality 3'-end of the reads were trimmed and reads with low-complexity sequences and overall low base qualities were filtered (FASTX-Toolkit). PCR primer-contaminated sequence segments (cutadapt version 0.9.5) were trimmed. Sequences for further analysis were kept only if both reads in a pair had more than 35 bases remaining after the above trimming and filtering quality measures. Reads were aligned to the human genome reference sequence (version GRCh37, the same as used in the phase 1 of 1000 Genomes Project) using Stampy (version 1.0.16) (Lunter et al., 2011, Genome Res, 21:936) in a hybrid mode with BWA (version 0.5.9-r16) (Li et al., 2009, Bioinformatics, 25:1754). PCR duplicates were flagged using MarkDuplicates algorithm from Picard (version 1.47) and excluded from further analysis as previously described (DePristo et al., 2011, Nature Genetics 43:491). Metrics describing the alignment quality, such as the fraction of unique read pairs, the fraction of aligned reads and depth of coverage, were collected for each sample by using CollectAlignmentSummaryMetrics and CalculateHsMetrics utilities of Picard. Multi-sequence local realignment was performed around putative and known insertion/deletion sites, where the reads from tumor and matched blood samples were analyzed at the same time. This was followed by the base quality score recalibration using the Genome Analysis Toolkit (GATK, version 1.5-20) (DePristo et al., 2011, Nature genetics, 43:491). Variant sites (point mutations and small indels) for tumor and matched blood pairs were detected using the UnifiedGenotyper algorithm from GATK (DePristo et al., 2011, Nature Genetics 43:491). Variants were concurrently called for unpaired tumor samples using UnifiedGenotyper. In order to identify somatic events, a genotype likelihood-based somatic score proposed by Li was employed (Li, 2011, Bioinformatics, 27:2987). The same phred-scaled score as implemented in bcftools (Li et al., 2009, Bioinformatics, 25:2078) was used. A mutation was considered to be somatic if the matched blood sample was homozygous reference while the tumor sample was heterozygous non-reference and if the somatic score was greater than or equal to 50. Variant sites were filtered by assessing the allelic and overall depth of coverage, the strand, mapping quality and read position biases between reference and non-reference allele supporting reads, the consistency between the number of alleles and that of haplotypes, the root-mean square of mapping quality, the coverage-adjusted variant quality, and the number of mapping-quality-zero reads. For insertions, the maximum score of flanking bases was used and, for deletions, the maximum score of deleted bases was used. Finally, variant alleles were annotated using Ensembl database (version 66) with the help of Variant Effect Predictor (v2.4) tool. From these functional annotations, the most-deleterious consequence was selected for each variant site and the variant allele was considered to be deleterious if its consequence was annotated as stop gained, complex change in transcript, frameshift, splice acceptor/donor sites, stop lost, nonsynonymous codon predicted to be deleterious/damaging, or inframe codon loss/gain. Genes that were mutated in more than one tumor were initially considered and genes were prioritized based on the ratio of deleterious versus non-deleterious mutations observed. The co-occurrence and mutual exclusivity of genes were assessed using one-sided Fisher's exact test (Cui, 2010, PLoS one 5).

Custom Amplicon Sequencing and Analysis

Libraries consisting of the coding exons from TRAF7, NF2, SMO, and the recurrent mutations for $AKT1^{E17K}$ and $KLF4^{K409Q}$ were created using the TargetRich™ custom amplicon kit (Kailos Genetics®). Briefly, genomic regions of interest were targeted by PCR, universal adapters were ligated to the PCR products, and the resulting library was amplified using barcoded primers. Forty-eight samples were pooled and sequenced on a version 2 Illumina MiSeq using paired-end 150 base pair reads. Sequence reads were processed as the whole exome data above but without duplication removal and base quality recalibration. Variants were called for all samples using GATK. The mean coverage of targeted regions is plotted in FIG. 4. All variants were confirmed by Sanger sequencing in tumors and blood where available.

Sanger Sequencing

Coding variants detected by whole exome sequencing or custom amplicon sequencing in the top 5 genes were confirmed by Sanger sequencing using standard protocols (Bilguvar et al., 2010, Nature, 467:207). Amplicons were cycle sequenced on ABI's 9800 Fast Thermocyclers and analyzed as previously described (Bilguvar et al., 2010, Nature, 467:207).

Chromosome 22 Quantification by qPCR

Chromosome 22 loss was assessed by quantitative real-time PCR (Q-PCR) using Fast SYBR® Green Master Mix (Roche Applied Science, Indianapolis, Ind., USA). For each sample, two exons in NF2 gene were used for quantification and normalized against primers on chromosome 11 and 16. Samples and controls were run in triplicate. Dissociation-curves were generated to ensure primer specificity. The squared regression coefficient ($R^2$) for all selected primer pairs was >0.989. The slope of the standard curves was between −3.23 and −3.6. To determine the threshold cycle (Ct), female reference DNA (Promega, Madison, Wis., USA), diluted at 22 ng/uL was used for 4 serial dilutions from 0.25 (¼) fold to 0.00390625 (¹⁄₂₅₆). Each qPCR run included 3 control samples: a commercially available reference female DNA, DNA from a whole genome genotyped meningioma sample with chr22 loss (MN-290), and DNA from a whole genome genotyped meningioma sample with intact chr22 (MN-1). A ratio <0.7 was considered as a loss and a ratio >1.3 was considered as a gain.

Structural Analysis

Mutations were analyzed for potential structural significance using a custom script run in the Swiss-PdbViewer (Guex et al., 1997, Electrophoresis, 18:2714). All figures were created using PyMOL (The PyMOL Molecular Graphics System, Version 1.5.0.1 Schrödinger, LLC). The following were the PDB ID codes: Wild type AKT1: 1UNQ; AKT1 E17K mutation: 2UZS; KLF4: 2WBU.

Immunofluorescence/Immunohistochemistry

Immunohistochemistry on frozen and paraffin sections was performed using standard procedures. SMO (n=4), AKT1/TRAF7 (n=5), KLF4/TRAF7 (n=5), and NF2 loss (n=5) meningioma sections were blindly evaluated by three independent reviewers. For each slide, ten random 20× fields were blindly scored for percentage of positive cells (0-100%), staining density, and the staining strength was calculated by multiplying the percentage of positive cells by the staining density. To determine significance, one-way Anova plus paired t-test was performed using Prism. Antibodies used: KLF4 (Abcam), AKT1 (E17K mutation) (R&D systems), SMO (Abcam), NF2 (Abcam), EMA (Abcam), MHC class II (BioLegend).

H3K27ac ChIP-seq

ChIP-Seq experiments were performed as previously described with minor adjustments (Cotney et al., 2012, Genome Res, 22:1069). Briefly, 10 to 15 frozen sections of each tumor block, dura sample or $5 \times 10^6$ cultured arachnoid cells were collected for ChIP-Seq experiments. Tissue was crosslinked with 1% formaldehyde, quenched with glycine, and washed with PBS. Nuclei were extracted by dounce homogenization and resuspended in nuclear lysis buffer containing 0.3% SDS. Chromatin was sheared by sonication with a Misonix S4000 in a 430A cup horn (60 minutes total, amplitude 30, 10 second pulses, 10 second rest). Soluble chromatin was incubated with magnetic beads coated with H3K27ac antibody (Abcam ab4729) overnight at 4° C. Chromatin was precipitated with magnet, washed extensively, and eluted with TE+1% SDS. Crosslinks were reversed, purified, and subjected to standard Illumina paired-end multiplexed library construction. H3K27ac Chip and input samples were sequenced for each tumor (1×75 bp, HiSeq 2000). Reads were aligned uniquely with bowtie (0.12.7) (Langmead et al., 2009, Genome biology, 10:R25) to the human genome (hg19) and regions of enrichment were identified with MACS (v1.4).

For comparison of meningioma subtype ChIP-seq data, raw reads from ChIP-seq from 7 ENCODE cell-lines (Gm12878, H1hesc, Helas3, Hepg2, Huvec, K562, Nhek) were downloaded from UCSC Genome Browser. H3K27ac ChIP-seq and control data were generated at Broad Institute.

Mutation Significance Analysis

In order to assess the significance of the observed mutations from the exome data, statistical analysis was performed based on the background mutation rate (Ding et al., 2008, Nature, 455:1069). The genome wide background mutation rate for the exome sequenced sample set was estimated to be $2.22 \times 10^6$. Using this genome wide mutation rate, the significance of the observed mutations in each gene was tested by comparing them to the number of expected mutations based on the length of the target sequence.

Microarray Data Analysis

Illumina HumanHT12.v4 gene expression microarray chips were used. Merging of the data, background removal and normalization processes were performed using the limma R package. Samples with RNA Integrity Numbers (RINs) less than 3 or a low signal to noise ratio were excluded. Principal Component Analysis (PCA) analysis was then performed to detect the presence of any batch effect which was corrected using the COMBAT package (Jeffrey T. Leek, 3.0.3, sva: Surrogate Variable Analysis). The normalized, batch effect corrected data for 22 samples that survived these quality control steps were used to perform an unsupervised hierarchical clustering using the euclidean distance as the dissimilarity metric and the average agglomerative method for clustering. Differential gene expression analysis was then performed using the log-odds of differential expression value as implemented in the ebayes method of the limma package.

Pathway Analysis

Meningioma subtype specific genes were selected to build the gene interaction network using Cytoscape plugin ReactomeFI (Croft et al., 2011, Nucleic acids research, 39:D691). Gene expression fold change from microarray and promoter marking status from H3K27ac ChIP-seq were depicted in the network. Gene interaction and pathway annotation of the network were aided by the manually curated pathway annotations provided by Reactome.

PARADIGM Algorithm

Figure 14:
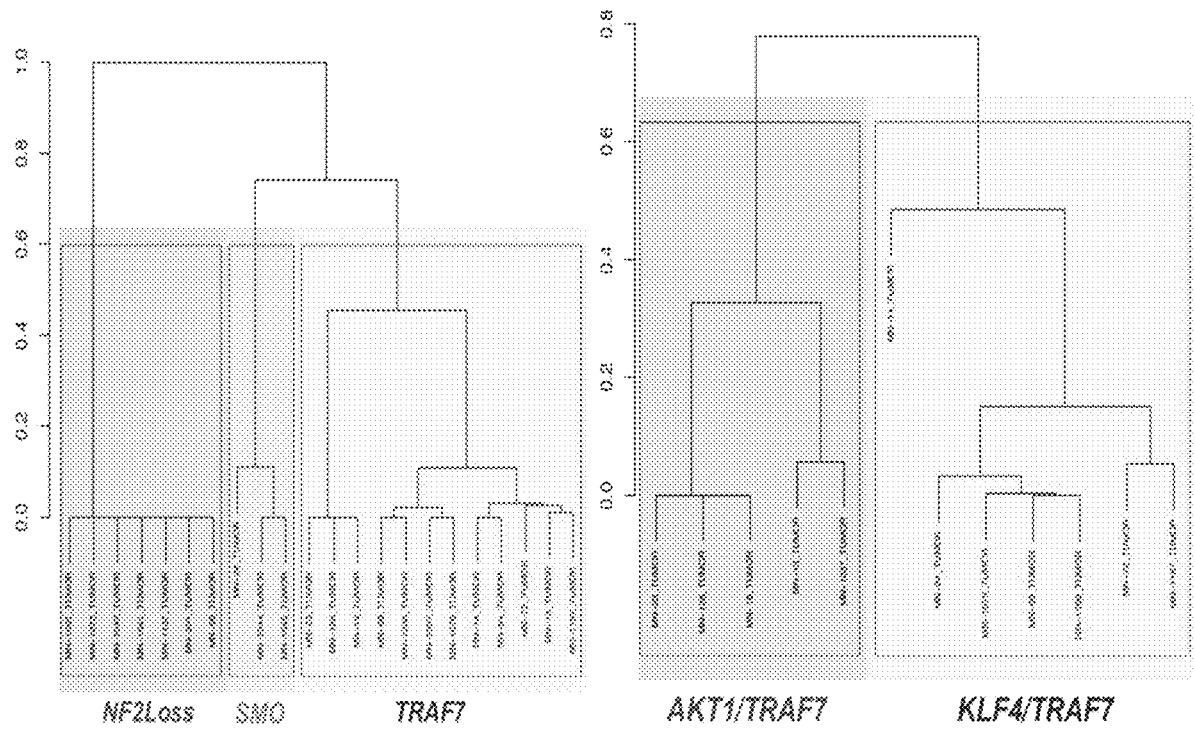
FIG. 14 is a set of images depicting the results of experiments. The left panel depicts that sample clustering based on inferred pathway activities separate NF2/loss meningiomas from non-NF2 mutant tumors. The right panel demonstrates that within the TRAF7 mutant group, AKT1 and KLF4 mutations form distinct clusters.

Gene expression and copy number data were integrated to produce inferred pathway activity (IPA) levels as previously described (Vaske et al., 2010, Bioinformatics, 26:i237). The method produced a matrix of IPAs with 18577 entities (representing proteins, complexes, and processes) in the rows and 22 samples in the columns. The pathway entities that had zero activities in all of the samples were removed, yielding 17976 entities. For sample sub-classification, the consensus clustering was run using the mean-centered IPAs with 80% subsampling over 1000 iterations of hierarchical clustering based on a Pearson correlation distance metric and average linking (Monti et al., 2003, Machine learning, 52:91). The consensus clustering identified 3 robust subgroups, corresponding to TRAF7, SMO and NF2 mutations (FIG. 14). TRAF7 subgroup was further clustered into 2 sub-clusters corresponding to AKT1/TRAF7 and KLF4/TRAF7 mutated samples (FIG. 14).

Subgroup Specific Differentially Activated Pathways

The differential activity of each pathway within a specific meningioma subgroup was evaluated using the Global Test (Goeman et al., 2004, Bioinformatics, 20:93). Pathway entities with highly correlated IPAs (>0.9 correlation coefficient) were merged into single entities. The contribution of an entity in a pathway was evaluated and entities with weight >0.5 and p-value <0.001 were considered significant contributors to a pathway. The heatmap for the significant pathways (corrected P value of the Global Test <0.05) was then plotted.

The results of the experiments are now described.

In order to comprehensively characterize the genomics of meningioma and to gain further insight into molecular mechanisms of tumor formation, 50 previously non-irradiated grade I (n=39) and grade II (n=11) meningiomas were initially whole-genome genotyped and exome sequenced. For 39 of these tumors (n=33, grade I and n=6, grade II) DNA from matched blood samples was available. Exome sequencing of tumor and blood samples achieved a mean per-targeted base coverage of 255-fold and 154-fold with an average of 93.5% and 91.7% of all targeted bases being read at least 20 times, respectively. For the meningiomas in which matching blood samples were available, the mean number protein-altering somatic mutations was 7.2 (range 1-15), a considerably smaller number compared to malignant tumors.

To find potential driver mutations, the exome wide background mutation rate was estimated and the significance of observing the number of mutations in the data set was calculated for each transcript, correcting for coding sequence length (Ding et al., 2008, Nature, 455:1069) (FIG. 1C). The top genes included the known neoplasia-associated genes, neurofibromin (NF2), v-akt murine thymoma viral oncogene homolog 1 (AKT1) and Smoothened, frizzled family receptor (SMO), as well as two novel ones, TNF receptor-associated factor 7 (TRAF7) and Krupple-like factor 4 (KLF4). While NF2, TRAF7 and SMO mutations were mutually exclusive and potentially defined distinct meningioma subtypes, the recurrent AKT1 and KLF4 mutations commonly co-existed with TRAF7 variants (FIG. 15). Collectively, coding mutations in these 5 genes combined with chromosome 22 loss (n=30), which often co-occurred with NF2 mutations (n=22), accounted for nearly 90% of meningiomas analyzed (FIG. 15). Among these, somatic driver mutations in TRAF7 or KLF4 have not previously been associated with any neoplasia.

Further examination of the exome sequencing results focusing on genes reported to play a role in neoplasia revealed mutations in a small number of genes not previously associated with meningiomas. These included single mutations in CREBBP, PIK3CA (R108H variant), PIK3R1 (deletion p. 306-307) and BRCA1 genes in a total of 4 meningiomas. In addition 2 SMARCB1 mutations were observed, which co-existed with NF2 loss and have previously have been reported in meningiomas (Schmitz et al., 2001, Br J Cancer, 84:199).

Figure 4:
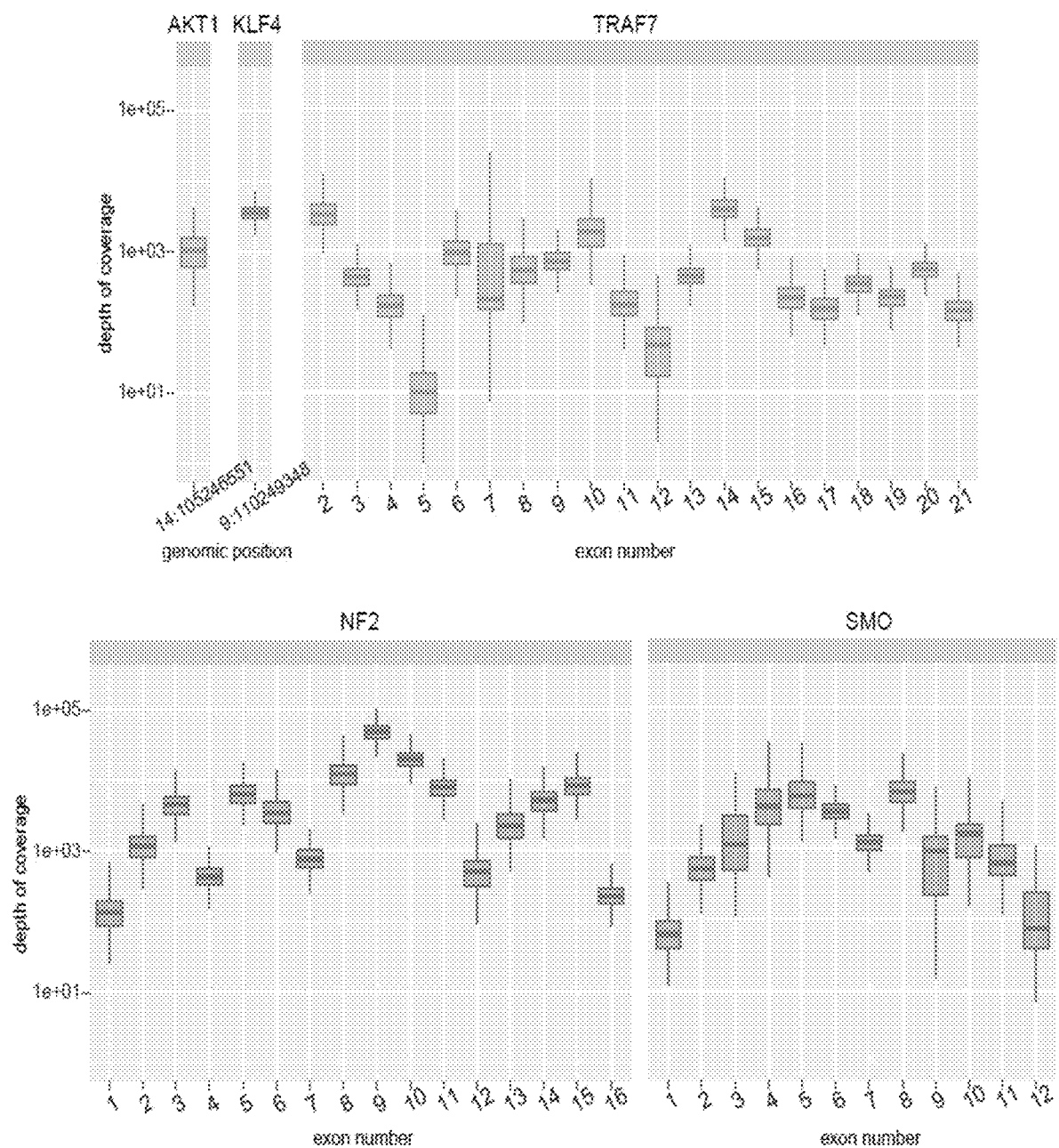
FIG. 4 is a set of graphs depicting the results of experiments demonstrating the mean coverage per targeted genomic region, meningioma replication cohort. Coding exons for TRAF7, NF2, and SMO, and the recurrent mutations $AKT1^{E17K}$ and $KLF4^{K409Q}$ were targeted using the TargetRich™ custom amplicon kit (Kailos Genetics®) and sequenced on a version 2 Illumina MiSeq using paired-end 150 basepair reads.

Based on these results, next-generation technology was used to re-sequence an independent set of 250 unradiated meningiomas (204 grade 1 and 46 high grade meningiomas) targeting all coding exons of NF2, TRAF7 and SMO as well as the $KLF4^{K409Q}$ and $AKT1^{E17K}$ recurrent mutations. The depth of coverage for all targeted exons is shown in FIG. 4. Chromosome 22 integrity was also assessed in all samples.

In the combined analysis of 300 meningiomas (50 with exome sequencing and 250 with targeted sequencing), coding mutations were identified in 237 (79%) involving these five genes and/or evidence for chromosome 22 loss (FIG. 1D). NF2 mutations were present in 108 (36%). These included 107 premature termination, frameshift or splice site mutations and 1 missense mutation.

Figures 1E, 1F, 1G, 1H:
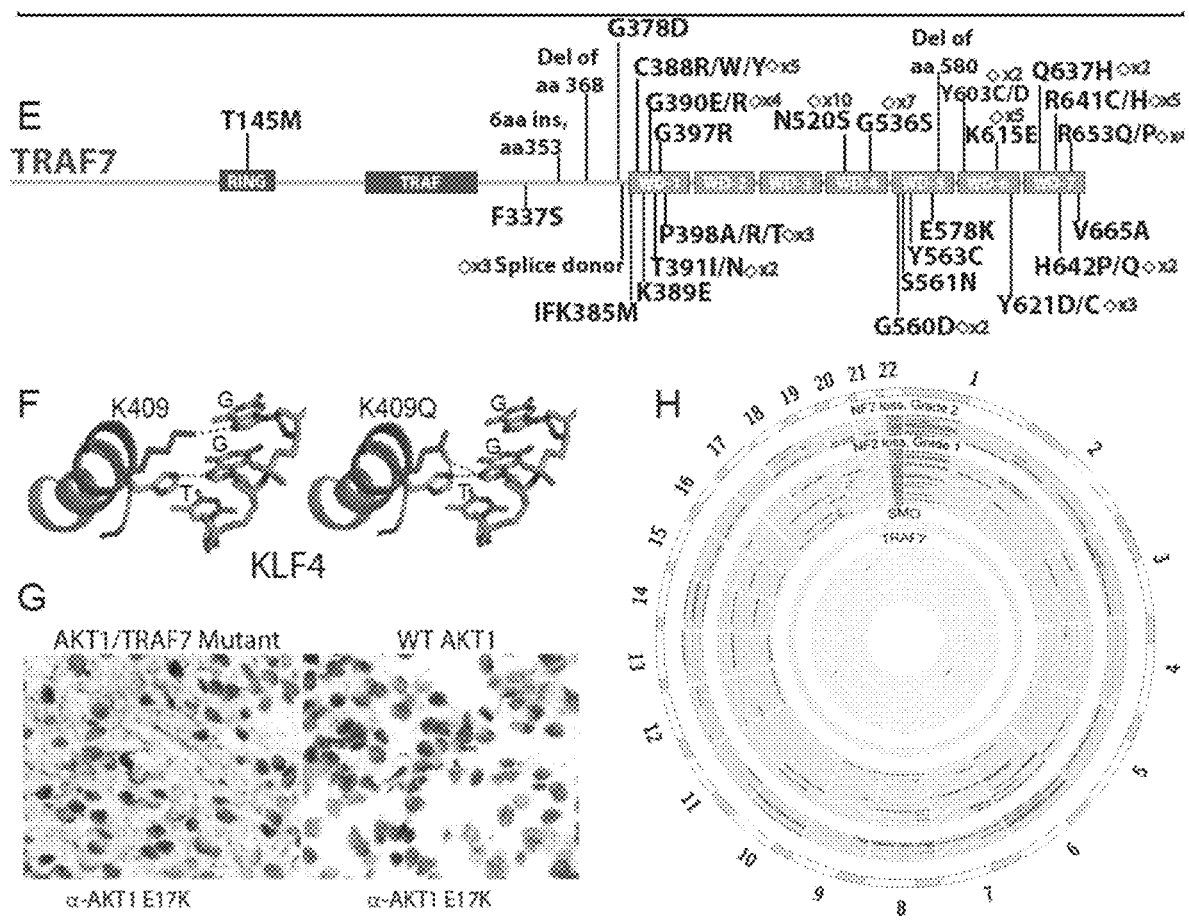

Collectively, pathogenic mutations in the novel neoplasia genes TRAF7 and KLF4 were identified in nearly one-fourth of the 300 meningiomas examined. Coding mutations in TRAF7 were found in 72 meningiomas, which were confirmed to be of somatic origin in all samples in which both blood and tumor DNA samples were available (n=42). TRAF7 mutations were always exclusive of NF2 mutations, a result highly unlikely to occur by chance (mutual exclusivity P value ($P_{me}$)=2.55×10$^{-1}$ (Cui, 2010, PLoS one, 5)). TRAF7 is a pro-apoptotic N-terminal RING and zinc finger domain protein with E3 ubiquitin ligase activity that contains seven WD40 repeats in its C terminus (Xu et al., 2004, J Biol Chem, 279:17278). TRAF7 interacts with several molecules, such as MEKK3, through these WD40 repeats, affecting several signaling pathways, including NF-κB, and modulate ubiquitination of various molecules such as c-FLIP, an anti-apoptotic molecule (Bouwmeester et al., 2004, Nat Cell Biol, 6:97). It is consequently of interest that 67 of the 72 TRAF7 mutations, including 15 recurrent mutations, all map to the WD40 repeat domains (FIG. 1E).

Figure 5:
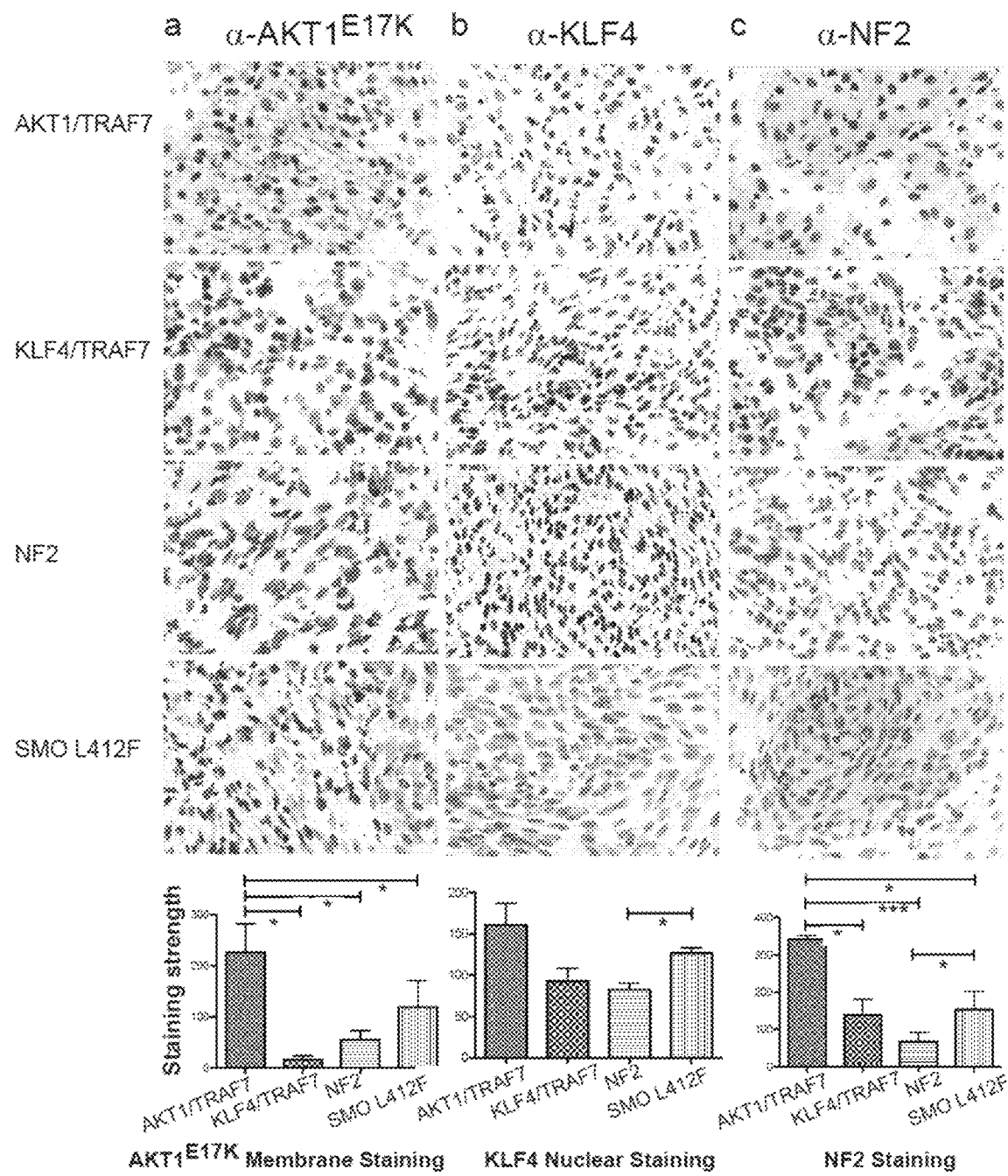
FIG. 5, comprising
Figure 6:
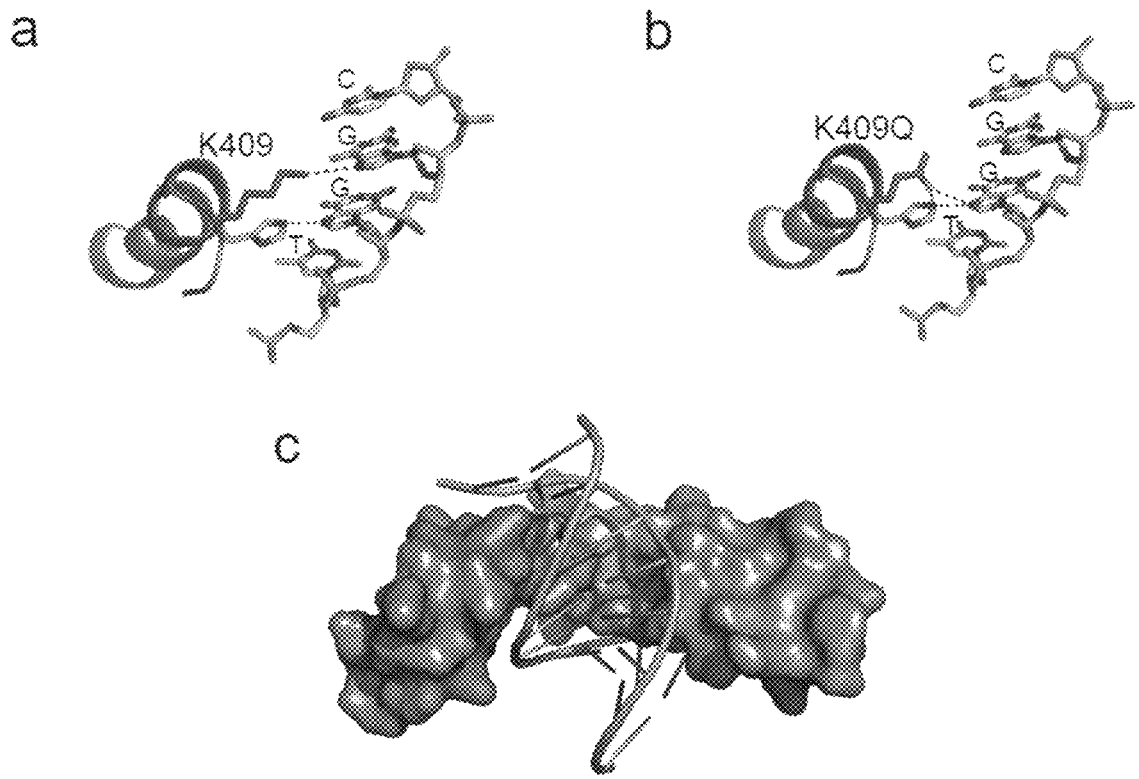
FIG. 6, comprising

In the transcription factor KLF4, a previously unreported K409Q mutation was identified in 31 meningiomas (17 from matched blood/tumor pairs). Interestingly, all but one of these mutations was found in TRAF7 mutant meningiomas (co-occurrence P value ($P_{co}$)=2.50×10$^{-20}$) and all mutations were exclusive of NF2 mutations ($P_{me}$=3.77×10$^{-7}$). KLF4 is shown to be expressed in meningiomas (FIG. 5). KLF4 has been shown to regulate differentiation of several cell types and is best known as one of four genes, which encode proteins that together promote reprogramming of differentiated somatic cells into pluripotent stem cells (Takahashi et al., 2007, Cell, 131:861). Deletion of the KLF4 DNA-binding domain blocks differentiation and induces self-renewal in hematopoietic cells (Schuetz et al., 2011, Cell Mol Life Sci, 68:3121). The recurrently mutated KLF4 residue, K409, lies within the first zinc finger and makes direct DNA contact in the major groove of the DNA binding motif (Schuetz et al., 2011, Cell Mol Life Sci, 68:3121) (FIG. 1F and FIG. 6).

Figure 7:
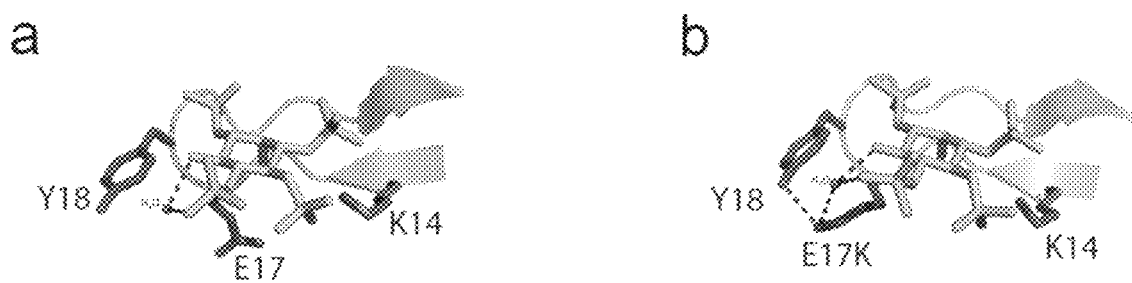
FIG. 7, comprising
Figure 8:
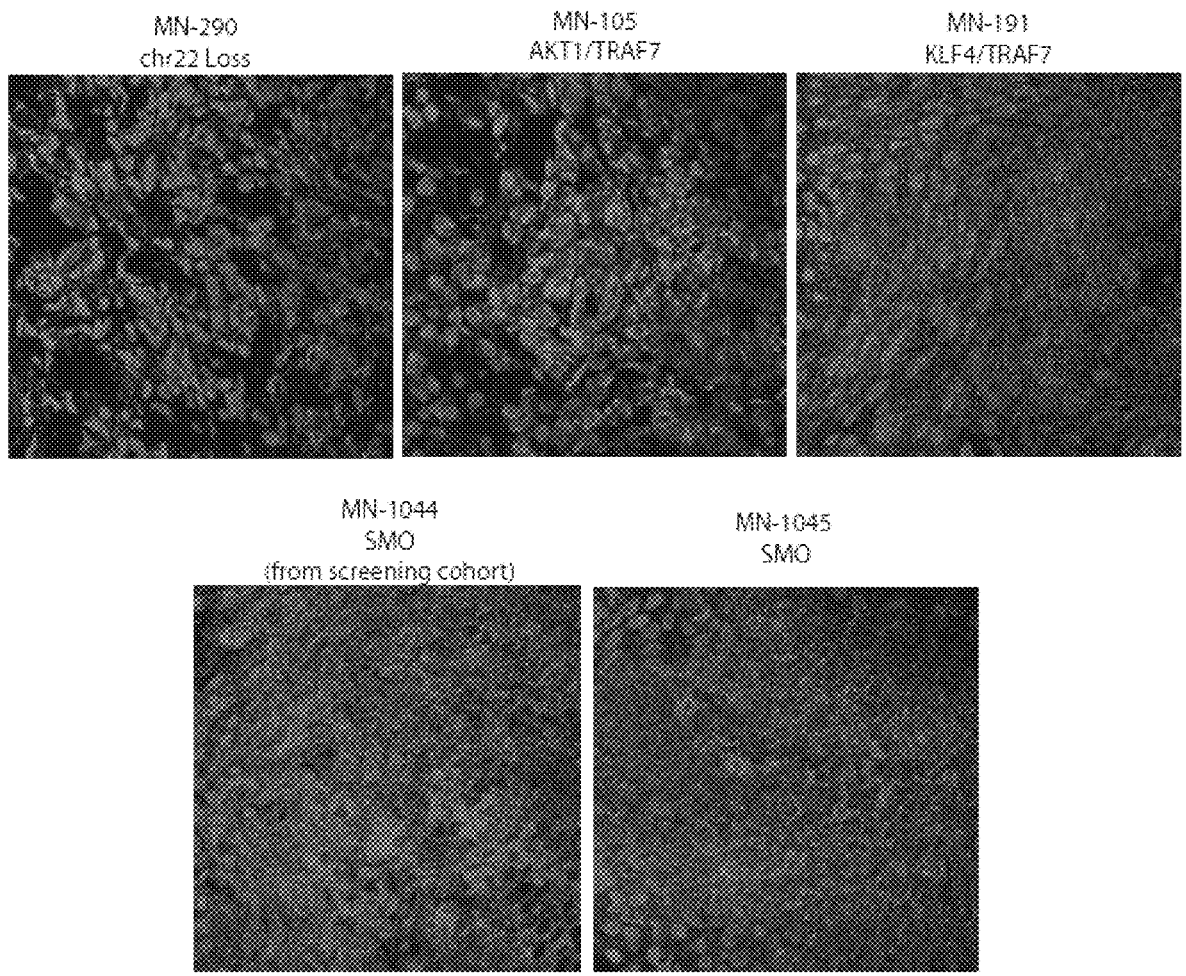
FIG. 8 is a set of images depicting the results of experiments demonstrating that Smoothened (SMO) protein is expressed in meningiomas. Tumors of different mutations were stained for Smoothened and images acquired using identical confocal microscope settings.

As noted, in addition to identifying novel loci, mutations were found in genes known to be involved in neoplasia, but not previously associated with meningiomas. Thirty-eight tumors (25 from matched tumors) carried the known neoplasia-related recurrent mutation, AKT$^{E17K}$, which was readily detectable by immunohistochemistry using an antibody specific for this mutation (FIG. 1G). The AKT1$^{E17K}$ mutation was mutually exclusive of NF2 mutations except in one case ($P_{me}$=2.70×10$^7$). Although the AKT1$^{E17K}$ mutation co-occurred with TRAF7 mutations in 25 of the 38 tumors ($P_{co}$=3.90×10$^{-9}$), it was always exclusive of the KLF4$^{K409Q}$, mutation ($P_{me}$=1.18×10$^{-2}$). The AKT1$^{E17K}$ mutation activates the PI3K/AKT signaling (Carpten et al., 2007, Nature, 448:439) and has been implicated in the formation of a number of tumors and hyperproliferative states, but not in meningioma (FIG. 7). Similarly, in 11 tumors, neoplasia associated mutations were identified in SMO, which was found to be expressed in meningiomas (FIG. 8). These mutations include a recurrent L412F variant in 7 meningiomas and a previously reported W535L mutation, which has been shown to result in activation of Hedgehog signaling in basal cell carcinoma (Xie et al., 1998, Nature, 391:90). Eight of these SMO mutations were mutually exclusive of other driver mutations ($P_{me}$=1.24×10$^{-2}$).

Figure 9:
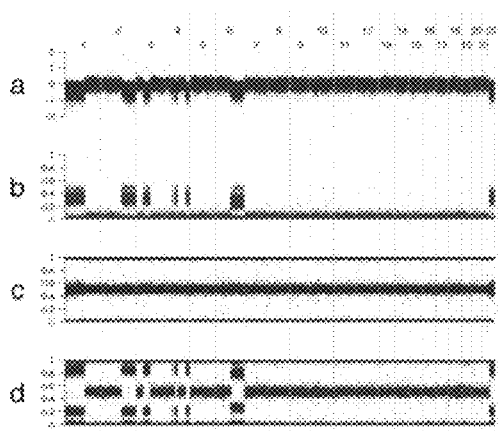
FIG. 9, comprising
Figure 9:
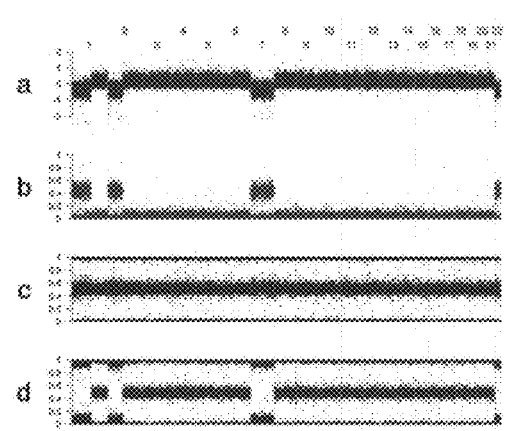
Figure 9:
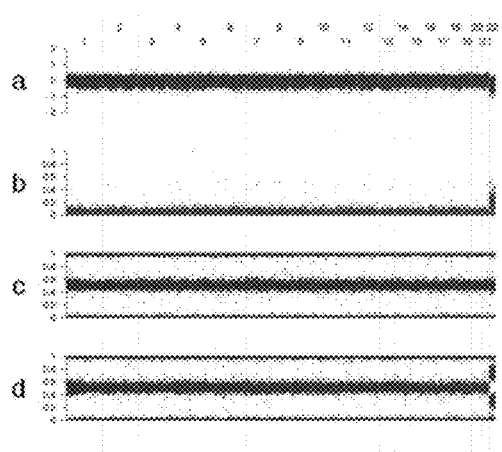
Figure 9:
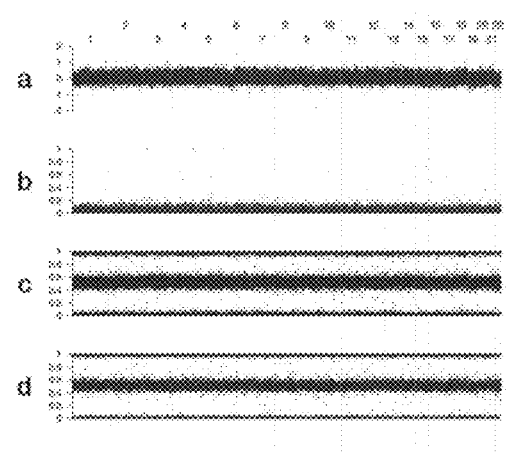
Figure 9:
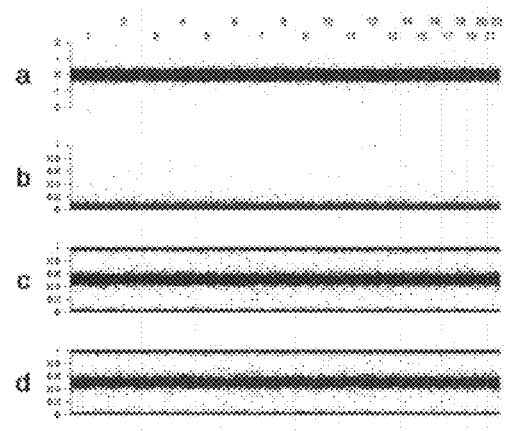
Figure 10A:
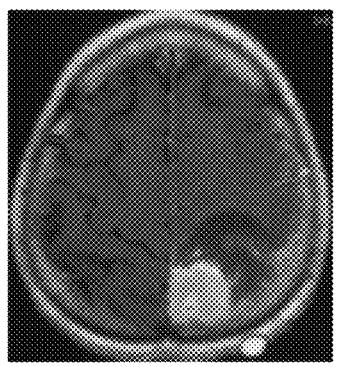
Figure 10A:
Figure 10A:
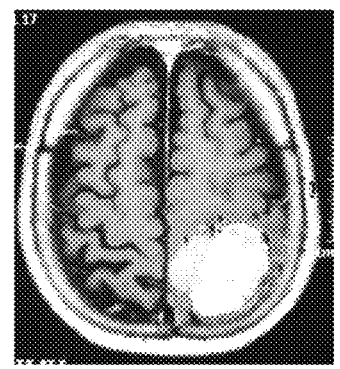
Figure 10A:
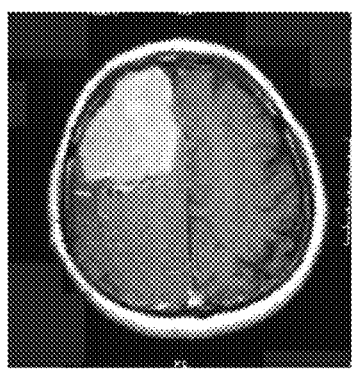
Figure 10A:
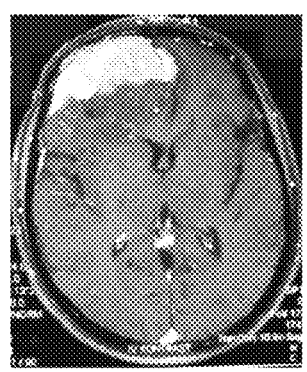
Figure 10A:
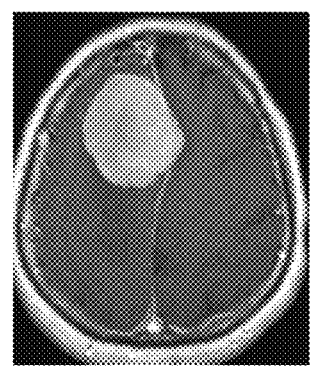
Figure 10A:
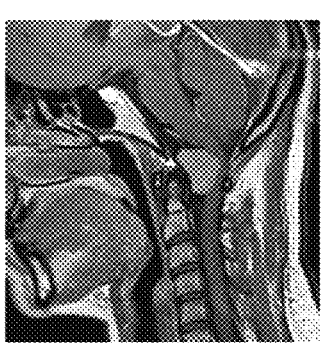
Figure 10A:
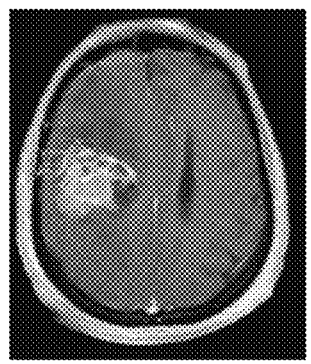
Figure 10B:
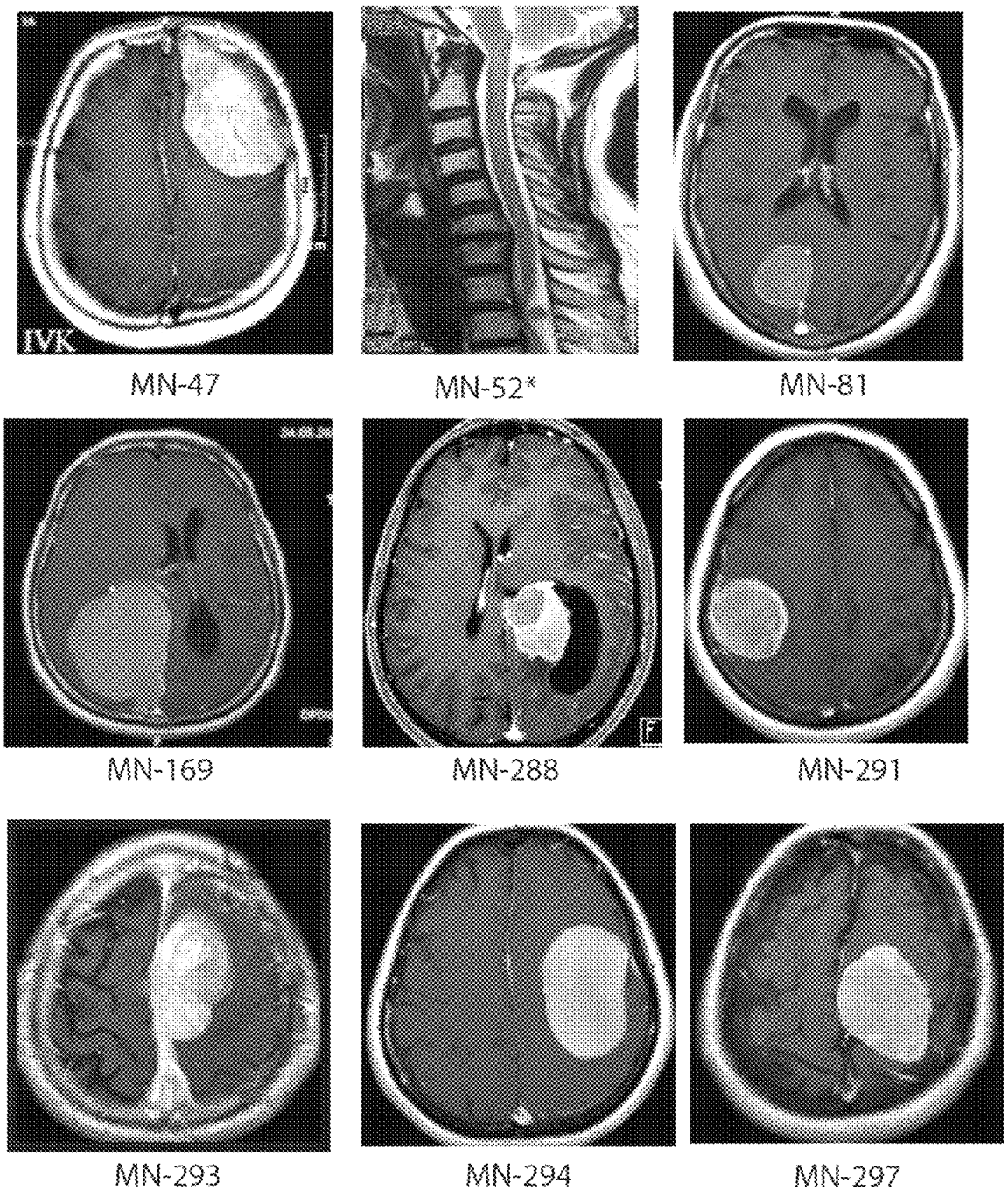
Figure 10F:
Figure 10F:
Figure 10F:
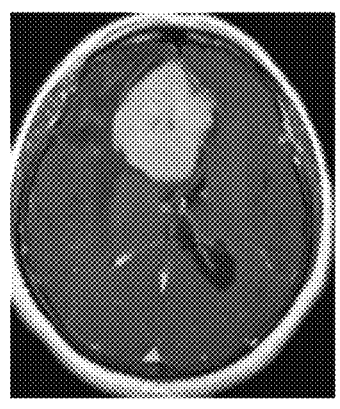
Figure 10F:
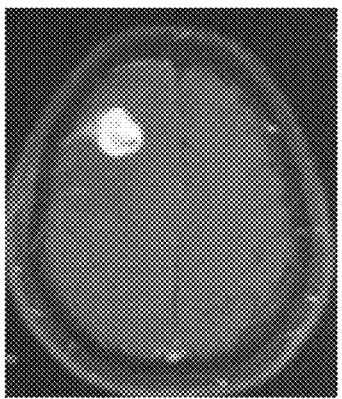
Figure 10F:
Figure 10F:
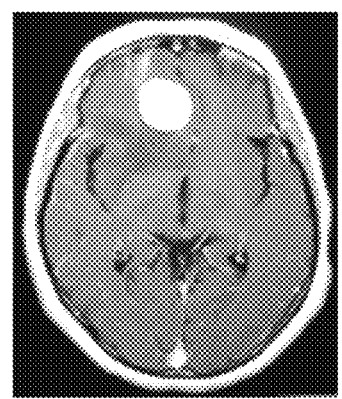
Figure 10F:
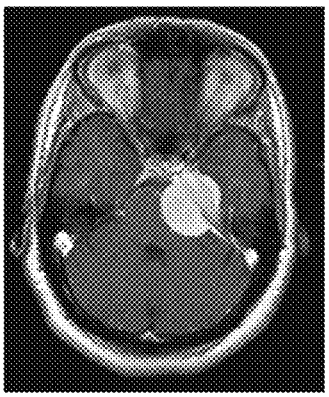
Figure 10F:
Figure 10F:
Figure 10H:
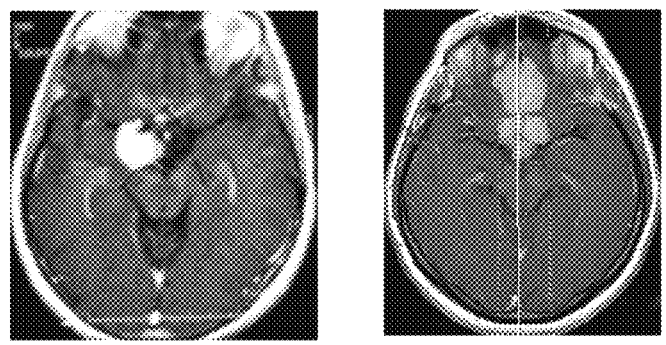

Next, evidence of chromosomal instability associated with these coding mutations was investigated. Chromosome 22 loss was detected in 149 tumors, including all 108 with a coding NF2 mutation ($P_{co}$=1.32×10$^{-47}$). Conversely, chromosomal loss was rarely observed in TRAF7, AKT1, KLF4 or SMO mutant tumors (n=8) ($P_{me}$=5.22×10$^{-25}$) (FIG. 1H). Importantly, there was also a significant difference among high grade versus benign tumors with regard to chromosome 22 loss (P=5.90×10$^{-5}$, Odds Ratio (OR)=3.54). Moreover, chromosome 22 loss in atypical and malignant meningiomas was associated with additional chromosomal instability, evidenced by a greater average number of large scale chromosomal events per tumor versus benign meningiomas (FIG. 1H and FIG. 9) (6.9 vs. 1.7 events/tumor). High-grade tumors were also associated with an increased rate of NF2 mutations (P=0.03, OR=1.96) and were observed more frequently in males versus females (P=6.45×10$^{-4}$, OR=2.93).

Figures 2A, 2B, 2C, 2D, 2E, 2F, 2G, 2H, 2I:
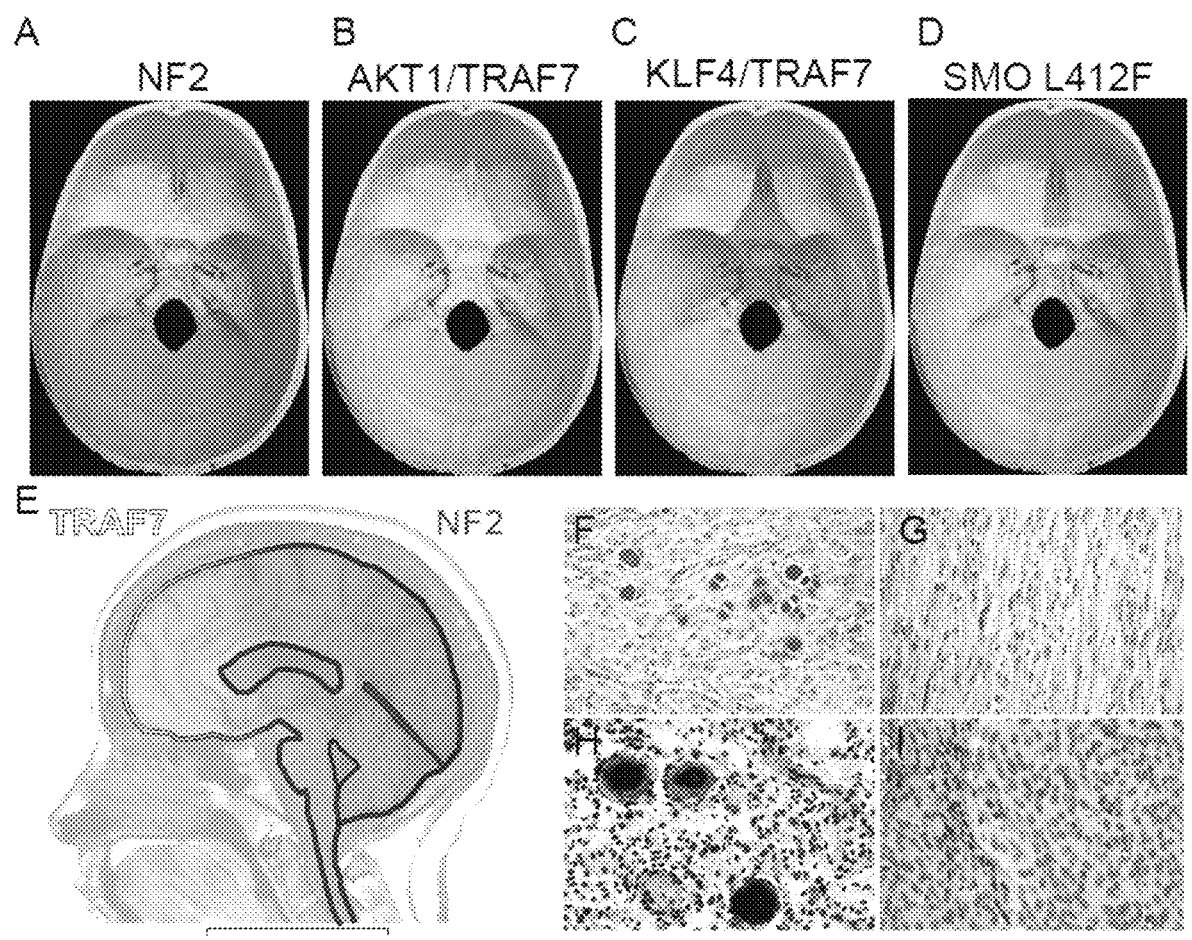
FIG. 2A through FIG. 2K, are a set of images depicting the results of experiments demonstrating that the anatomical localization, histological subtype, patterns of gene expression and H3K27 promoter acetylation define distinct meningioma subtypes.

Given these observations pointing to distinct tumor subtypes based on driver mutations, it was tested whether the anatomical distribution and histological profiles of meningiomas also correlated with their mutational profiles. During fetal development, meninges, under the strong influence of the developing brain and skull bones, differentiate either from the neural crest or the mesoderm. Although in humans the exact contributions of these embryonic structures to meningeal formation in various brain regions are not well studied, the general developmental patterns are well-established in other species. Considering these embryonic patterns and consistent with established clinical classifications, cerebral meningiomas were initially grouped into those originating along the skull base or those present at the cerebral hemispheres (FIG. 2A to FIG. 2E, and FIG. 10). A significant difference was observed between these two groups. Overall, tumors with NF2 mutations and/or chromosome 22 loss (referred to as NF2/loss from hereafter) were far more likely to localize to the hemispheres relative to the skull base (P=9.22×10$^{-14}$, OR=6.74). Along non-skull base regions, the frequency of NF2/loss meningiomas followed an anteroposterior gradient such that nearly all posterior cerebral (parieto-occipital) or cerebellar meningiomas were NF2/loss tumors (FIG. 2E). Similarly, all spinal meningiomas were also NF2/loss subtype.

In contrast, along the medial skull base regions, especially near the midline, virtually all meningiomas were either TRAF7/AKT1/KLF4 or SMO mutant (referred as to non-NF2 mutant hereafter) (P=4.36×10$^{-8}$, OR=8.80) with NF2/loss meningiomas being observed only along the lateral skull base regions (P=1.55×10$^{-12}$, OR=23.11) (FIG. 2A). With regards to the TRAF7 co-mutated AKT1 and KLF4 tumors, whereas AKT1 mutants were mainly restricted to the middle skull base regions (FIG. 2B), some of the KLF4 mutant meningiomas extended laterally (FIG. 2C). Meningiomas with only the recurrent SMO L412F mutation (n=5) all localized to the medial anterior skull base (FIG. 2D). This is particularly interesting considering the role of Hedgehog signaling in midline patterning and forebrain development as loss of function mutations in this gene lead to holoprosencephaly, the midline failure of embryonic forebrain to divide into two hemispheres.

Not surprisingly, mutational profiles also showed a correlation with histological diagnoses. The strongest association was found with the 'secretory' meningioma subtype, which follow a more aggressive clinical course due to increased brain swelling. All 12 of these meningiomas in the series carried both TRAF7 and KLF4 mutations ($P_{co}$=6.02×$10^{-12}$) (FIG. 2F). In addition, of the common histological subtypes, ~80% of both fibrous (FIG. 2G) and psammomatous (FIG. 2H) meningiomas had NF2/loss ($P_{co}$=1.28×$10^{-3}$ and 6.84×$10^{-3}$, respectively), which was seen in only 23% of pure meningotheliomatous tumors (FIG. 2I) ($P_{me}$=5.01×$10^{-5}$); 48.5% of the latter subtype harbored non-NF2 mutations ($P_{co}$=1.46×$10^{-2}$).

Figures 2J, 2K:
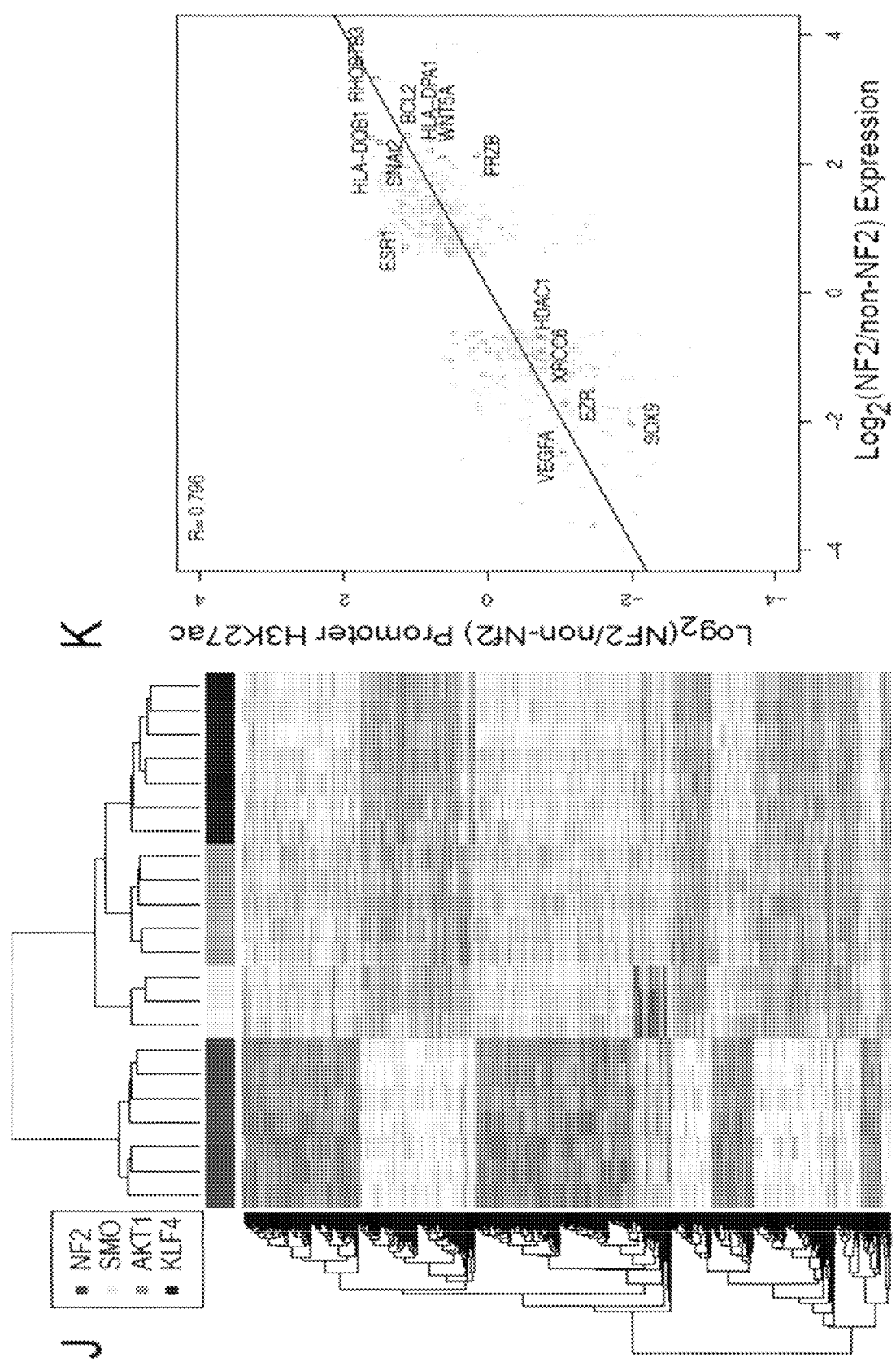
Figures 3A, 3B, 3C:
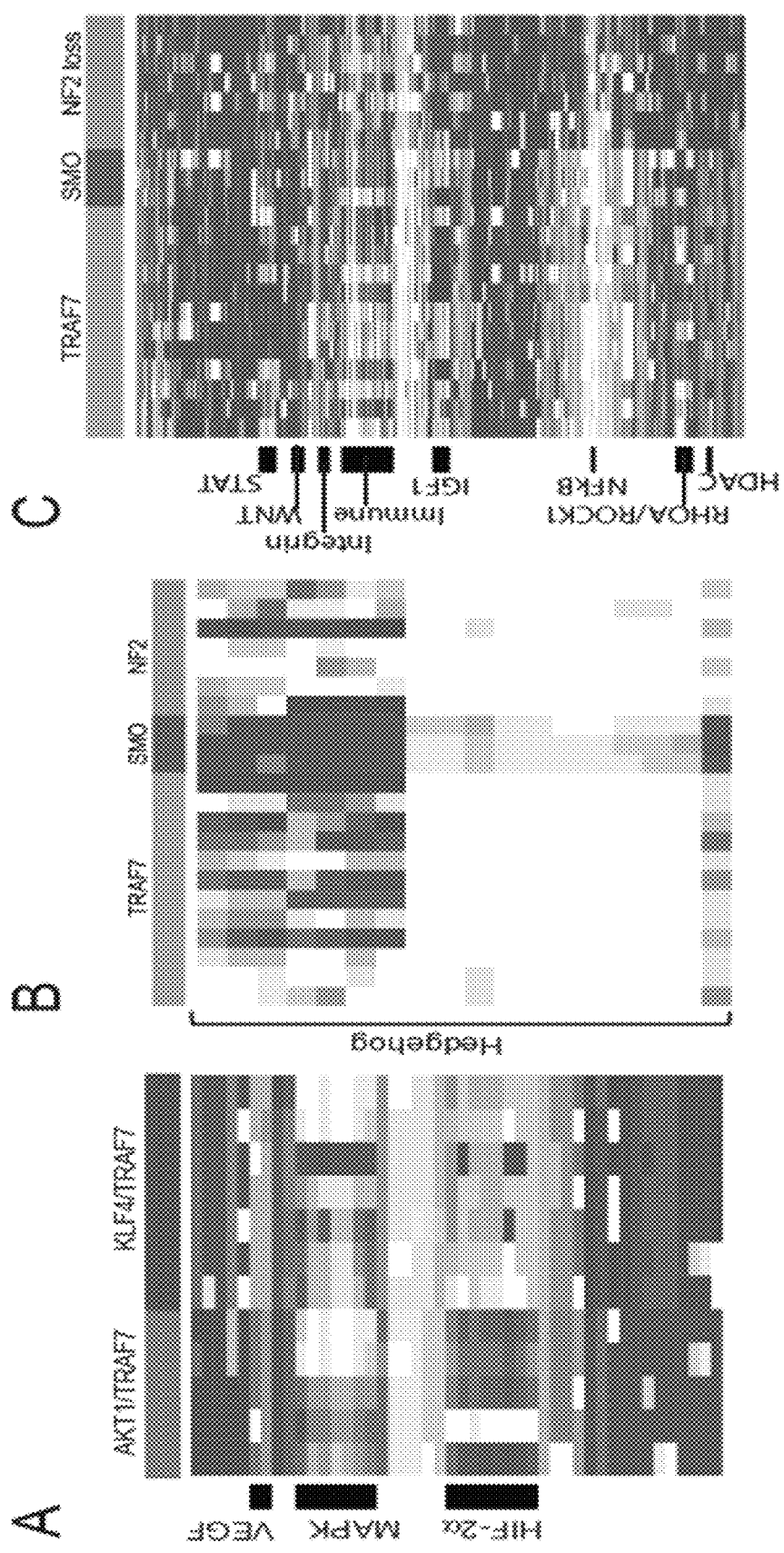
FIG. 3A through FIG. 3G, is a set of images depicting the results of experiments demonstrating that differential gene expression and inferred signaling pathways activities reveal differences among meningioma subtypes.
Figures 3D, 3E, 3F, 3G:
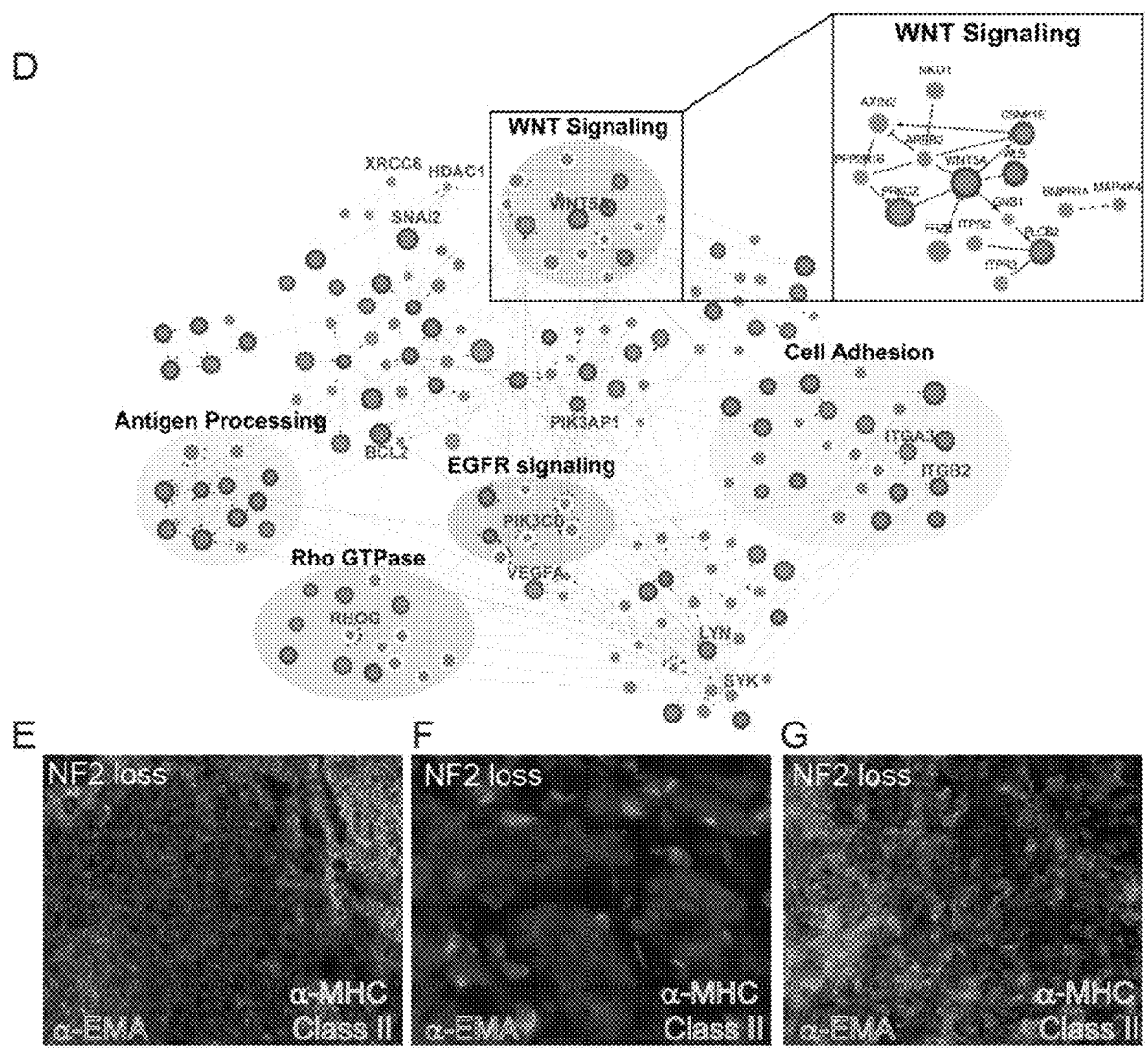
Figure 11:
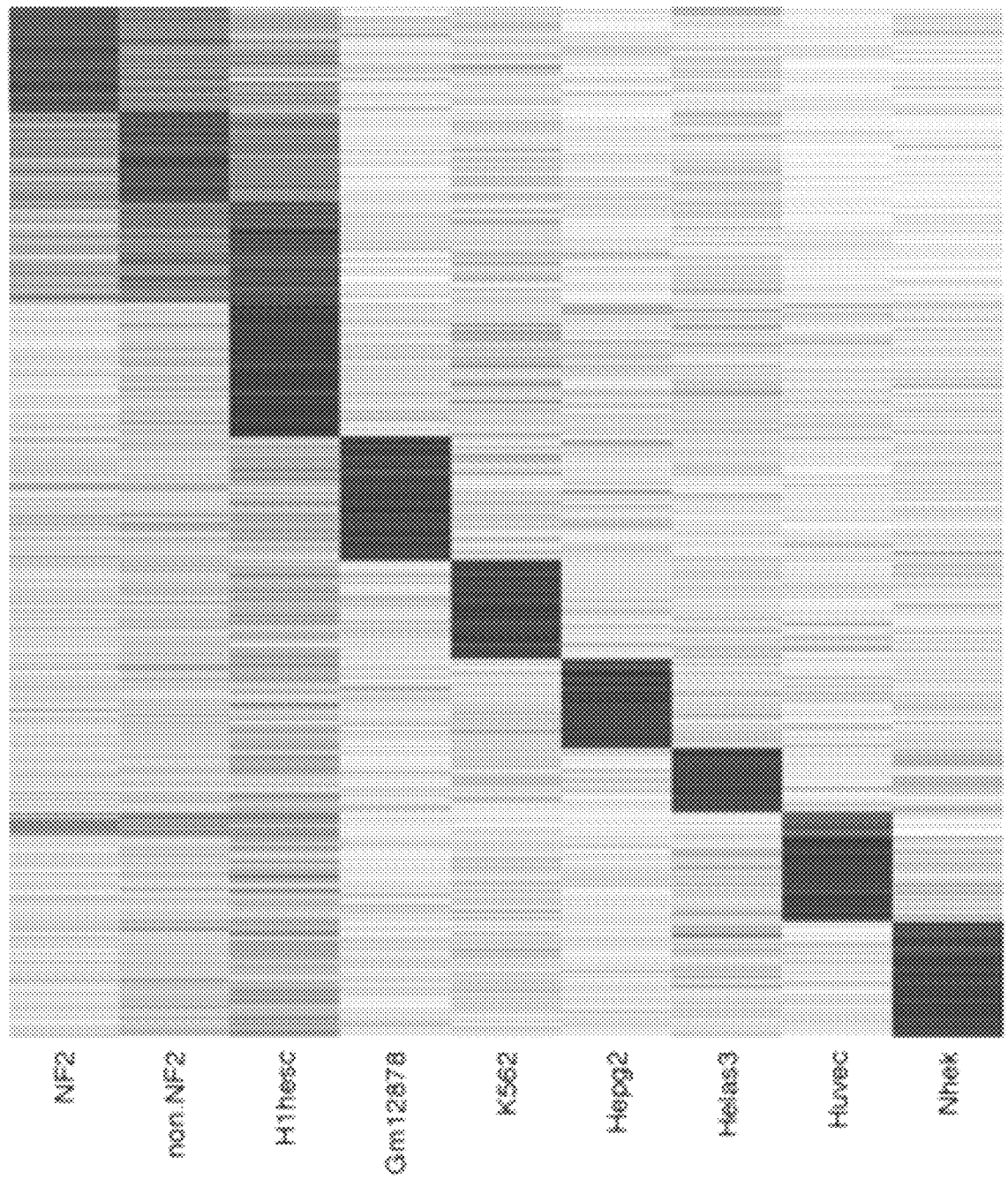
FIG. 11 is an image depicting the results of experiments demonstrating the K means clustering of H3K27ac marked enhancers comparing meningioma subtypes to 7 ENCODE cell-lines (Gm12878, H1hesc, Helas3, Hepg2, Huvec, K562, Nhek). This analysis reveals that although meningioma subtypes cluster closely as compared to other cell lines, NF2 and non-NF2 mutant tumors reveal distinct enhancer acetylation patterns.
Figure 12:
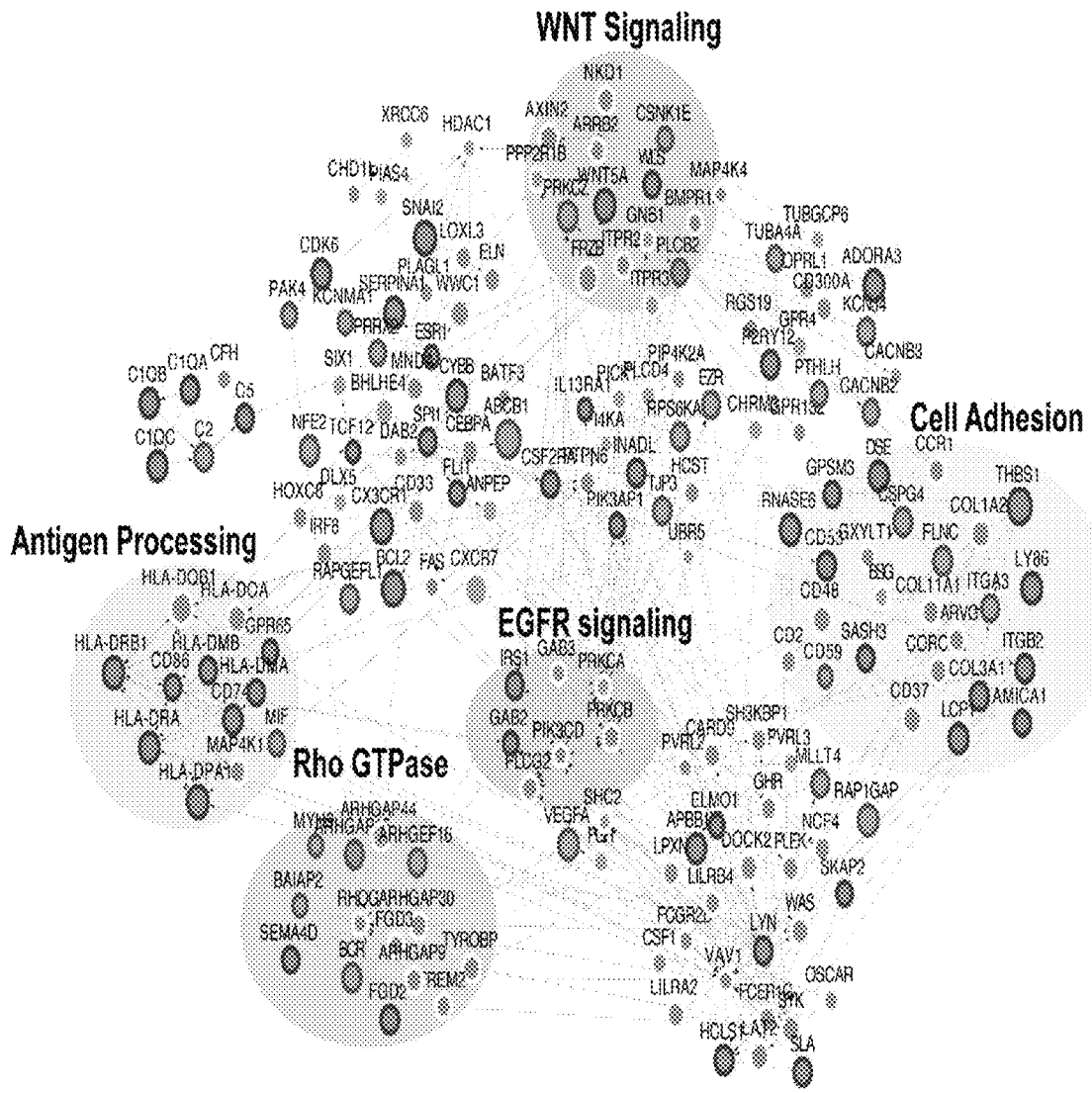
FIG. 12 is an image depicting the results of a Detailed Reactome Analysis of NF2 loss specific genes. NF2 loss specific genes were plotted using cytoscape plugin ReactomeFI. Nodes represent genes that are up or down-regulated in NF2/loss subtype versus non-NF2 meningiomas. Borders represent differential H3K27 acetylation levels.
Figure 13:
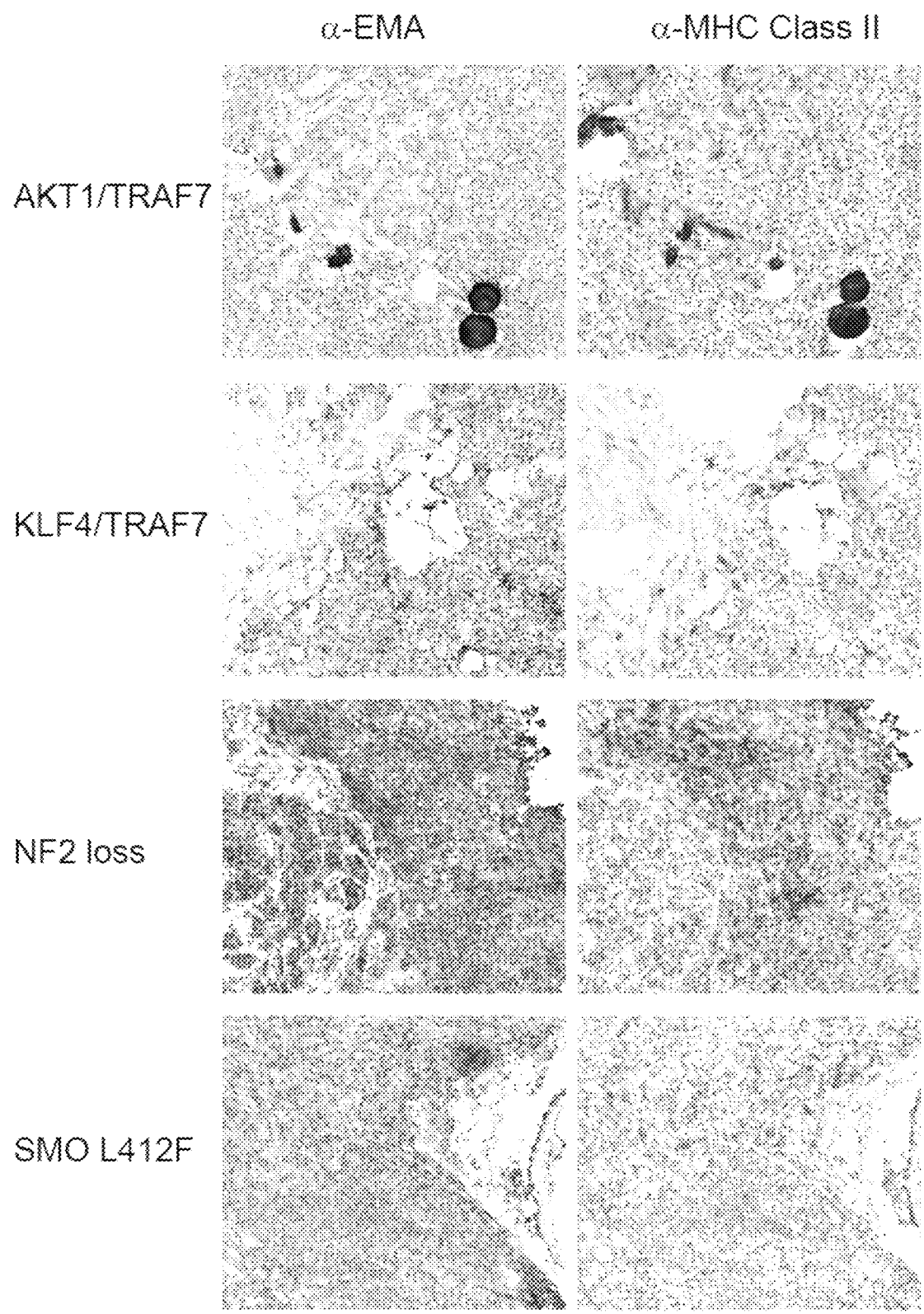
FIG. 13 is a set of images depicting the results of experiments. The images are representative EMA and MHC Class II stainings for meningioma subtypes. Epithelial membrane antigen (EMA) expression marked the meningioma cells. There was increased MHC Class II positive cells in NF2/loss tumors.

These results clearly identify meningioma subgroups, distinguishing them based on their mutational profile, potential for chromosomal instability, malignant transformation, anatomical location and histological subtype. Consistent with this observation, unsupervised hierarchical clustering of meningiomas based on gene expression or chromatin immunoprecipitation-sequencing (H3K27 acetylation ChIP-seq) analyses confirmed clustering of meningiomas into NF2/loss versus non-NF2 mutant groups (FIG. 2J and FIG. 11) and revealed several molecules whose acetylation and expression was specific to a subtype. For these differentially expressed genes, there was a strong correlation between expression and ChIP-seq data (FIG. 2K). Among the non-NF2 meningiomas (FIG. 3A and FIG. 3B), SMO mutants were clearly defined by increased expression and activation of the Hedgehog pathway (FDR=6.67×$10^{-4}$), suggesting that inhibition of this pathway might prove to be therapeutic for this subgroup. Within the NF2/loss group, several oncogenic pathways (Wnt, integrin, receptor tyrosine kinase signaling) and effector molecules (such as SNAI2 transcription factor) that induce epithelial-mesenchymal transition were found to be activated (FIG. 3C, FIG. 3D, and FIG. 12). Interestingly, up-regulation and increased acetylation of immune cell markers (including class II MHC molecules) was observed in NF2/loss tumors (FIG. 3C and FIG. 3D). In these meningiomas, immunohistochemical analyses revealed the MHC+ cells to form distinct clusters (FIG. 3E to FIG. 3G and FIG. 13). While not wishing to be bound by any particular theory, this suggests that they might represent infiltrating immune cells.

By using an integrative genomics approach, the molecular basis of the majority of non-NF2 mutant meningiomas was able to be determined. As described herein, this approach identified previously unrecognized subtypes characterized by TRAF7, AKT1, KLF4 or SMO mutations. Based on the mutually exclusive distribution of mutations, distinct potential for atypical transformation, anatomical location, histological appearance as well as differential gene expression and acetylation patterns, these molecular subtypes represent diverse biological classes with important clinical implications. The results presented herein show that the mutational profile of a meningioma can largely be predicted based on its anatomical position, and possibly embryonic origin. Moreover, while not wishing to be bound by any particular theory, depending on the molecular make-up of an individual tumor, use of therapeutics that inhibit a specific pathway could be effective in the management of meningiomas. For example, small-molecule inhibitors of SMO (e.g., vismodegib; Wu et al., 2012, PNAS 109:13644-13649), which have been approved for use in basal cell carcinoma, may be effective in the treatment of meningiomas with activating SMO mutations. Similarly, drugs that inhibit PI3K/AKT/mTOR pathway might prove to be effective in AKT1/PIK3CA/PIK3R1 mutant meningiomas. Clinically, although most of the non-NF2 mutant meningiomas have low potential for malignant transformation, they nonetheless present significant clinical challenges. Their localization to the skull base with invasion of critical neurovascular structures typically results in residual tumor post-surgery with patients requiring post-operative radiation therapy. Identification of a chemotherapeutic agent with low toxicity might negate the need for use of irradiation, an independent risk factor for formation and possibly malignant transformation of meningiomas, in these benign tumors.

In addition, exome sequencing of anterior skull base meningiomas negative for mutations in NF2, TRAF7, KLF4, AKT1 and SMO revealed the recurrent A213D mutation in the PRKAR1A gene in 2 meningiomas.

| Amino Acid Sequences |
|---|
| NF2 (Transcript ID: ENST00000338641; Protein ID: ENSP00000344666) (SEQ ID NO: 1) |
| MAGAIASRMSFSSLKRKQPKTFTVRIVTMDAEMEFNCEMKWK |
| GKDLFDLVCRTLGLRETWFFGLQYTIKDTVAWLKMDKKVLDH |
| DVSKEEPVTFHFLAKFYPENAEEELVQEITQHLFFLQVKKQI |
| LDEKIYCPPEASVLLASYAVQAKYGDYDPSVHKRGFLAQEEL |
| LPKRVINLYQMTPEMWEERITAWYAEHRGRARDEAEMEYLKI |
| AQDLEMYGVNYFAIRNKKGTELLLGVDALGLHIYDPENRLTP |
| KISFPWNEIRNISYSDKEFTIKPLDKKIDVFKFNSSKLRVNK |
| LILQLCIGNHDLFMRRRKADSLEVQQMKAQAREEKARKQMER |
| QRLAREKQMREEAERTRDELERRLLQMKEEATMANEALMRSE |
| ETADLLAEKAQITEEEAKLLAQKAAEAEQEMQRIKATAIRTE |
| EEKRLMEQKVLEAEVLALKMAEESERRAKEADQLKQDLQEAR |
| EAERRAKQKLLEIATKPTYPPMNPIPAPLPPDIPSFNLIGDS |
| LSFDFKDTDMKRLSMEIEKEKVEYMEKSKHLQEQLNELKTEI |
| EALKLKERETALDILHNENSDRGGSSKHNTIKKLTLQSAKSR |
| VAFFEEL |
| TRAF7 (Transcript ID: ENST00000326181; Protein ID: ENSP00000318944) (SEQ ID NO: 2) |
| MSSGKSARYNRFSGGPSNLPTPDVTTGTRMETTFGPAFSAVT |
| TITKADGTSTYKQHCRTPSSSSTLAYSPRDEEDSMPPISTPR |
| RSDSAISVRSLHSESSMSLRSTFSLPEEEEEPEPLVFAEQPS |
| VKLCCQLCCSVFKDPVITTCGHTFCRRCALKSEKCPVDNVKL |
| TVVVNNIAVAEQIGELFIHCRHGCRVAGSGKPPIFEVDPRGC |
| PFTIKLSARKDHEGSCDYRPVRCPNNPSCPPLLRMNLEAHLK |
| ECEHIKCPHSKYGCTFIGNQDTYETHLETCRFEGLKEFLQQT |
| DDRFHEMHVALAQKDQEIAFLRSMLGKLSEKIDQLEKSLELK |
| FDVLDENQSKLSEDLMEFRRDASMLNDELSHINARLNMGILG |
| SYDPQQIFKCKGTFVGHQGPVWCLCVYSMGDLLFSGSSDKTI |
| KVWDTCTTYKCQKTLEGHDGIVLALCIQGCKLYSGSADCTII |
| VWDIQNLQKVNTIRAHDNPVCTLVSSHNVLFSGSLKAIKVWD |
| IVGTELKLKKELTGLNHWVRALVAAQSYLYSGSYQTIKIWDI |
| RTLDCIHVLQTSGGSVYSIAVTNHHIVCGTYENLIHVWDIES |

Amino Acid Sequences

KEQVRTLTGHVGTVYALAVISTPDQTKVFSASYDRSLRVWSM

DNMICTQTLLRHQGSVTALAVSRGRLFSGAVDSTVKVWTC

AKT1 (Transcript ID: ENST00000407796;
Protein ID: ENSP00000270202)
(SEQ ID NO: 3)
MSDVAIVKEGWLHKRGEYIKTWRPRYFLLKNDGTFIGYKERP

QDVDQREAPLNNFSVAQCQLMKTERPRPNTFIIRCLQWTTVI

ERTFHVETPEEREEWTTAIQTVADGLKKQEEEEMDFRSGSPS

DNSGAEEMEVSLAKPKHRVTMNEFEYLKLLGKGTFGKVILVK

EKATGRYYAMKILKKEVIVAKDEVAHTLTENRVLQNSRHPFL

TALKYSFQTHDRLCFVMEYANGGELFFHLSRERVFSEDRARF

YGAEIVSALDYLHSEKNVVYRDLKLENLMLDKDGHIKITDFG

LCKEGIKDGATMKTFCGTPEYLAPEVLEDNDYGRAVDWWGLG

VVMYEMMCGRLPFYNQDHEKLFELILMEEIRFPRTLGPEAKS

LLSGLLKKDPKQRLGGGSEDAKEIMQHRFFAGIVWQHVYEKK

LSPPFKPQVTSETDTRYFDEEFTAQMITITPPDQDDSMECVD

SERRPHFPQFSYSASGTA

KLF4 (Transcript ID: ENST00000374672;
Protein ID: ENSP00000363804)
(SEQ ID NO: 4)
MRQPPGESDMAVSDALLPSFSTFASGPAGREKTLRQAGAPNN

RWREELSHMKRLPPVLPGRPYDLAAATVATDLESGGAGAACG

GSNLAPLPRRETEEFNDLLDLDFILSNSLTHPPESVAATVSS

SASASASSSSSPSSSGPASAPSTCSFTYPIRAGNDPGVAPGGTG

GGLLYGRESAPPPTAPFNLADINDVSPSGGFVAELLRPELDP

VYIPPQQPQPPGGGLMGKFVLKASLSAPGSEYGSPSVISVSK

GSPDGSHPVVVAPYNGGPPRTCPKIKQEAVSSCTHLGAGPPL

SNGHRPAAHDFPLGRQLPSRTTPTLGLEEVLSSRDCHPALPL

PPGFHPHPGPNYPSFLPDQMQPQVPPLHYQELMPPGSCMPEE

PKPKRGRRSWPRKRTATHTCDYAGCGKTYTKSSHLKAHLRTH

TGEKPYHCDWDGCGWKFARSDELTRHYRKHTGHRPFQCQKCD

RAFSRSDHLALHMKRHF

SMO (Transcript ID: ENST00000249373;
Protein ID: ENSP00000249373)
(SEQ ID NO: 5)
MAAARPARGPELPLLGLLLLLLGDPGRGAASSGNATGPGPR

SAGGSARRSAAVTGPPPPLSHCGRAAPCEPLRYNVCLGSVLP

YGATSTLLAGDSDSQEEAHGKLVLWSGLRNAPRCWAVIQPLL

CAVYMPKCENDRVELPSRTLCQATRGPCAIVERERGWPDFLR

CTPDRFPEGCTNEVQNIKFNSSGQCEVPLVRTDNPKSWYEDV

EGCGIQCQNPLFTEAEHQDMHSYIAAFGAVTGLCTLFTLATF

VADWRNSNRYPAVILFYVNACFFVGSIGWLAQFMDGARREIV

CRADGTMRLGEPTSNETLSCVIIFVIVYYALMAGVVWFVVLT

YAWHTSFKALGTTYQPLSGKTSYFHLLTWSLPFVLTVAILAV

AQVDGDSVSGICFVGYKNYRYRAGFVLAPIGLVLIVGGYFLI

RGVMTLFSIKSNHPGLLSEKAASKINETMLRLGIFGFLAFGF

VLITFSCHFYDFFNQAEWERSFRDYVLCQANVTIGLPTKQPI

PDCEIKNRPSLLVEKINLFAMFGTGIAMSTWVWTKATLLIWR

RTWCRLTGQSDDEPKRIKKSKMIAKAFSKRHELLQNPGQELS

FSMHTVSHDGPVAGLAFDLNEPSADVSSAWAQHVTKMVARRG

AILPQDISVTPVATPVPPEEQANLWLVEAEISPELQKRLGRK

KKRRKRKKEVCPLAPPPELHPPAPAPSTIPRLPQLPRQKCLV

AAGAWGAGDSCRQGAWTLVSNPFCPEPSPPQDPFLPSAPAPV

AWAHGRRQGLGPIHSRTNLMDTELMDADSDF

PIK3CA (Transcript ID: ENST00000263967;
Protein ID: ENSP00000263967)
(SEQ ID NO: 6)
MPPRPSSGELWGIHLMPPRILVECLLPNGMIVTLECLREATL

ITIKHELFKEARKYPLHQLLQDESSYIFVSVTQEAEREEFFD

ETRRLCDLRLFQPFLKVIEPVGNREEKILNREIGFAIGMPVC

EFDMVKDPEVQDFRRNILNVCKEAVDLRDLNSPHSRAMYVYP

PNVESSPELPKHIYNKLDKGQIIVVIWVIVSPNNDKQKYTLK

INHDCVPEQVIAEAIRKKTRSMLLSSEQLKLCVLEYQGKYIL

KVCGCDEYFLEKYPLSQYKYIRSCIMLGRMPNLMLMAKESLY

SQLPMDCFTMPSYSRRISTATPYMNGETSTKSLWVINSALRI

KILCATYVNVNIRDIDKIYVRTGIYHGGEPLCDNVNTQRVPC

SNPRWNEWLNYDIYIPDLPRAARLCLSICSVKGRKGAKEEHC

PLAWGNINLFDYTDTLVSGKMALNLWPVPHGLEDLLNPIGVT

GSNPNKETPCLELEFDWFSSVVKFPDMSVIEEHANWSVSREA

GFSYSHAGLSNRLARDNELRENDKEQLKAISTRDPLSEITEQ

EKDFLWSHRHYCVTIPEILPKLLLSVKWNSRDEVAQMYCLVK

DWPPIKPEQAMELLDCNYPDPMVRGFAVRCLEKYLTDDKLSQ

YLIQLVQVLKYEQYLDNLLVRFLLKKALTNQRIGHFFFWHLK

SEMHNKTVSQRFGLLLESYCRACGMYLKHLNRQVEAMEKLIN

LTDILKQEKKDETQKVQMKFLVEQMRRPDFMDALQGFLSPLN

PAHQLGNLRLEECRIMSSAKRPLWLNWENPDIMSELLFQNNE

IIFKNGDDLRQDMLTLQIIRIMENIWQNQGLDLRMLPYGCLS

IGDCVGLIEVVRNSHTIMQIQCKGGLKGALQFNSHTLHQWLK

DKNKGEIYDAAIDLFTRSCAGYCVATFILGIGDRHNSNIMVK

DDGQLFHIDFGHFLDHKKKKFGYKRERVPFVLTQDFLIVISK

GAQECTKTREFERFQEMCYKAYLAIRQHANLFINLFSMMLGS

GMPELQSFDDIAYIRKTLALDKTEQEALEYFMKQMNDAHHGG

WTTKMDWIFHTIKQHALN

Amino Acid Sequences

PIK3R1 (Transcript ID: ENST00000336483; Protein ID: ENSP00000428056)
(SEQ ID NO: 7)
MSAEGYQYRALYDYKKEREEDIDLHLGDILTVNKGSLVALGF
SDGQEARPEEIGWLNGYNETTGERGDFPGTYVEYIGRKKISP
PTPKPRPPRPLPVAPGSSKTEADVEQQALTLPDLAEQFAPPD
IAPPLLIKLVEAIEKKGLECSTLYRTQSSSNLAELRQLLDCD
TPSVDLEMIDVHVLADAFKRYLLDLPNPVIPAAVYSEMISLA
PEVQSSEEYIQLLKKLIRSPSIPHQYWLTLQYLLKHFFKLSQ
TSSKNLLNARVLSEIFSPMLRFSAASSDNTENLIKVIEILI
GDYTLTLRKGGNNKLIKIFHRDGKYGFSDPLTFSSVVELINH
STEWNERQPAPALPPKPPKPTTVANNGMNNNMSLQDAEWYWG
DISREEVNEKLRDTADGTFLVRDASTKMHYRNESLAQYNPKL
DVKLLYPVSKYQQDQVVKEDNIEAVGKKLHEYNTQFQEKSRE
YDRLYEEYTRTSQEIQMKRTAIEAFNETIKIFEEQCQTQERY
SKEYIEKFKREGNEKEIQRIMHNYDKLKSRISEIIDSRRRLE
EDLKKQAAEYREIDKRMNSIKPDLIQLRKTRDQYLMWLTQKG
VRQKKLNEWLGNENTEDQYSLVEDDEDLPHHDEKTWNVGSSN
RNKAENLLRGKRDGTFLVRESSKQGCYACSVVVDGEVKHCVI
NKTATGYGFAEPYNLYSSLKELVLHYQHTSLVQHNDSLNVTL
AYPVYAQQRR BRCA1 (Transcript ID: ENST00000357654; Protein ID: ENSP00000350283)
(SEQ ID NO: 8)
MDLSALRVEEVQNVINAMQKILECPICLELIKEPVSTKCDHI
FCKFCMLKLLNQKKGPSQCPLCKNDITKRSLQESTRFSQLVE
ELLKIICAFQLDTGLEYANSYNFAKKENNSPEHLKDEVSIIQ
SMGYRNRAKRLLQSEPENPSLQETSLSVQLSNLGTVRTLRTK
QRIQPQKTSVYIELGSDSSEDTVNKATYCSVGDQELLQITPQ
GTRDEISLDSAKKAACEFSETDVTNTEHHQPSNNDLNTTEKR
AAERHPEKYQGSSVSNLHVEPCGTNTHASSLQHENSSLLLTK
DRMNVEKAEFCNKSKQPGLARSQHNRWAGSKETCNDRRTPST
EKKVDLNADPLCERKEWNKQKLPCSENPRDTEDVPWITLNSS
IQKVNEWFSRSDELLGSDDSHDGESESNAKVADVLDVLNEVD
EYSGSSEKIDLLASDPHEALICKSERVHSKSVESNIEDKIFG
KTYRKKASLPNLSHVTENLIIGAFVTEPQIIQERPLTNKLKR
KRRPTSGLHPEDFIKKADLAVQKTPEMINQGTNQTEQNGQVM
NITNSGHENKTKGDSIQNEKNPNPIESLEKESAFKTKAEPIS
SSISNMELELNIHNSKAPKKNRLRRKSSTRHIHALELVVSRN
LSPPNCTELQIDSCSSSEEIKKKKYNQMPVRHSRNLQLMEGK
EPATGAKKSNKPNEQTSKRHDSDTFPELKLTNAPGSFTKCSN
TSELKEFVNPSLPREEKEEKLETVKVSNNAEDPKDLMLSGER
VLQTERSVESSSISLVPGTDYGTQESISLLEVSTLGKAKTEP
NKCVSQCAAFENPKGLIHGCSKDNRNDTEGFKYPLGHEVNHS
RETSIEMEESELDAQYLQNTFKVSKRQSFAPFSNPGNAEEEC
ATFSAHSGSLKKQSPKVTFECEQKEENQGKNESNIKPVQTVN
ITAGFPVVGQKDKPVDNAKCSIKGGSRFCLSSQFRGNETGLI
TPNKHGLLQNPYRIPPLFPIKSFVKTKCKKNLLEENFEEHSM
SPEREMGNENIPSTVSTISRNNIRENVFKEASSSNINEVGSS
TNEVGSSINEIGSSDENIQAELGRNRGPKLNAMLRLGVLQPE
VYKQSLPGSNCKHPEIKKQEYEEVVQTVNTDFSPYLISDNLE
QPMGSSHASQVCSETPDDLLDDGEIKEDTSFAENDIKESSAV
FSKSVQKGELSRSPSPFTHTHLAQGYRRGAKKLESSEENLSS
EDEELPCFQHLLFGKVNNIPSQSTRHSTVATECLSKNTEENL
LSLKNSLNDCSNQVILAKASQEHHLSEETKCSASLFSSQCSE
LEDLTANTNTQDPFLIGSSKQMRHQSESQGVGLSDKELVSDD
EERGTGLEENNQEEQSMDSNLGEAASGCESETSVSEDCSGLS
SQSDILTTQQRDTMQHNLIKLQQEMAELEAVLEQHGSQPSNS
YPSIISDSSALEDLRNPEQSTSEKAVLTSQKSSEYPISQNPE
GLSADKFEVSADSSTSKNKEPGVERSSPSKCPSLDDRWYMHS
CSGSLQNRNYPSQEELIKVVDVEEQQLEESGPHDLTETSYLP
RQDLEGTPYLESGISLFSDDPESDPSEDRAPESARVGNIPSS
TSALKVPQLKVAESAQSPAAAHTTDTAGYNAMEESVSREKPE
LTASTERVNKRMSMVVSGLTPEEFMLVYKFARKHHITLTNLI
TEETTHVVMKTDAEFVCERTLKYFLGIAGGKWVVSYFWVTQS
IKERKMLNEHDFEVRGDVVNGRNHQGPKRARESQDRKIFRGL
EICCYGPFTNMPTDQLEWMVQLCGASVVKELSSFTLGTGVHP
IVVVQPDAWTEDNGFHAIGQMCEAPVVTREWVLDSVALYQCQ
ELDTYLIPQIPHSHY CREBBP (Transcript ID: ENST00000262367; Protein ID: ENSP00000262367)
(SEQ ID NO: 9)
MAENLLDGPPNPKRAKLSSPGFSANDSTDFGSLFDLENDLPD
ELIPNGGELGLLNSGNLVPDAASKHKQLSELLRGGSGSSINP
GIGNVSASSPVQQGLGGQAQGQPNSANMASLSAMGKSPLSQG
DSSAPSLPKQAASTGPTPAASQALNPQAQKQVGLATSSPAT
SQTGPGICMNANFNQTHPGLLNSNSGHSLINQASQGQAQVMN
GSLGAAGRGRGAGMPYPTPAMQGASSSVLAETLTQVSPQMTG
HAGLNTAQAGGMAKMGITGNTSPFGQPFSQAGGQPMGATGVN
PQLASKQSMVNSLPTFPTDIKNTSVTNVPNMSQMQTSVGIVP
TQAIATGPTADPEKRKLIQQQLVLLLHAHKCQRREQANGEVR

Amino Acid Sequences

ACSLPHCRTMKNVLNHMTHCQAGKACQVAHCASSRQIISHWK

NCTRHDCPVCLPLKNASDKRNQQTILGSPASGIQNTIGSVGT

GQQNATSLSNPNPIDPSSMQRAYAALGLPYMNQPQTQLQPQV

PGQQPAQPQTHQQMRTLNPLGNNPMNIPAGGITTDQQPPNLI

SESALPTSLGATNPLMNDGSNSGNIGTLSTIPTAAPPSSTGV

RKGWHEHVTQDLRSHLVHKLVQAIFPTPDPAALKDRRMENLV

AYAKKVEGDMYESANSRDEYYHLLAEKIYKIQKELEEKRRSR

LHKQGILGNQPALPAPGAQPPVIPQAQPVRPPNGPLSLPVNR

MQVSQGMNSFNPMSLGNVQLPQAPMGPRAASPMNHSVQMNSM

GSVPGMAISPSRMPQPPNMMGAHTNNMMAQAPAQSQFLPQNQ

FPSSSGAMSVGMGQPPAQTGVSQGQVPGAALPNPLNMLGPQA

SQLPCPPVTQSPLHPTPPPASTAAGMPSLQHTTPPGMTPPQP

AAPTQPSTPVSSSGQTPTPTPGSVPSATQTQSTPTVQAAAQA

QVTPQPQTPVQPPSVATPQSSQQQPTPVHAQPPGTPLSQAAA

SIDNRVPTPSSVASAETNSQQPGPDVPVLEMKTETQAEDTEP

DPGESKGEPRSEMMEEDLQGASQVKEETDIAEQKSEPMEVDE

KKPEVKVEVKEEEESSSNGTASQSTSPSQPRKKIFKPEELRQ

ALMPTLEALYRQDPESLPFRQPVDPQLLGIPDYFDIVKNPMD

LSTIKRKLDTGQYQEPWQYVDDVWLMFNNAWLYNRKTSRVYK

FCSKLAEVFEQEIDPVMQSLGYCCGRKYEFSPQTLCCYGKQL

CTIPRDAAYYSYQNRYHFCEKCFTEIQGENVTLGDDPSQPQT

TISKDQFEKKKNDTLDPEPFVDCKECGRKMHQICVLHYDIIW

PSGFVCDNCLKKTGRPRKENKFSAKRLQTTRLGNHLEDRVNK

FLRRQNHPEAGEVFVRVVASSDKTVEVKPGMKSRFVDSGEMS

ESFPYRTKALFAFEEIDGVDVCFFGMHVQEYGSDCPPPNTRR

VYISYLDSIHFFRPRCLRTAVYHEILIGYLEYVKKLGYVTGH

IWACPPSEGDDYIFHCHPPDQKIPKPKRLQEWYKKMLDKAFA

ERIIHDYKDIFKQATEDRLTSAKELPYFEGDFWPNVLEESIK

ELEQEEEERKKEESTAASETTEGSQGDSKNAKKKNNKKTNKN

KSSISRANKKKPSMPNVSNDLSQKLYATMEKHKEVFFVIHLH

AGPVINTLPPIVDPDPLLSCDLMDGRDAFLTLARDKHWEFSS

LRRSKWSTLCMLVELHTQGQDRFVYTCNECKHHVETRWHCTV

CEDYDLCINCYNTKSHAHKMVKWGLGLDDEGSSQGEPQSKSP

QESRRLSIQRCIQSLVHACQCRNANCSLPSCQKMKRVVQHTK

GCKRKTNGGCPVCKQLIALCCYHAKHCQENKCPVPFCLNIKH

KLRQQQIQHRLQQAQLMRRRMATMNTRNVPQQSLPSPTSAPP

GTPTQQPSTPQTPQPPAQPQPSPVSMSPAGFPSVARTQPPTT

VSTGKPTSQVPAPPPPAQPPPAAVEAARQIEREAQQQQHLYR

VNINNSMPPGRTGMGTPGSQMAPVSLNVPRPNQVSGPVMPSM

PPGQWQQAPLPQQQPMPGLPRPVISMQAQAAVAGPRMPSVQP

PRSISPSALQDLLRTLKSPSSPQQQQQVLNILKSNPQLMAAF

IKQRTAKYVANQPGMQPQPGLQSQPGMQPQPGMHQQPSLQNL

NAMQAGVPRPGVPPQQQAMGGLNPQGQALNIMNPGHNPNMAS

MNPQYREMLRRQLLQQQQQQQQQQQQQQQQQGSAGMAGGMA

GHGQFQQPQGPGGYPPAMQQQRMQQHLPLQGSSMGQMAAQM

GQLGQMGQPGLGADSTPNIQQALQQRILQQQQMKQQIGSPGQ

PNPMSPQQHMLSGQPQASHLPGQQIATSLSNQVRSPAPVQSP

RPQSQPPHSSPSPRIQPQPSPHHVSPQTGSPHPGLAVTMASS

IDQGHLGNPEQSAMLPQLNTPSRSALSSELSLVGDTTGDTLE

KFVEGL

SMARCB1 (Transcript ID: ENST00000263121;
Protein ID: ENSP00000263121)
(SEQ ID NO: 10)
MMMMALSKTFGQKPVKFQLEDDGEFYMIGSEVGNYLRMFRGS

LYKRYPSLWRRLATVEERKKIVASSHGKKTKPNTKDHGYTTL

ATSVTLLKASEVEEILDGNDEKYKAVSISTEPPTYLREQKAK

RNSQWVPTLPNSSHHLDAVPCSTTINRNRMGRDKKRTFPLCF

DDHDPAVIHENASQPEVLVPIRLDMEIDGQKLRDAFTWNMNE

KLMTPEMFSEILCDDLDLNPLTFVPAIASAIRQQIESYPTDS

ILEDQSDQRVIIKLNIHVGNISLVDQFEWDMSEKENSPEKFA

LKLCSELGLGGEFVTTIAYSIRGQLSWHQKTYAFSENPLPTV

EIAIRNTGDADQWCPLLETLTDAEMEKKIRDQDRNTRRMRRL

ANTAPAW

PRKAR1A (Transcript ID: ENST00000589228;
Protein ID: ENSP00000464977)
(SEQ ID NO: 11)
MESGSTAASEEARSLRECELYVQKHNIQALLKDSIVQLCTAR

PERPMAFLREYFERLEKEEAKQIQNLQKAGTRTDSREDEISP

PPPNPVVKGRRRRGAISAEVYTEEDAASYVRKVIPKDYKTMA

ALAKAIEKNVLFSHLDDNERSDIFDAMFSVSFIAGETVIQQG

DEGDNFYVIDQGETDVYVNNEWATSVGEGGSFGELALIYGTP

RAATVKAKTNVKLWGIDRDSYRRILMGSTLRKRKMYEEFLSK

VSILESLDKWERLTVADALEPVQFEDGQKIVVQGEPGDEFFI

ILEGSAAVLQRRSENEEFVEVGRLGPSDYFGEIALLMNRPRA

ATVVARGPLKCVKLDRPRFERVLGPCSDILKRNIQQYNSFVS

LSV

The disclosures of each and every patent, patent application, website and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variation.

What is claimed is:

1. A method comprising:
a) obtaining a biological sample from a subject;
b) detecting at least one KLF4 K409Q mutation in the sample by performing an assay on the biological sample selected from the group consisting of PCR, Northern blotting, Southern blotting, DNA array analysis, and direct sequence analysis, thereby identifying the subject as having a meningioma; and
c) administering a meningioma treatment to the subject, wherein the treatment is at least one selected from the group consisting of surgery and radiation.

2. The method of claim 1, wherein the assay comprises contacting the sample with a nucleic acid probe for detection of the KLF4 K409Q mutation.

3. The method of claim 1, wherein the assay comprises contacting the sample with a nucleic acid probe for amplification of a nucleic acid molecule comprising the KLF4 K409Q mutation.

* * * * *